US009376429B2

(12) United States Patent
Kim et al.

(10) Patent No.: US 9,376,429 B2
(45) Date of Patent: Jun. 28, 2016

(54) SODIUM CHANNEL BLOCKERS, PREPARATION METHOD THEREOF AND USE THEREOF

(71) Applicant: Daewoong Pharmaceutical Co., Ltd., Gyeonggi-do (KR)

(72) Inventors: Ha Young Kim, Seoul (KR); In Woo Kim, Seoul (KR); Sun Ah Jun, Gyeonggi-do (KR); Yun Soo Na, Gyeonggi-do (KR); Hyung Geun Lee, Gyeonggi-do (KR); Min Jae Cho, Gyeonggi-do (KR); Jun Hee Lee, Gwangjin-gu (KR); Hyo Shin Kim, Yeonsu-Gu (KR); Yun Soo Yoon, Gyeonggi-do (KR); Kyung Ha Chung, Gyeonggi-do (KR); Ji Duck Kim, Gyeonggi-do (KR)

(73) Assignee: Daewoong Pharmaceutical Co., Ltd., Gyeonggi-do (KR)

( * ) Notice: Subject to any disclaimer, the term of this patent is extended or adjusted under 35 U.S.C. 154(b) by 0 days.

(21) Appl. No.: 14/435,473

(22) PCT Filed: Oct. 15, 2013

(86) PCT No.: PCT/KR2013/009206
§ 371 (c)(1),
(2) Date: Apr. 14, 2015

(87) PCT Pub. No.: WO2014/061970
PCT Pub. Date: Apr. 24, 2014

(65) Prior Publication Data
US 2015/0336944 A1 Nov. 26, 2015

(30) Foreign Application Priority Data

Oct. 15, 2012 (KR) .................. 10-2012-0114414

(51) Int. Cl.
*C07D 417/12* (2006.01)
*C07D 417/14* (2006.01)

(52) U.S. Cl.
CPC ............ *C07D 417/12* (2013.01); *C07D 417/14* (2013.01)

(58) Field of Classification Search
None
See application file for complete search history.

(56) References Cited

U.S. PATENT DOCUMENTS

| 7,858,786 B2 | 12/2010 | Wilson et al. |
| 7,989,481 B2 | 8/2011 | Neubert et al. |
| 2010/0197655 A1 | 8/2010 | Beaudoin et al. |
| 2012/0010182 A1* | 1/2012 | Brown ................. A61K 31/427 514/210.2 |

FOREIGN PATENT DOCUMENTS

| EP | 1088819 A2 | 4/2001 |
| WO | WO-2005013914 A2 | 2/2005 |
| WO | WO-2005054176 A1 | 6/2005 |
| WO | WO-2008118758 A1 | 10/2008 |
| WO | WO-2009012242 A2 | 1/2009 |
| WO | WO-2010079443 A1 | 7/2010 |
| WO | WO-2012004706 A2 | 1/2012 |
| WO | WO-2012004743 A1 | 1/2012 |

OTHER PUBLICATIONS

International Search Report and Written Opinion from PCT/KR2013/009206 dated Jan. 10, 2014.
P. Yogeeswari, et al. "Ion Channels as Important Targets for Antiepileptic Drug Design", Current Drug Targets, 2004, 5, 589-602.
Noble, "Unraveling the genetics and mechanisms of cardiac arrhythmia", PNAS, Apr. 30, 2002, vol. 99, No. 9, 5755-5726.
Cannon, "Spectrum of sodium channel disturbances in the nondystrophic myotonias and periodic paralyses", Kidney International, vol. 57 (2000), pp. 772-779.
Meisler, et al., "Mutations of voltage-gated sodium channels in movement disorders and epilepsy", Sodium Channels and Neuronal Hyperxcitability, Novartis 241, 2002.
Joel A. Black et al., "Sensory neuron-specific sodium channel SNS is abnormally expressed in the brains of mice with experimental allergic encephalomyelitis and humans with multiple sclerosis", PNAS, Oct. 10, 2000, vol. 97, No. 21.
M. Renganathan, et al., "Expression of $Na_v1.8$ sodium channels perturbs the firing patterns of cerebellar purkinje cells", Brain Research 959 (2003) 235-242.
Jennifer M. Laird, et al., "Deficits in Visceral Pain and Referred Hyperalgesia in Nav1.8 (SNS/PN3)-Null Mice", The Journal of Neuroscience, Oct. 1, 2002, 22(19): 8352-8356.
Naoki Yoshimura, et al., "The Involvement of the Tetrodotoxin-Resistant Sodium Channel $Na_v1.8$ (PN3/SNS) in a Rat Model of Visceral Pain", The Journal of Neuroscience, Nov. 1, 2001, 21(21): 8690-8696.
Hurley, "Lamotrigine Update and Its Use in Mood Disorders", The Annals of Pharmacotherapy, May 2002, vol. 36.
John N. Wood, et al., "Voltage-Gated Sodium Channels and Pain Pathways", 2004.
Goldin, "Resurgence of Sodium Channel Research", Annu. Rev. Physiol. 2001, 63:871-94.

(Continued)

*Primary Examiner* — Timothy R Rozof
(74) *Attorney, Agent, or Firm* — Marshall, Gerstein & Borun LLP

(57) ABSTRACT

The present invention relates to a compound having a blocking effect against sodium ion channels, particularly Nav1.7, a preparation method thereof and the use thereof. A compound represented by formula 1 according to the invention, or a pharmaceutically acceptable salt, hydrate, solvate or isomer thereof may be effectively used for the prevention or treatment of pain, for example, acute pain, chronic pain, neuropathic pain, post-surgery pain, migraine, arthralgia, neuropathy, nerve injury, diabetic neuropathy, neuropathic disease, epilepsy, arrhythmia, myotonia, ataxia, multiple sclerosis, irritable bowel syndrome, urinary incontinence, visceral pain, depression, erythromelalgia, or paroxysmal extreme pain disorder (PEPD).

11 Claims, No Drawings

(56) References Cited

OTHER PUBLICATIONS

Juan J. Toledo-Aral, et al., "Identification of PN1, a predominant voltage-dependent sodium channel expressed principally in peripheral neurons", Proc. Natl. Acad. Sci., vol. 94, pp. 1527-1532, Feb. 1997.

Anthony M. Rush, et al., "A single sodium channel mutation produces hyper-or hypoexcitability in different types of neurons", PNAS, May 23, 2006, vol. 103, No. 21, 8245-8250.

Laiche Djouhri, et al., "Sensory and electrophysiological properties of guinea-pig sensory neurones, expressing $Na_v1.7$ (PN1) $NA^+$ channel α subunit protein", J. Physiol (2003), 546.2, pp. 565-576.

Sulayman D. Dib-Hajj, et al., "From genes to pain: $Na_v1.7$ and human pain disorders", TRENDS in Neurosciences, vol. 30, No. 11, 2007.

Caroline R. Fertleman, et al., "SCN9A Mutations in Paroxysmal Extreme Pain Disorder: Allelic Variants Underlie Distinct Channel Defects and Phenotypes", Neuron, 52, 767-774, Dec. 7, 2006.

James J. Cox, et al., "An SCN9A channelopathy causes congenital inability to experience pain", Nature, vol. 444, Dec. 14, 2006.

David Julius, et al., "Molecular mechanisms of nociception", Nature, vol. 413, Sep. 13, 2001.

Wiffen P. Collins, et al., "Anticonvulsant drugs for acute and chronic pain (Review)", The Cochrane Collaboration, Issue 3, 2000.

David R. P. Guay, "Adjunctive Agents in the Management of Chronic Pain", Pharmacotherapy, vol. 21, No. 9, 2001.

Michael S. Gold, "Tetrodotoxin-resistant $Na^+$ currents and inflammatory hyperalgesia", Proc. Natl. Acad. Sci., vol. 96, pp. 7645-7649, Jul. 1999.

A. Sandner-Kiesling, et al., "Lamotrigine monotherapy for control of neuralgia after nerve section", Acta Anaesthesiol Scand 2002, 46, 1261-1264.

\* cited by examiner

SODIUM CHANNEL BLOCKERS, PREPARATION METHOD THEREOF AND USE THEREOF

TECHNICAL FIELD

The present invention relates to a compound having a blocking effect against sodium ion channels, particularly Nav1.7, a preparation method thereof and the use thereof.

BACKGROUND ART

Various channels (molecular sensors) are present in the terminal of nociceptive nerves, and various voltage-gated Na+ channels (Nav channels) and K+ channels (Kay channels) are present in nerve trunks. In addition, membrane potential (i.e., generator potential) is present in the nerve terminal by various channels. When such Nav channels are depolarized by generator potential in the nerve terminal, they play an important role in generating action voltage. Thus, the Nav channels play an important role in various diseases, including epilepsy (see Yogeeswari et al., Curr. Drug Targets, 5(7):589-602 (2004)), arrhythmia (see Noble D., Proc. Natl. Acad. Sci. USA, 99(9):5755-6 (2002)), myotonia (see Cannon, S. C. et al., Kidney Int., 57(3):772-9(2000)), ataxia (see Meisler, M. H. et al., Novartis Found Symp., 241:72-81 (2002)), multiple sclerosis (see Black, J. A. et al., Proc. Natl. Acad. Sci. USA, 97(21):11598-11602 (2000), and Renganathan, M. M. et al., Brain Res., 959 (2): 235-242 (2003)), irritable bowel syndrome (see Laird, J. M. et al., J. Neurosci., 22(19):8352-3856 (2002)), urinary incontinence and visceral pain (see Yoshimura, N. S., et al., J. Neurosci., 21(21): 8690-8696 (2001)), depression (see Hurley, S. C. et al., Ann, Pharmacother, 36(5):860-873 (2002)), and pain (see Wood, J. N. et al., J. Neurobiol., 61(1):55-71 (2004)). Currently, ten Nav channels (Na1.1-1.9 and Nax) are found in humans. Among them, four channels (Na1.3, Na1.7, Na1.8 and Na1.9) are known to have a close connection with the transmission of pain signals, and thus are recognized as important analgesic targets.

There are a total of ten known Nav channels as summarized in Table 1 below. Among the ten channels, nine channels (Nav1.1-NaV1.9) form channels (see Goldin, A. L. et al., Annu. Rev. Physiol., 63:871-894 (2001)). Among them, Nav1.3, Nav1.6, Nav1.7, Nav1.8 and Nav1.9 are expressed in DRG.

TABLE 1

| Type | Gene | Primary tissue | TTX IC-50 nM | Indications |
|---|---|---|---|---|
| Nav1.1 | SCN1A | CNS/PNS | 10 | Pain, epilepsy, neurodegeneration |
| Nav1.2 | SCN2A | CNS | 10 | Neurodegeneration, epilepsy |
| Nav1.3 | SCN3A | CNS | 15 | Pain, epilepsy |
| Nav1.4 | SCN4A | Sk.muscle | 25 | Myotonia |
| Nav1.5 | SCN5A | Heart | 2000 | Arrhythmia |
| Nav1.6 | SCN6A | CNS/PNS | 6 | Pain, movement disorders |
| Nav1.7 | SCN7A | PNS | 25 | Pain, disorder of neuroendocrine system |
| Nav1.8 | SCN8A | PNS | 50000 | Pain |
| Nav1.9 | SCN9A | PNS | 1000 | Pain |

Particularly, Nav1.7 is known to be highly expressed mainly in dorsal root ganglia (DRG) and sympathetic ganglia (see Toledo-Aral, J. J. et al., Proc. Natl. Acad. Sci. USA., 94:1527-1532 (1997), and Rush, A. M. et al. Proc. Natl. Acad. Sci. USA., 103:8245-8250 (2006)). In DRG that are sensory ganglia, the Nav1.7 channel is expressed in A- or C-fiber neurons, but frequently distributed in small neurons having a deep connection with pain. Particularly, 85% of DRG are present in cells defined as nociceptors (see Djouhri, L. et al., J. Physiol., 546: 565-576 (2003)). This fact indicates that Nav1.7 has a close connection with pain.

The fact that the Nav1.7 channel has a close connection with pain is well demonstrated in the results of not only animal studies, but also human disease studies. The results of animal studies indicated that, when inflammation occurs, the gene transcript of Nav1.7 significantly increases and the expression of proteins also increases. This increase in transcript is believed to be attributable to an increase in NGF. The increased expression of Nav1.7 is believed to be the direct cause of an increase in excitability of sensory cells. In particular, when the gene of the Nav1.7 channel is removed or reduced, inflammatory pain is greatly reduced. However, animal studies do not indicate that the removal or reduction of the Nav1.7 channel gene reduces neuropathic pain. However, there are many evidences that Nav1.7 is involved in neuropathic pain in humans.

Examination results for lineages that feel severe pain or no pain give many answers to pain studies. Particularly, these results directly indicate the importance of Nav1.7 in causing pain. There are two types of inherited diseases that cause severe pain. In the case of erythromelalgia or erythermalgia among these diseases, severe pain is sometimes felt for a few hours when the body is slightly warm or takes exercises. In some cases, the skin becomes red, and the hand, the foot or the face swell. The results of genetic research indicated that SCN9A (the human gene name of Nav1.7) is present at chromosomal sites associated with diseases. Nine mutations of Nav1.7 were found until now. These mutations lower activation threshold or result in slow deactivation of the channel. Thus, these mutations can easily generate action potential even upon depolarization of some neurons (see Dib-Hajj, S D. et al., Trends in Neurosci., 30, 555-563:(2007)).

In the case of paroxysmal extreme pain disorder (PEPD) that is another inherited disease, pain is felt through life and caused when the bowels are evacuated or the anal region is stimulated. In addition to pain, the leg becomes red. As is known in the art, in PEPD, eight mutations occur in Nav1.7. These mutations occur mainly in sites that cause inactivation. The Nav channel has an inactivation ball in the linker between domains III and IV, and a peptide receiving region in the linker between the S5 and S6 segments of domains III and IV. Interestingly, mutations that cause PEPD all occur in these two regions. It appears that these cause a problem in the inactivation of Nav1.7. As expected, these mutations cause a problem in the inactivation of Nav1.7, resulting in slow deactivation of the channel (see Fertleman, C. R. et al., Neuron, 52, 767-774 (2006)). Thus, the amount of electric current that enters through the channel increases.

Still another inherited disease is congenital indifference to pain (CIP). This disease results from mutation of the Nav1.7 channel and exist in Pakistani and Chinese lineages. Persons suffering from this disease feel no pain (see Cox, J. J. et al., Nature, 444, 894-898 (2006)). Particularly, persons suffering from this disease do not feel almost all pains, including a pain caused by a burn, and organ pains (see Cox, J. J. et al., Nature, 444, 894-898 (2006)). CIP causes the loss of function of the Nav1.7 channel. Particularly, a mutation in this channel inhibits the expression of this channel. Thus, this channel is not expressed (see Cox, J. J. et al., Nature, 444, 894-898 (2006)). Interestingly, the knock-out of Nav1.7 does not influence other sensations (see Dib-Hajj, S D. et al., Trends in Neurosci., 30, 555-563 (2007)). However, it influences the olfactory sensation. This fact directly indicates that Nav1.7 does not overlap with other channels in pain transmission and the function thereof is not compensated for by other Nav channels.

As described above for the above diseases, when a mutation in the Nav1.7 channel causes a gain of function, severe pain is felt, and when it causes a loss of function, pain is relieved. This is a good clinical example that directly shows that the Nav1.7 channel is the major cause of pain. Thus, it is considered that an antagonist that inhibits this channel will naturally result in a pain-relieving effect.

However, if the Nav1.7 channel antagonist inhibits a plurality of Nav channels including the Nav1.7 channel, it can show adverse effects of various CNS disturbances, such as blurring of vision, dizziness, vomiting and depression. Particularly, if it inhibits the Nav1.5 channel, it can cause cardiac arrhythmia and heart failure, which threaten life. For these reasons, selective inhibition of the Nav1.7 channels is very important.

Pains can be largely classified into three: acute pain, inflammatory pain, and neuropathic pain. Acute pain plays an important protective function of maintaining the safety of organisms from stimuli that can cause tissue injury. Thus, it is generally temporary and intense. On the other hand, inflammatory pain can be longer lasting, and the intensity thereof further increases. Inflammatory pain is mediated by various substances that are released during inflammation, including substance P, histamine, acids, prostaglandin, bradykinin, CGRP, cytokines, ATP and other substances (see Julius, D. et al., Nature, 413 (6852):203-210 (2001)). The third pain is neuropathic and involves nerve injury or a nerve injury caused by viral infection. It causes reconstitution of circuits with neuron proteins to cause pathological "sensitization", which can result in chronic pain that is lasting for several years. This type of pain does not provide an advantage of adaptability and is difficult to treat by current therapy.

Particularly, neuropathic pain and intractable pain are great medical problems that have not been solved. Several hundred million patients are suffering from severe pain that is not well inhibited by current therapeutic methods. Drugs that are currently used for the treatment of pain include NSAIDS, COX-2 inhibitors, opioids, tricyclic antidepressants and anticonvulsants. Neuropathic pain is particularly difficult to treat, because it does not well respond to opioids until a high dose is reached. Currently, gabapentin is most widely used as a therapeutic agent against neuropathic pain, but it is effective for 60% of the patients and is not greatly effective. This drug is generally safe, but is problematic in terms of sedative action at high doses.

Accordingly, studies on the discovery of new regulators of the Nav1.7 channel (see Wiffen, P. S. et al., Cochrane Database Syst. Rev 3., (2000); Guay, D. R., Pharmacotherapy, 21(9):1070-1081 (2001)) and the use thereof for the treatment of acute pain (see Wiffen, P. S. et al., Cochrane Database Syst. Rev3., (2000)), chronic acute (see Guay, D. R., Pharmacotherapy, 21(9):1070-1081 (2001)), inflammatory pain (see Gold, M. S., Proc. Natl. Acad. Sci. USA., 96(14): 7645-7649 (1999)) and neuropathic pain (Sandner-Kiesling, A. G. et al., Acta. Anaesthesiol Scand., 46(10):1261-1264 (2002)) have been actively conducted by global pharmaceutical companies, including Merck, AstraZeneca and the like (see WO-A-2005/013914; WO-A-2005/054176; WO-A-2008/118758; EP-A-1088819; WO-A-2009/012242; US2010/0197655 A1; U.S. Pat. Nos. 7,858,786 B2; 7,989,481 B2).

Accordingly, the present inventors have conducted studies on novel compounds, and as a result, have found that compounds having chemical structures different from those of sodium channel blockers reported to date have excellent sodium channel blocking effects, thereby completing the present invention. Compounds falling within the scope of the present invention mainly have sodium channel blocking activity, but it is not excluded that products produced by a special in vivo environment or a metabolic process after absorption of the compounds in vivo will act as agonists and exhibit effective pharmacological action.

DISCLOSURE

Technical Problem

It is an object of the present invention to provide compounds having a blocking effect against sodium ion channels, particularly Nav1.7, a preparation method thereof and the use thereof.

Technical Solution

To achieve the above object, the present invention provides a compound represented by the following formula 1 or a pharmaceutically acceptable salt thereof:

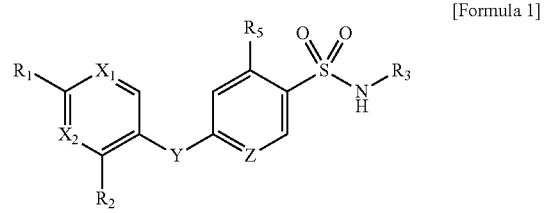

[Formula 1]

wherein $R_1$ is hydrogen, halogen, or aryl or heteroaryl selected from the group consisting of phenyl, pyridinyl, pyrimidinyl, furanyl, isoxazolyl, pyrazolyl and thienyl, wherein the aryl or heteroaryl is unsubstituted or substituted by one or two substituents independently selected from the group consisting of $C_{1-4}$ alkyl, $C_{1-4}$ haloalkyl and halogen, $R_2$ is aryl or heteroaryl selected from the group consisting of furanyl, imidazolyl, isoxazolyl, phenyl, pyrazolyl, pyridinyl, pyrimidinyl, thiazolyl and thienyl, wherein the aryl or heteroaryl is unsubstituted or substituted by one or two substituents independently selected from the group consisting of $C_{1-4}$ alkyl, $C_{3-6}$ cycloalkyl, halogen, morpholino, piperazinyl, piperidinyl, pyridinyl and pyrrolidinyl, $R_3$ is thiazolyl or thiadiazolyl, $X_1$ is CH or N, $X_2$ is CH or N, with the proviso that at least one among $X_1$ and $X_2$ is CH, Y is O or CH(OH), Z is $CR_4$, $R_4$ is H, halogen or CN, $R_5$ is H or halogen, with the proviso that if $R_2$ is pyrazolyl substituted by $C_{1-4}$ alkyl, one among $X_1$ and $X_2$ is N, and if $R_1$ is H or halogen, Y is CH(OH).

Preferably, $R_1$ is H; chloro; phenyl unsubstituted or substituted by one or two substituents independently selected from the group consisting of $C_{1-4}$ haloalkyl and halogen; pyridinyl unsubstituted or substituted by one or two halogens; unsubstituted pyrimidinyl; unsubstituted furanyl; unsubstituted isoxazolyl; pyrazolyl unsubstituted or substituted by $C_{1-4}$ alkyl; or unsubstituted thienyl.

Preferably, $R_1$ is H; chloro; phenyl unsubstituted or substituted by one or two substituents independently selected from the group consisting of $CF_3$, F and Cl; pyridinyl unsubstituted or substituted by one or two F; unsubstituted pyrimidinyl; unsubstituted furanyl; unsubstituted isoxazolyl; pyrazolyl unsubstituted or substituted by methyl; or unsubstituted thienyl.

Preferably, $R_2$ is unsubstituted furanyl; imidazolyl substituted by pyridinyl; isoxazolyl substituted by two $C_{1-4}$ alkyl; unsubstituted phenyl; pyrazolyl unsubstituted or substituted by $C_{1-4}$ alkyl or $C_{3-6}$ cycloalkyl; pyridinyl unsubstituted or substituted by one or two substituents selected from the group consisting of $C_{1-4}$ alkyl, halogen, morpholino, piperidinyl and pyrrolidinyl; pyrimidinyl unsubstituted or substituted by piperazinyl; thiazolyl substituted by $C_{3-6}$ cycloalkyl; or thienyl substituted by one or two $C_{1-4}$ alkyl.

Preferably, $R_2$ is unsubstituted furanyl; imidazolyl substituted by pyridinyl; isoxazolyl substituted by two methyl; unsubstituted phenyl; pyrazolyl unsubstituted or substituted by methyl or cyclopropyl; pyridinyl unsubstituted or substituted by one or two substituents selected from the group consisting of methyl, F, Cl, morpholino, piperidinyl and pyrrolidinyl; pyrimidinyl unsubstituted or substituted by piperazinyl; thiazolyl substituted by cyclopropyl; or thienyl substituted by one or two methyl.

Preferably, $R_4$ is H, F, Cl or CN.

Preferably, $R_5$ is H or F.

Preferably, $R_1$ is aryl or heteroaryl selected from the group consisting of phenyl, pyridinyl, pyrimidinyl, furanyl, isoxazolyl, pyrazolyl and thienyl, wherein the aryl or heteroaryl is unsubstituted or substituted by one or two substituents independently selected from the group consisting of $C_{1-4}$ alkyl, $C_{1-4}$ haloalkyl and halogen, $R_2$ is aryl or heteroaryl selected from the group consisting of furanyl, imidazolyl, isoxazolyl, pyrazolyl, pyridinyl, pyrimidinyl, thiazolyl and thienyl, wherein the aryl or heteroaryl is unsubstituted or substituted by one or two substituents independently selected from the group consisting of $C_{1-4}$ alkyl, $C_{3-6}$ cycloalkyl, halogen, morpholino, piperazinyl, piperidinyl, pyridinyl and pyrrolidinyl, $R_3$ is thiazolyl or thiadiazolyl, $X_1$ is CH or N, $X_2$ is CH or N, with the proviso that at least one among $X_1$ and $X_2$ is CH, Y is O, Z is $CR_4$, $R_4$ is H, halogen or CN, $R_5$ is H or halogen.

Preferably, $R_1$ is hydrogen, halogen, or aryl or heteroaryl selected from the group consisting of phenyl, pyridinyl and furanyl, wherein the aryl or heteroaryl is unsubstituted or substituted by halogen, $R_2$ is aryl or heteroaryl selected from the group consisting of furanyl, phenyl, pyrazolyl and pyridinyl, wherein the aryl or heteroaryl is unsubstituted or substituted by $C_{1-4}$ alkyl, $R_3$ is thiazolyl, $X_1$ is CH or N, $X_2$ is CH or N, with the proviso that at least one among $X_1$ and $X_2$ is CH, Y is CH(OH), Z is $CR_4$, $R_4$ is H or halogen, $R_5$ is H.

The representative compounds represented by the following formula 1 are as follows:

1) 3-cyano-4-((4-(furan-3-yl)-6-phenylpyridin-3-yl)oxy)-N-(thiazol-2-yl)benzenesulfonamide,
2) 3-cyano-4-((4-(1-methyl-1H-pyrazol-5-yl)-6-phenylpyridin-3-yl)oxy)-N-(thiazol-2-yl)benzenesulfonamide,
3) 3-cyano-4-((4-(furan-3-yl)-6-phenylpyridin-3-yl)oxy)-N-(1,2,4-thiadiazol-5-yl)benzenesulfonamide,
4) 3-cyano-4-((4-(1-methyl-1H-pyrazol-5-yl)-6-phenylpyridin-3-yl)oxy)-N-(1,2,4-thiadiazol-5-yl)benzenesulfonamide,
5) 3-cyano-4-(6-(3-fluorophenyl)-4-(furan-3-yl)pyridin-3-yloxy)-N-(thiazol-2-yl)benzenesulfonamide,
6) 3-cyano-4-(6-(2-fluorophenyl)-4-(furan-3-yl)pyridin-3-yloxy)-N-(thiazol-2-yl)benzenesulfonamide,
7) 3-cyano-4-(6-(4-fluorophenyl)-4-(furan-3-yl)pyridin-3-yloxy)-N-(thiazol-2-yl)benzenesulfonamide,
8) 3-cyano-4-(4-(furan-3-yl)-6-(3-(trifluoromethyl)phenyl)pyridin-3-yloxy)-N-(thiazol-2-yl)benzenesulfonamide,
9) 3-cyano-4-(2'-fluoro-4-(furan-3-yl)-2,4'-bipyridin-5-yloxy)-N-(thiazol-2-yl)benzenesulfonamide,
10) 3-cyano-4-(2'-fluoro-4-(furan-3-yl)-2,3'-bipyridin-5-yloxy)-N-(thiazol-2-yl)benzenesulfonamide,
11) 3-cyano-4-(6'-fluoro-4-(furan-3-yl)-2,3'-bipyridin-5-yloxy)-N-(thiazol-2-yl)benzenesulfonamide,
12) 3-cyano-4-(2',6'-difluoro-4-(furan-3-yl)-2,3'-bipyridin-5-yloxy)-N-(thiazol-2-yl)benzenesulfonamide,
13) 3-cyano-4-(4-(furan-3-yl)-2,3'-bipyridin-5-yloxy)-N-(thiazol-2-yl)benzenesulfonamide,
14) 3-cyano-4-(4-(furan-3-yl)-2,4'-bipyridin-5-yloxy)-N-(thiazol-2-yl)benzenesulfonamide,
15) 3-cyano-4-(4-(furan-3-yl)-6-(pyrimidin-5-yl)pyridin-3-yloxy)-N-(thiazol-2-yl)benzenesulfonamide,
16) 3-cyano-4-((4,6-di(furan-3-yl)pyridin-3-yl)oxy)-N-(thiazol-2-yl)benzenesulfonamide,
17) 4-((4,6-di(furan-3-yl)pyridin-3-yl)oxy)-3-fluoro-N-(thiazol-2-yl)benzenesulfonamide,
18) 3-cyano-4-((2'-fluoro-4-(1-methyl-1H-pyrazol-5-yl)-[2,3'-bipyridin]-5-yl)oxy)-N-(thiazol-2-yl)benzenesulfonamide,
19) 3-cyano-4-((6'-fluoro-4-(1-methyl-1H-pyrazol-5-yl)-[2,3'-bipyridin]-5-yl)oxy)-N-(thiazol-2-yl)benzenesulfonamide,
20) 3-cyano-4-((4-(furan-3-yl)-6-(thiophen-3-yl)pyridin-3-yl)oxy)-N-(thiazol-2-yl)benzenesulfonamide,
21) 3-fluoro-4-((4-(1-methyl-1H-pyrazol-5-yl)-[2,3'-bipyridin]-5-yl)oxy)-N-(thiazol-2-yl)benzenesulfonamide,
22) 3-fluoro-4-((4-(1-methyl-1H-pyrazol-5-yl)-6-(thiophen-3-yl)pyridin-3-yl)oxy)-N-(thiazol-2-yl)benzenesulfonamide,
23) 3-cyano-4-((6-(4-fluorophenyl)-4-(1-methyl-1H-pyrazol-5-yl)pyridin-3-yl)oxy)-N-(thiazol-2-yl)benzenesulfonamide,
24) 3-cyano-4-((6-(2-fluorophenyl)-4-(1-methyl-1H-pyrazol-5-yl)pyridin-3-yl)oxy)-N-(thiazol-2-yl)benzenesulfonamide,
25) 3-cyano-4-((6-(furan-3-yl)-4-(1-methyl-1H-pyrazol-5-yl)pyridin-3-yl)oxy)-N-(thiazol-2-yl)benzenesulfonamide,
26) 3-cyano-4-((6-(3-fluorophenyl)-4-(1-methyl-1H-pyrazol-5-yl)pyridin-3-yl)oxy)-N-(thiazol-2-yl)benzenesulfonamide,
27) 3-cyano-4-((2'-fluoro-4-(1-methyl-1H-pyrazol-5-yl)-[2,4'-bipyridin]-5-yl)oxy)-N-(thiazol-2-yl)benzenesulfonamide,
28) 4-((4,6-di(furan-3-yl)pyridin-3-yl)oxy)-N-(thiazol-2-yl)benzenesulfonamide, 29) 3-cyano-4-((2-fluoro-6'-phenyl-[3,4'-bipyridin]-3'-yl)oxy)-N-(thiazol-2-yl)benzenesulfonamide,
30) 3-cyano-4-((6-fluoro-6'-phenyl-[3,4'-bipyridin]-3'-yl)oxy)-N-(thiazol-2-yl)benzenesulfonamide,
31) 3-cyano-4-((2'-fluoro-6-phenyl-[4,4'-bipyridin]-3-yl)oxy)-N-(thiazol-2-yl)benzenesulfonamide,
32) 3-cyano-4-((6-fluoro-5-methyl-6'-phenyl-[3,4'-bipyridin]-3'-yl)oxy)-N-(thiazol-2-yl)benzenesulfonamide,
33) 3-cyano-4-((6'-phenyl-[3,4'-bipyridin]-3'-yl)oxy)-N-(thiazol-2-yl)benzenesulfonamide,
34) 3-cyano-4-((6-phenyl-4-(pyrimidin-5-yl)pyridin-3-yl)oxy)-N-(thiazol-2-yl)benzenesulfonamide,
35) 4-((3'-chloro-6-phenyl-[4,4'-bipyridin]-3-yl)oxy)-3-cyano-N-(thiazol-2-yl)benzenesulfonamide,
36) 3-cyano-4-((2',3'-dichloro-6-phenyl-[4,4'-bipyridin]-3-yl)oxy)-N-(thiazol-2-yl)benzenesulfonamide,
37) 3-cyano-4-((4-(3,5-dimethylisoxazol-4-yl)-6-phenylpyridin-3-yl)oxy)-N-(thiazol-2-yl)benzenesulfonamide,
38) 3-cyano-4-((4-(1-methyl-1H-pyrazol-4-yl)-6-phenylpyridin-3-yl)oxy)-N-(thiazol-2-yl)benzenesulfonamide,
39) 3-cyano-4-((6-phenyl-4-(1H-pyrazol-4-yl)pyridin-3-yl)oxy)-N-(thiazol-2-yl)benzenesulfonamide,
40) 3-cyano-4-((6-phenyl-[4,4'-bipyridin]-3-yl)oxy)-N-(thiazol-2-yl)benzenesulfonamide,
41) 3-cyano-4-((4-(2,5-dimethylthiophen-3-yl)-6-phenylpyridin-3-yl)oxy)-N-(thiazol-2-yl)benzenesulfonamide,
42) 3-cyano-4-((4-(5-methylthiophen-2-yl)-6-phenylpyridin-3-yl)oxy)-N-(thiazol-2-yl)benzenesulfonamide,
43) 3-cyano-4-((4-(2-cyclopropylthiazol-4-yl)-6-phenylpyridin-3-yl)oxy)-N-(thiazol-2-yl)benzenesulfonamide,
44) 3-cyano-4-((4-(1-cyclopropyl-1H-pyrazol-4-yl)-6-phenylpyridin-3-yl)oxy)-N-(thiazol-2-yl)benzenesulfonamide,
45) 3-cyano-4-((4-(furan-3-yl)-6-(1H-pyrazol-4-yl)pyridin-3-yl)oxy)-N-(thiazol-2-yl)benzenesulfonamide,
46) 3-cyano-4-((4-(furan-3-yl)-6-(1-methyl-1H-pyrazol-4-yl)pyridin-3-yl)oxy)-N-(thiazol-2-yl)benzenesulfonamide,
47) 3-fluoro-4-((2'-fluoro-4-(furan-3-yl)-[2,3'-bipyridin]-5-yl)oxy)-N-(thiazol-2-yl)benzenesulfonamide,
48) 3-fluoro-4-((6'-fluoro-4-(furan-3-yl)-[2,3'-bipyridin]-5-yl)oxy)-N-(thiazol-2-yl)benzenesulfonamide,
49) 3-cyano-4-((6-fluoro-[3,2':4',3''-terpyridin]-5'-yl)oxy)-N-(thiazol-2-yl)benzenesulfonamide,
50) 3-cyano-4-((6'-(3-fluorophenyl)-[3,4'-bipyridin]-3'-yl)oxy)-N-(thiazol-2-yl)benzenesulfonamide,
51) 3-cyano-4-((2-fluoro-[3,2':4',3''-terpyridin]-5'-yl)oxy)-N-(thiazol-2-yl)benzenesulfonamide,
52) 3-cyano-4-((6'-(2-fluorophenyl)-[3,4'-bipyridin]-3'-yl)oxy)-N-(thiazol-2-yl)benzenesulfonamide,
53) 3-cyano-4-((2,6-difluoro-[3,2':4',4''-terpyridin]-5'-yl)oxy)-N-(thiazol-2-yl)benzenesulfonamide,
54) 4-((4,6-bis(1-methyl-1H-pyrazol-4-yl)pyridin-3-yl)oxy)-3-cyano-N-(thiazol-2-yl)benzenesulfonamide,
55) 4-((4,6-bis(1-methyl-1H-pyrazol-4-yl)pyridin-3-yl)oxy)-3-cyano-N-(1,2,4-thiadiazol-5-yl)benzenesulfonamide,
56) 5-chloro-2-fluoro-4-((2'-fluoro-4-(furan-3-yl)-[2,3'-bipyridin]-5-yl)oxy)-N-(thiazol-4-yl)benzenesulfonamide,
57) 5-chloro-2-fluoro-4-((6'-fluoro-4-(furan-3-yl)-[2,3'-bipyridin]-5-yl)oxy)-N-(thiazol-4-yl)benzenesulfonamide,
58) 5-chloro-4-((2',6'-difluoro-4-(furan-3-yl)-[2,3'-bipyridin]-5-yl)oxy)-2-fluoro-N-(thiazol-4-yl)benzenesulfonamide,
59) 5-chloro-2-fluoro-4-((6-(3-fluorophenyl)-4-(furan-3-yl)pyridin-3-yl)oxy)-N-(thiazol-4-yl)benzenesulfonamide,
60) 5-chloro-2-fluoro-4-((6-(2-fluorophenyl)-4-(furan-3-yl)pyridin-3-yl)oxy)-N-(thiazol-4-yl)benzenesulfonamide,
61) 5-chloro-2-fluoro-4-((6-(4-fluorophenyl)-4-(furan-3-yl)pyridin-3-yl)oxy)-N-(thiazol-4-yl)benzenesulfonamide,
62) 5-chloro-2-fluoro-4-((2'-fluoro-4-(furan-3-yl)-[2,4'-bipyridin]-5-yl)oxy)-N-(thiazol-4-yl)benzenesulfonamide,
63) 5-chloro-2-fluoro-4-((6-(2-fluorophenyl)-4-(1-methyl-1H-pyrazol-4-yl)pyridin-3-yl)oxy)-N-(thiazol-4-yl)benzenesulfonamide 2,2,2-trifluoroacetate,
64) 5-chloro-2-fluoro-4-((6-(3-fluorophenyl)-4-(1-methyl-1H-pyrazol-5-yl)pyridin-3-yl)oxy)-N-(thiazol-2-yl)benzenesulfonamide,
65) 5-chloro-2-fluoro-4-((6-(4-fluorophenyl)-4-(1-methyl-1H-pyrazol-4-yl)pyridin-3-yl)oxy)-N-(thiazol-4-yl)benzenesulfonamide 2,2,2-trifluoroacetate,
66) 5-chloro-4-((6-(2,4-difluorophenyl)-4-(1-methyl-1H-pyrazol-4-yl)pyridin-3-yl)oxy)-2-fluoro-N-(thiazol-4-yl)benzenesulfonamide 2,2,2-trifluoroacetate,
67) 5-chloro-4-((6-(3,4-difluorophenyl)-4-(1-methyl-1H-pyrazol-4-yl)pyridin-3-yl)oxy)-2-fluoro-N-(thiazol-4-yl)benzenesulfonamide 2,2,2-trifluoroacetate,
68) 5-chloro-2-fluoro-4-((2'-fluoro-4-(1-methyl-1H-pyrazol-4-yl)-[2,4'-bipyridin]-5-yl)oxy)-N-(thiazol-4-yl)benzenesulfonamide 2,2,2-trifluoroacetate,
69) 5-chloro-2-fluoro-4-((2'-fluoro-4-(1-methyl-1H-pyrazol-4-yl)-[2,3'-bipyridin]-5-yl)oxy)-N-(thiazol-4-yl)benzenesulfonamide 2,2,2-trifluoroacetate,
70) 5-chloro-2-fluoro-4-((6'-fluoro-4-(1-methyl-1H-pyrazol-4-yl)-[2,3'-bipyridin]-5-yl)oxy)-N-(thiazol-4-yl)benzenesulfonamide 2,2,2-trifluoroacetate,
71) 5-chloro-2-fluoro-4-((6-(3-fluorophenyl)-4-(1-methyl-1H-pyrazol-5-yl)pyridin-3-yl)oxy)-N-(thiazol-4-yl)benzenesulfonamide,
72) 5-chloro-2-fluoro-4-((6-(3-fluorophenyl)-4-(2-(piperazin-1-yl)pyrimidin-4-yl)pyridin-3-yl)oxy)-N-(thiazol-4-yl)benzenesulfonamide,
73) 5-chloro-2-fluoro-4-((6'-(3-fluorophenyl)-[3,4'-bipyridin]-3'-yl)oxy)-N-(thiazol-2-yl)benzenesulfonamide,
74) 5-chloro-2-fluoro-4-((6'-(3-fluorophenyl)-[3,4'-bipyridin]-3'-yl)oxy)-N-(thiazol-4-yl)benzenesulfonamide,
75) 5-chloro-2-fluoro-4-((2''-fluoro-[3,4':2',4''-terpyridin]-5'-yl)oxy)-N-(thiazol-4-yl)benzenesulfonamide,
76) 5-chloro-2-fluoro-4-((6-(3-fluorophenyl)-4-(pyrimidin-5-yl)pyridin-3-yl)oxy)-N-(thiazol-4-yl)benzenesulfonamide,
77) 5-chloro-2-fluoro-4-((2'-fluoro-4-(pyrimidin-5-yl)-[2,4'-bipyridin]-5-yl)oxy)-N-(thiazol-4-yl)benzenesulfonamide,
78) 5-chloro-2-fluoro-4-((6-(3-fluorophenyl)-4-(1H-pyrazol-4-yl)pyridin-3-yl)oxy)-N-(thiazol-4-yl)benzenesulfonamide,
79) 5-chloro-2-fluoro-4-((2'-fluoro-6-(3-fluorophenyl)-[4,4'-bipyridin]-3-yl)oxy)-N-(thiazol-4-yl)benzenesulfonamide,
80) 5-chloro-4-((6-(3,4-difluorophenyl)-2'-fluoro-[4,4'-bipyridin]-3-yl)oxy)-2-fluoro-N-(thiazol-4-yl)benzenesulfonamide,
81) 5-chloro-4-((6'-(5-chloro-2-fluorophenyl)-[3,4'-bipyridin]-3'-yl)oxy)-2-fluoro-N-(thiazol-4-yl)benzenesulfonamide,
82) 5-chloro-4-((6'-(3,4-difluorophenyl)-[3,4'-bipyridin]-3'-yl)oxy)-2-fluoro-N-(thiazol-4-yl)benzenesulfonamide,
83) 3-cyano-4-((6-(3-fluorophenyl)-4-(1H-pyrazol-4-yl)pyridin-3-yl)oxy)-N-(thiazol-4-yl)benzenesulfonamide,
84) 3-cyano-4-((6'-(3-fluorophenyl)-[3,4'-bipyridin]-3'-yl)oxy)-N-(thiazol-4-yl)benzenesulfonamide, 85) 3-cyano-4-((6'-(3,4-difluorophenyl)-[3,4'-bipyridin]-3'-yl)oxy)-N-(thiazol-4-yl)benzenesulfonamide,
86) 3-cyano-4-((6'-(3-fluoro-4-(trifluoromethyl)phenyl)-[3,4'-bipyridin]-3'-yl)oxy)-N-(thiazol-4-yl)benzenesulfonamide,
87) 2,5-difluoro-4-((6'-(3-fluorophenyl)-[3,4'-bipyridin]-3'-yl)oxy)-N-(thiazol-4-yl)benzenesulfonamide,
88) 4-((6'-(3,4-difluorophenyl)-[3,4'-bipyridin]-3'-yl)oxy)-2,5-difluoro-N-(thiazol-4-yl)benzenesulfonamide,
89) 2,5-difluoro-4-((6'-(3-fluoro-4-(trifluoromethyl)phenyl)-[3,4'-bipyridin]-3'-yl)oxy)-N-(thiazol-4-yl)benzenesulfonamide,
90) 3-cyano-4-((6-(4-fluorophenyl)-4-(1H-pyrazol-4-yl)pyridin-3-yl)oxy)-N-(thiazol-4-yl)benzenesulfonamide,
91) 3-cyano-4-((6-(3,4-difluorophenyl)-4-(1H-pyrazol-4-yl)pyridin-3-yl)oxy)-N-(thiazol-4-yl)benzenesulfonamide,
92) 3-cyano-4-((6-(3-fluorophenyl)-4-(pyrimidin-5-yl)pyridin-3-yl)oxy)-N-(thiazol-4-yl)benzenesulfonamide,
93) 3-cyano-4-((6-(3,4-difluorophenyl)-4-(pyrimidin-5-yl)pyridin-3-yl)oxy)-N-(thiazol-4-yl)benzenesulfonamide,
94) 3-cyano-4-((6-(3-fluoro-4-(trifluoromethyl)phenyl)-4-(pyrimidin-5-yl)pyridin-3-yl)oxy)-N-(thiazol-4-yl)benzenesulfonamide,
95) 2,5-difluoro-4-((6-(3-fluorophenyl)-4-(pyrimidin-5-yl)pyridin-3-yl)oxy)-N-(thiazol-4-yl)benzenesulfonamide,
96) 4-((6-(3,4-difluorophenyl)-4-(pyrimidin-5-yl)pyridin-3-yl)oxy)-2,5-difluoro-N-(thiazol-4-yl)benzenesulfonamide,
97) 2,5-difluoro-4-((6-(3-fluoro-4-(trifluoromethyl)phenyl)-4-(pyrimidin-5-yl)pyridin-3-yl)oxy)-N-(thiazol-4-yl)benzenesulfonamide,
98) 5-chloro-4-((6-(3,4-difluorophenyl)-4-(1H-pyrazol-4-yl)pyridin-3-yl)oxy)-2-fluoro-N-(thiazol-4-yl)benzenesulfonamide,
99) 5-chloro-2-fluoro-4-((6'-(3-fluorophenyl)-5-(pyrrolidin-1-yl)-[3,4'-bipyridin]-3'-yl)oxy)-N-(thiazol-4-yl)benzenesulfonamide,
100) 5-chloro-2-fluoro-4-((6-(3-fluorophenyl)-4-(1-(pyridin-3-yl)-1H-imidazol-4-yl)pyridin-3-yl)oxy)-N-(thiazol-4-yl)benzenesulfonamide,
101) 5-chloro-2-fluoro-4-((6-(3-fluorophenyl)-2'-morpholino-[4,4'-bipyridin]-3-yl)oxy)-N-(thiazol-4-yl)benzenesulfonamide,
102) 5-chloro-2-fluoro-4-((6-(3-fluorophenyl)-2'-(piperidin-1-yl)-[4,4'-bipyridin]-3-yl)oxy)-N-(thiazol-4-yl)benzenesulfonamide,
103) 3-cyano-4-((2'-fluoro-6-(furan-3-yl)-[2,3'-bipyridin]-5-yl)oxy)-N-(thiazol-2-yl)benzenesulfonamide,
104) 3-cyano-4-((6'-fluoro-6-(furan-3-yl)-[2,3'-bipyridin]-5-yl)oxy)-N-(thiazol-2-yl)benzenesulfonamide,
105) 3-cyano-4-((6-(furan-3-yl)-[2,3'-bipyridin]-5-yl)oxy)-N-(thiazol-2-yl)benzenesulfonamide,
106) 3-cyano-4-((2-(furan-3-yl)-6-(pyrimidin-5-yl)pyridin-3-yl)oxy)-N-(thiazol-2-yl)benzenesulfonamide,
107) 3-cyano-4-((2'-fluoro-6-(1-methyl-1H-pyrazol-5-yl)-[2,4'-bipyridin]-5-yl)oxy)-N-(thiazol-2-yl)benzenesulfonamide,
108) 3-cyano-4-((6-(2-fluorophenyl)-2-(furan-3-yl)pyridin-3-yl)oxy)-N-(thiazol-2-yl)benzenesulfonamide,
109) 3-cyano-4-((6-(4-fluorophenyl)-2-(furan-3-yl)pyridin-3-yl)oxy)-N-(thiazol-2-yl)benzenesulfonamide,
110) 3-cyano-4-((6-(3-fluorophenyl)-2-(furan-3-yl)pyridin-3-yl)oxy)-N-(thiazol-2-yl)benzenesulfonamide,
111) 3-cyano-4-((6-(furan-3-yl)-[2,4'-bipyridin]-5-yl)oxy)-N-(thiazol-2-yl)benzenesulfonamide,
112) 3-cyano-4-((2'-fluoro-6-(furan-3-yl)-[2,4'-bipyridin]-5-yl)oxy)-N-(thiazol-2-yl)benzenesulfonamide,
113) 3-cyano-4-((2-(furan-3-yl)-6-(thiophen-3-yl)pyridin-3-yl)oxy)-N-(thiazol-2-yl)benzenesulfonamide,
114) 3-cyano-4-((2,6-di(furan-3-yl)pyridin-3-yl)oxy)-N-(thiazol-2-yl)benzenesulfonamide,
115) 3-cyano-4-((6'-fluoro-6-(1-methyl-1H-pyrazol-5-yl)-[2,3'-bipyridin]-5-yl)oxy)-N-(thiazol-2-yl)benzenesulfonamide,
116) 3-cyano-4-((2'-fluoro-6-(1-methyl-1H-pyrazol-5-yl)-[2,3'-bipyridin]-5-yl)oxy)-N-(thiazol-2-yl)benzenesulfonamide,
117) 3-cyano-4-((6-(3-fluorophenyl)-2-(1-methyl-1H-pyrazol-5-yl)pyridin-3-yl)oxy)-N-(thiazol-2-yl)benzenesulfonamide,
118) 3-cyano-4-((6-(2-fluorophenyl)-2-(1-methyl-1H-pyrazol-5-yl)pyridin-3-yl)oxy)-N-(thiazol-2-yl)benzenesulfonamide,
119) 3-cyano-4-((2-(1-methyl-1H-pyrazol-5-yl)-6-(thiophen-3-yl)pyridin-3-yl)oxy)-N-(thiazol-2-yl)benzenesulfonamide,
120) 3-cyano-4-((6-(1-methyl-1H-pyrazol-4-yl)-2-(1-methyl-1H-pyrazol-5-yl)pyridin-3-yl)oxy)-N-(thiazol-2-yl)benzenesulfonamide,
121) 3-cyano-4-((6-(isoxazol-4-yl)-2-(1-methyl-1H-pyrazol-5-yl)pyridin-3-yl)oxy)-N-(thiazol-2-yl)benzenesulfonamide,
122) 3-cyano-4-((6-(3-fluorophenyl)-2-(1-methyl-1H-pyrazol-4-yl)pyridin-3-yl)oxy)-N-(thiazol-2-yl)benzenesulfonamide,
123) 3-cyano-4-((2'-fluoro-6-(1-methyl-1H-pyrazol-4-yl)-[2,3'-bipyridin]-5-yl)oxy)-N-(thiazol-2-yl)benzenesulfonamide,
124) 3-cyano-4-((6'-fluoro-6-(1-methyl-1H-pyrazol-4-yl)-[2,3'-bipyridin]-5-yl)oxy)-N-(thiazol-2-yl)benzenesulfonamide,
125) 3-cyano-4-((2'-fluoro-6-(1-methyl-1H-pyrazol-4-yl)-[2,4'-bipyridin]-5-yl)oxy)-N-(thiazol-2-yl)benzenesulfonamide,
126) 3-cyano-4-((2',6'-difluoro-6-(1-methyl-1H-pyrazol-4-yl)-[2,3'-bipyridin]-5-yl)oxy)-N-(thiazol-2-yl)benzenesulfonamide,
127) 3-cyano-4-((2',6'-difluoro-6-(furan-3-yl)-[2,3'-bipyridin]-5-yl)oxy)-N-(thiazol-2-yl)benzenesulfonamide,
128) 3-cyano-4-((2',6'-difluoro-6-(1-methyl-1H-pyrazol-5-yl)-[2,3'-bipyridin]-5-yl)oxy)-N-(thiazol-2-yl)benzenesulfonamide,
129) 5-chloro-4-((2',6'-difluoro-6-(furan-3-yl)-[2,3'-bipyridin]-5-yl)oxy)-2-fluoro-N-(thiazol-4-yl)benzenesulfonamide,
130) 5-chloro-2-fluoro-4-((6'-fluoro-6-(furan-3-yl)-[2,3'-bipyridin]-5-yl)oxy)-N-(thiazol-4-yl)benzenesulfonamide,
131) 5-chloro-2-fluoro-4-((6-(4-fluorophenyl)-2-(furan-3-yl)pyridin-3-yl)oxy)-N-(thiazol-4-yl)benzenesulfonamide,
132) 5-chloro-2-fluoro-4-((2'-fluoro-6-(furan-3-yl)-[2,4'-bipyridin]-5-yl)oxy)-N-(thiazol-4-yl)benzenesulfonamide,
133) 5-chloro-2-fluoro-4-((6-(2-fluorophenyl)-2-(furan-3-yl)pyridin-3-yl)oxy)-N-(thiazol-4-yl)benzenesulfonamide,
134) 5-chloro-4-((2',6'-difluoro-6-(1-methyl-1H-pyrazol-5-yl)-[2,3'-bipyridin]-5-yl)oxy)-2-fluoro-N-(thiazol-4-yl)benzenesulfonamide,
135) 5-chloro-2-fluoro-4-((6-(4-fluorophenyl)-2-(1-methyl-1H-pyrazol-5-yl)pyridin-3-yl)oxy)-N-(thiazol-4-yl)benzenesulfonamide,
136) 5-chloro-2-fluoro-4-((6-(2-fluorophenyl)-2-(1-methyl-1H-pyrazol-5-yl)pyridin-3-yl)oxy)-N-(thiazol-4-yl)benzenesulfonamide, 137) 5-chloro-2-fluoro-4-((6'-fluoro-6-(1-methyl-1H-pyrazol-5-yl)-[2,3'-bipyridin]-5-yl)oxy)-N-(thiazol-4-yl)benzenesulfonamide, 138) 4-((4-chloro-2-(1-methyl-1H-pyrazol-5-yl)phenyl)(hydroxy)methyl)-N-(thiazol-2-yl)benzenesulfonamide, 139) 4-((4-chloro-2-(1H-pyrazol-4-yl)phenyl)(hydroxy)methyl)-3-fluoro-N-(thiazol-2-yl)benzenesulfonamide, 140) 4-((4-chloro-2-(furan-3-yl)phenyl)(hydroxy)methyl)-3-fluoro-N-(thiazol-2-yl)benzenesulfonamide, 141) 4-((2,4-di(furan-3-yl)phenyl)(hydroxy)methyl)-3-fluoro-N-(thiazol-2-yl)benzenesulfonamide, 142) 3-fluoro-4-(hydroxy(2-(1-methyl-1H-pyrazol-5-yl)phenyl)methyl)-N-(thiazol-2-yl)benzenesulfonamide, 143) 4-((4-chloro-2-(furan-3-yl)phenyl)(hydroxy)methyl)-N-(thiazol-2-yl)benzenesulfonamide, 144) 4-((4-chloro-2-(1-methyl-1H-pyrazol-5-yl)phenyl)(hydroxy)methyl)-3-fluoro-N-(thiazol-2-yl)benzenesulfonamide, 145) 4-((4-chloro-2-(pyridin-3-yl)phenyl)(hydroxy)methyl)-3-fluoro-N-(thiazol-2-yl)benzenesulfonamide, 146) 4-((4-chloro-2-(pyridin-4-yl)phenyl)(hydroxy)methyl)-3-fluoro-N-(thiazol-2-yl)benzenesulfonamide, 147) 4-((4-chloro-2-(pyridin-4-yl)phenyl)(hydroxy)methyl)-N-(thiazol-2-yl)benzenesulfonamide, 148) 4-((4-chloro-2-(pyridin-3-yl)phenyl)(hydroxy)methyl)-N-(thiazol-2-yl)benzenesulfonamide, 149) 4-((2,4-di(furan-3-yl)phenyl)(hydroxy)methyl)-N-(thiazol-2-yl)benzenesulfonamide, 150) 4-((4-(2-fluoropyridin-3-yl)-2-(furan-3-yl)phenyl)(hydroxy)methyl)-N-(thiazol-2-yl)benzenesulfonamide, 151) 4-((4-(6-fluoropyridin-3-yl)-2-(furan-3-yl)phenyl)(hydroxy)methyl)-N-(thiazol-2-yl)benzenesulfonamide, 152) 4-((2'-fluoro-3-(furan-3-yl)-[1,1'-biphenyl]-4-yl)(hydroxy)methyl)-N-(thiazol-2-yl)benzenesulfonamide, 153) 4-((3'-fluoro-3-(furan-3-yl)-[1,1'-biphenyl]-4-yl)(hydroxy)methyl)-N-(thiazol-2-yl)benzenesulfonamide, 154) 4-((4'-fluoro-3-(furan-3-yl)-[1,1'-biphenyl]-4-yl)(hydroxy)methyl)-N-(thiazol-2-yl)benzenesulfonamide, 155) 3-fluoro-4-((2-(furan-3-yl)pyridin-3-yl)(hydroxy)methyl)-N-(thiazol-2-yl)benzenesulfonamide, 156) 4-((2-(furan-3-yl)pyridin-3-yl)(hydroxy)methyl)-N-(thiazol-2-yl)benzenesulfonamide, and 157) 3-fluoro-4-(hydroxy(2-phenylpyridin-3-yl)methyl)-N-(thiazol-2-yl)benzenesulfonamide.

The present invention provides a method for preparing the compound represented by formula 1.

For example, the present invention provides a method for preparing a compound represented by formula 1 wherein Y is O, the method being as shown in the following reaction scheme 1:

[Reaction Scheme 1]

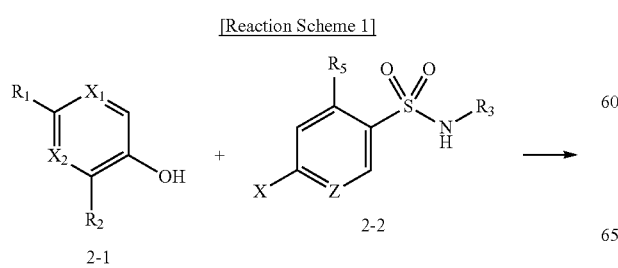

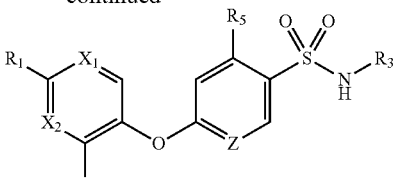

(wherein $R_1$, $R_2$, $R_3$, $R_5$, $X_1$, $X_2$ and Z are as defined above, and X is a halogen. Preferably, X is fluoro.)

In the above reaction, a compound represented by formula 2-1 is allowed to react with a compound represented by formula 2-2. The reaction is preferably carried out in the presence of $Cs_2CO_3$, and a solvent for the reaction is preferably DMF.

For example, the present invention also provides a method for preparing a compound represented by formula 1 wherein Y is CH(OH), the method being as shown in the following reaction scheme 2:

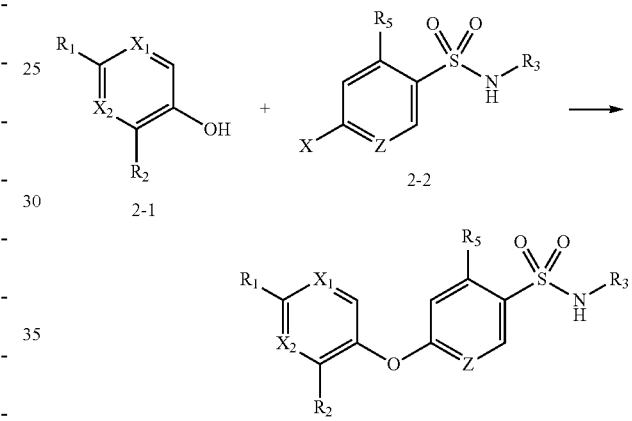

[Reaction scheme 2]

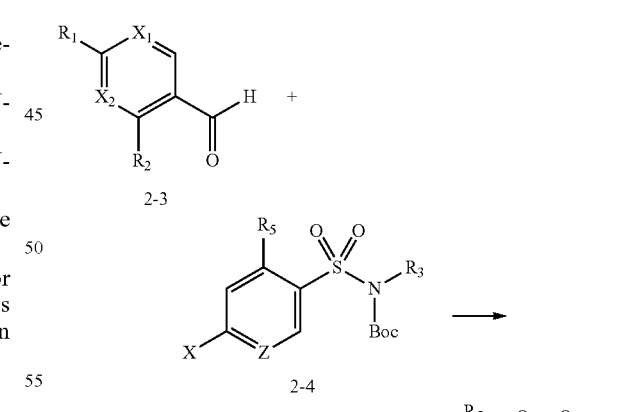

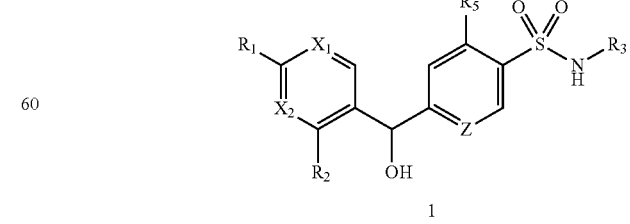

(wherein $R_1$, $R_2$, $R_3$, $R_5$, $X_1$, $X_2$ and Z are defined above, and X is a halogen. Preferably, X is chloro.)

In the reaction shown in reaction scheme 2, a compound represented by formula 2-3 is allowed to react with a compound represented by formula 2-4. The reaction is preferably carried out in the presence of n-BuLi, and a solvent for the reaction is preferably THF.

For example, the present invention also provides a method for preparing a compound represented by formula 1 wherein R1 is aryl or heteroaryl selected from the group consisting of phenyl, pyridinyl, pyrimidinyl, furanyl, isoxazolyl, pyrazolyl and thienyl (wherein the aryl or heteroaryl is unsubstituted or substituted by one or two substituents independently selected from the group consisting of $C_{1-4}$ alkyl, $C_{1-4}$ haloalkyl and halogen), the method being as shown in the following reaction scheme 3:

[Reaction Scheme 3]

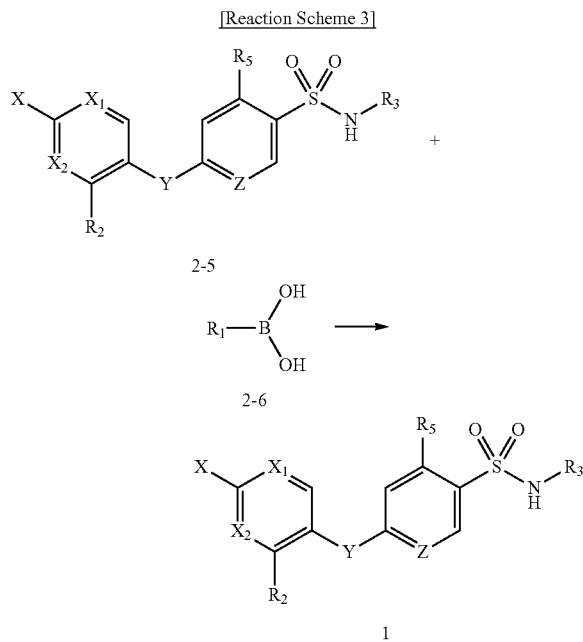

(wherein $R_2$, $R_3$, $R_5$, $X_1$, $X_2$, Y and Z are as defined above, and X is a halogen. Preferably, X is chloro.)

In the reaction shown in reaction scheme 3, a compound represented by formula 2-5 is allowed to react with a compound represented by formula 2-6. The reaction is preferably carried out in the presence of $Pd(PPh_3)_4$ and $Na_2CO_3$, and a solvent for the reaction is preferably DMF.

In addition, a pharmaceutically acceptable metal salt of the compound represented by formula 1 can be obtained using a base according to a conventional method. For example, a pharmaceutically acceptable metal salt of the compound represented by formula 1 can be obtained by dissolving the compound of formula 1 in an excess of an alkali metal hydroxide or alkaline earth metal hydroxide solution, filtering out undissolved compound salt, and evaporating and drying the filtrate. Herein, the metal salt prepared is particularly preferably a sodium, potassium or calcium salt, and this metal salt may be reacted with a suitable salt (e.g., nitrate).

A pharmaceutically unacceptable salt or solvate of the compound represented by formula 1 may be used as an intermediate in the preparation of the compound represented by formula 1 or a pharmaceutically acceptable salt or solvate thereof.

The inventive compounds represented by formula 1 include, in addition to pharmaceutically acceptable salts thereof, possible solvates and hydrates that can be prepared therefrom, as well as all possible stereoisomers. Solvates, hydrates and stereoisomers of the compounds represented by formula 1 can be prepared from the compounds of formula 1 using conventional methods.

In addition, the inventive compound represented by formula 1 may be prepared in a crystalline or amorphous form. When the compound represented by formula 1 is prepared in a crystalline form, it may optionally be hydrated or solvated. The present invention includes within its scope stoichiometric hydrates of the compounds represented by formula 1 as well as compounds containing variable amounts of water. Solvates of the inventive compounds represented by formula 1 include all stoichiometric solvates and non-stoichiometric solvates.

The present invention provides a pharmaceutical composition for preventing or treating a sodium channel blocker-related disease comprising the compound represented by formula 1 or a pharmaceutically acceptable salt, hydrate, solvate or isomer thereof as an active ingredient. Further, the present invention provides a method of treating or preventing a sodium channel blocker-related disease, which comprises administering to a subject in need thereof a pharmaceutical composition comprising comprising the compound represented by formula 1 or a pharmaceutically acceptable salt, hydrate, solvate or isomer thereof as an active ingredient. Further, the present invention provides a pharmaceutical composition for use in the prevention or treatment of a sodium channel blocker-related disease, comprising comprising the compound represented by formula 1 or a pharmaceutically acceptable salt, hydrate, solvate or isomer thereof as an active ingredient. Further, the present invention provides a use of a pharmaceutical composition comprising comprising the compound represented by formula 1 or a pharmaceutically acceptable salt, hydrate, solvate or isomer thereof as an active ingredient, for the manufacture of a medicament for preventing or treating a sodium channel blocker-related disease.

Herein, the diseases include acute pain, chronic pain, neuropathic pain, post-surgery pain, migraine, arthralgia, neuropathy, nerve injury, diabetic neuropathy, neuropathic disease, epilepsy, arrhythmia, myotonia, ataxia, multiple sclerosis, irritable bowel syndrome, urinary incontinence, visceral pain, depression, erythromelalgia, paroxysmal extreme pain disorder (PEPD), and the like.

The pharmaceutical composition of the present invention may be formulated in oral or parenteral dosage forms according to standard pharmaceutical standards. These formulations may contain, in addition to the active ingredient, additives such as a pharmaceutically acceptable carrier, adjuvant or diluent. Examples of suitable carriers include, but are not limited to, physiological saline, polyethylene glycol, ethanol, vegetable oil and isopropyl myristate, and examples of suitable diluents include, but are not limited to, lactose, dextrose, sucrose, mannitol, sorbitol, cellulose and/or glycine. In addition, the compounds of the present invention may be dissolved in oil, propylene glycol or other solvents, which are generally used in the preparation of injectable solutions. Further, the compounds of the present invention may be formulated into ointments or cream for topical application.

Hereinafter, formulation methods and excipients will be described, but the scope of the present invention is not limited to these examples.

The compounds of the present invention may be used in the form of pharmaceutically acceptable salts or solvates and may also be used alone or in appropriate association, as well as in combination with other pharmaceutically active compounds.

The compounds of the present invention may be formulated into injections by dissolving, suspending or emulsifying water-soluble solvent such as saline or 5% dextrose, or in water-insoluble solvents such as vegetable oils, synthetic fatty acid glyceride, higher fatty acid esters or propylene glycol. The formulations of the present invention may include any of conventional additives such as dissolving agents, isotonic agents, suspending agents, emulsifiers, stabilizers and preservatives.

The preferred dose of the compound of the present invention varies depending on the patient's condition and weight, the severity of the disease, the form of drug, and the route and duration of administration and may be suitably selected by those skilled in the art. To achieve the desired effects, however, the compound of the present invention may be administered at a daily dose of 0.0001-100 mg/kg (weight), and preferably 0.001-100 mg/kg (weight). The compound of the present invention may be administered by an oral or parenteral route in a single dose in a single dose or multiple doses daily.

The composition of the present invention may contain the compound of the present invention in an amount of 0.001-99 wt %, and preferably 0.01-60 wt %, depending on the mode of administration.

The pharmaceutical composition of the present invention may be administered to mammals, including rats, mice, humans, domestic animals and the like, by various routes. All routes of administration can be contemplated, and for example, the composition may be administered orally, intrarectally or by intravenous, intramuscular, subcutaneous, intrauterine, intrathecal or intracerebroventricular injection.

Advantageous Effects

As described above, the inventive compound represented by formula 1 or a pharmaceutically acceptable salt, hydrate, solvate or isomer thereof can be effectively used for the prevention or treatment of pain, for example, acute pain, chronic pain, neuropathic pain, post-surgery pain, migraine, arthralgia, neuropathy, nerve injury, diabetic neuropathy, neuropathic disease, epilepsy, arrhythmia, myotonia, ataxia, multiple sclerosis, irritable bowel syndrome, urinary incontinence, visceral pain, depression, erythromelalgia, or paroxysmal extreme pain disorder (PEPD).

MODE FOR INVENTION

Hereinafter, the present invention will be described in further detail with reference to preparation examples and examples. It is to be understood, however, that these preparation examples and examples are for illustrative purposes and are not intended to limit the scope of the present invention.

Example 1

Preparation of 3-cyano-4-(4-(furan-3-yl)-6-phenylpyridin-3-yloxy)-N-(thiazol-2-yl)benzenesolfonamide

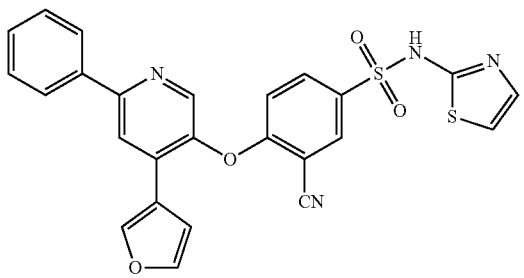 [SMILES: N#Cc1cc(S(=O)(=O)Nc2nccs2)ccc1Oc1cnc(-c2ccccc2)cc1-c1ccoc1]

10 mg (0.04 mmol) of 4-(furan-3-yl)-6-phenylpyridin-3-ol was dissolved in 1.5 mL of N,N-dimethylformamide, and 27 mg (0.08 mmol) of $Cs_2CO_3$ was added thereto, followed by stirring at room temperature for 10 minutes. Then, 15 mg (0.04 mmol) of 3-cyano-4-fluoro-N-(thiazol-2-yl)benzenesulfonamide was added thereto, and the solution was stirred at room temperature for 3 hours. After completion of the reaction as checked by TLC, the solvent was removed, and the remaining material was diluted with ethyl acetate and washed with saturated sodium chloride. The organic layer was collected, dried with magnesium sulfate to remove water, and concentrated under reduced pressure, and the residue was purified by column chromatography (developing solvent: ethyl acetate=100%) to obtain 16.0 mg (80% yield) of the title compound.

$^1$H NMR (CDCl$_3$, 500 MHz) δ 8.48 (1H), 7.98 (3H), 7.93 (1H), 7.91 (1H), 7.51 (3H), 7.46 (1H), 7.13 (1H), 6.82 (2H), 6.59 (1H)

Example 2

Preparation of 3-cyano-4-((4-(1-methyl-1H-pyrazol-5-yl)-6-phenylpyridin-3-yloxy)-N-(thiazol-2-yl)benzenesulfonamide

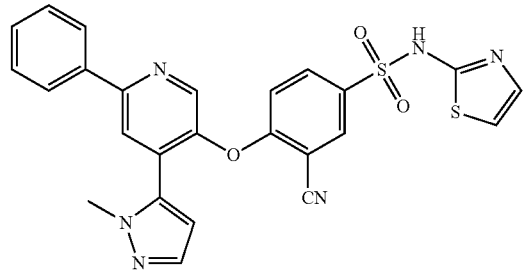 [SMILES: Cn1nccc1-c1cc(-c2ccccc2)ncc1Oc1ccc(S(=O)(=O)Nc2nccs2)cc1C#N]

10 mg (0.04 mmol) of 4-(1-methyl-1H-pyrazol-5-yl)-6-phenylpyridin-3-ol was dissolved in 1.5 mL of N,N-dimethylformamide, and 26 mg (0.08 mmol) of $Cs_2CO_3$ was added thereto, followed by stirring at room temperature for 10 minutes. Then, 15 mg (0.04 mmol) of 3-cyano-4-fluoro-N-(thiazol-2-yl)benzenesulfonamide was added thereto, and the solution was stirred at room temperature for 3 hours. After completion of the reaction as checked by TLC, the solvent was removed, and the remaining material was diluted with ethyl acetate and washed with saturated sodium chloride. The organic layer was collected, dried with magnesium sulfate to remove water, and concentrated under reduced pressure, and the residue was purified by column chromatography (developing solvent: ethyl acetate=100%) to obtain 17.1 mg (83% yield) of the title compound.

$^1$H NMR (CDCl$_3$, 500 MHz) δ 8.61 (1H), 8.13 (1H), 8.01 (2H), 7.92 (1H), 7.81 (1H), 7.66 (1H), 7.48 (3H), 7.12 (1H), 6.73 (1H), 6.59 (1H), 6.35 (1H), 3.93 (3H)

Example 3

Preparation of 3-cyano-4-(4-(furan-3-yl)-6-phenylpyridin-3-yloxy)-N-(1,2,4-thiadiazol-5-yl)benzenesulfonamide

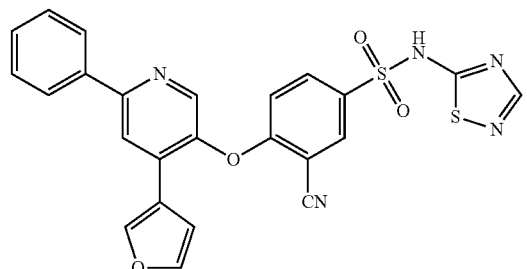

17.6 mg (88% yield) of the title compound was obtained in the same manner as described in Example 1, except that 3-cyano-4-fluoro-N-(1,2,4-thiadiazol-5-yl)benzenesulfonamide was used instead of 3-cyano-4-fluoro-N-(thiazol-2-yl)benzenesulfonamide.

¹H NMR (CDCl₃, 500 MHz) δ 8.49 (1H), 8.23 (1H), 8.16 (1H), 8.11 (1H), 8.07 (2H), 7.99 (2H), 7.60 (1H), 7.51 (2H), 7.46 (1H), 7.01 (1H), 6.92 (1H)

Example 4

Preparation of 3-cyano-4-((4-(1-methyl-1H-pyrazol-5-yl)-6-phenylpyridin-3-yl)oxy)-N-(1,2,4-thiadiazol-5-yl)benzenesulfonamide

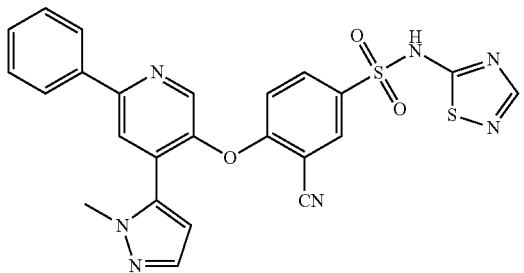 [SMILES: Cn1nccc1-c1cc(-c2ccccc2)ncc1Oc1ccc(S(=O)(=O)Nc2ncns2)cc1C#N]

16.7 mg (81% yield) of the title compound was obtained in the same manner as described in Example 2, except that 3-cyano-4-fluoro-N-(1,2,4-thiadiazol-5-yl)benzenesulfonamide was used instead of 3-cyano-4-fluoro-N-(thiazol-2-yl)benzenesulfonamide.

¹H NMR (CDCl₃, 500 MHz) δ 8.71 (1H), 8.10 (3H), 8.08 (1H), 7.97 (1H), 7.94 (1H), 7.51 (2H), 7.48 (1H), 7.38 (1H), 6.93 (1H), 6.37 (1H), 3.89 (3H)

Example 5

Preparation of 3-cyano-4-(6-(3-fluorophenyl)-4-(furan-3-yl)pyridin-3-yloxy)-N-(thiazol-2-yl)benzenesulfonamide

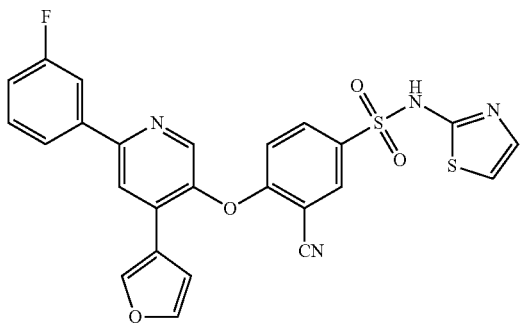 [SMILES: N#Cc1cc(S(=O)(=O)Nc2nccs2)ccc1Oc1cnc(-c2cccc(F)c2)cc1-c1ccoc1]

100 mg (0.22 mmol) of 4-((6-chloro-4-(furan-3-yl)pyridin-3-yl)oxy)-3-cyano-N-(thiazol-2-yl)benzenesulfonamide was dissolved in 2.4 mL of 1,4-dioxane, and 33.6 mg (0.24 mmol) of (3-fluorophenyl)boronic acid was added thereto, and then 8.3 mg (3 mol %) of Pd(PPh₃)₄, 76.2 mg (0.72 mmol) of Na₂CO₃, and 2.4 mL of H₂O were added thereto. After reacting with microwave reactor at 120° C. for 5 minutes, the solvent was removed, and the remaining material was diluted with ethyl acetate and the organic layer was separated, and washed with saturated sodium chloride. The organic layer was collected, dried with magnesium sulfate to remove water, and concentrated under reduced pressure, and the residue was purified by column chromatography (developing solvent, hexane:ethyl acetate=1:1) to obtain 80 mg (70% yield) of the title compound.

¹H NMR (CDCl₃, 500 MHz) δ 8.51 (s, 1H), 8.23 (s, 1H), 8.06 (s, 1H), 7.96 (d 1H), 7.92 (s, 1H), 7.79 (d, 1H), 7.73 (d, 1H), 7.54 (s, 1H), 7.49 (m, 1H), 7.18 (m, 1H), 7.11 (s, 1H), 6.90 (d, 1H), 6.86 (s, 1H), 6.58 (s, 1H)

Example 6

Preparation of 3-cyano-4-(6-(2-fluorophenyl)-4-(furan-3-yl)pyridin-3-yloxy)-N-(thiazol-2-yl)benzenesulfonamide

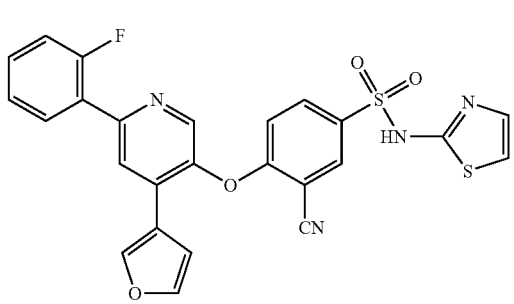 [SMILES: N#Cc1cc(S(=O)(=O)Nc2nccs2)ccc1Oc1cnc(-c2ccccc2F)cc1-c1ccoc1]

68 mg (60% yield) of the title compound was obtained in the same manner as described in Example 5, except that (2-fluorophenyl)boronic acid was used instead of (3-fluorophenyl)boronic acid.

¹H NMR (CD₃OD/CDCl₃, 500 MHz) δ 8.22 (s, 1H), 7.98 (s, 1H), 7.87 (s, 2H), 7.74 (d, 1H), 7.53 (t, 1H), 7.29 (s, 1H), 7.22 (m, 1H), 7.05 (t, 1H), 7.98 (t, 1H), 6.73 (d, 1H), 6.70 (d, 1H), 6.64 (s, 1H), 6.34 (d, 1H)

Example 7

Preparation of 3-cyano-4-(6-(4-fluorophenyl)-4-(furan-3-yl)pyridin-3-yloxy)-N-(thiazol-2-yl)benzenesulfonamide

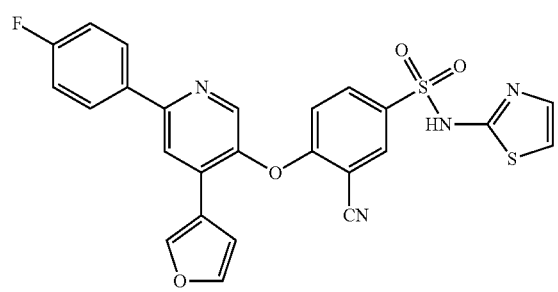 [SMILES: N#Cc1cc(S(=O)(=O)Nc2nccs2)ccc1Oc1cnc(-c2ccc(F)cc2)cc1-c1ccoc1]

74 mg (65% yield) of the title compound was obtained in the same manner as described in Example 5, except that (4-fluorophenyl)boronic acid was used instead of (3-fluorophenyl)boronic acid.

¹H NMR (CD₃OD/CDCl₃, 500 MHz) δ 8.19 (s, 1H), 7.99 (s, 1H), 7.92 (d, 2H), 7.75 (d, 2H), 7.50 (d, 1H), 7.68 (m, 2H), 6.98 (t, 1H), 6.73 (m, 3H), 6.35 (d, 1H)

Example 8

Preparation of 3-cyano-4-(4-(furan-3-yl)-6-(3-(trifluoromethyl)phenyl)pyridin-3-yloxy)-N-(thiazol-2-yl)benzenesulfonamide

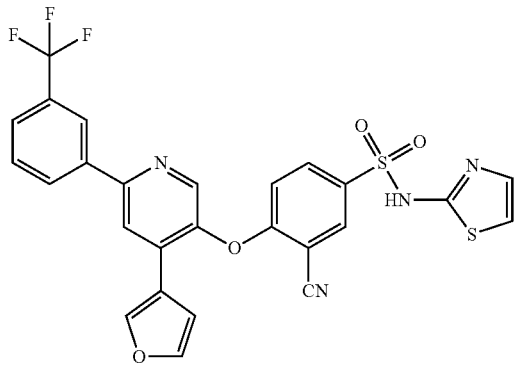 [SMILES: N#Cc1cc(S(=O)(=O)Nc2nccs2)ccc1Oc1cnc(-c2cccc(C(F)(F)F)c2)cc1-c1ccoc1]

63 mg (50% yield) of the title compound was obtained in the same manner as described in Example 5, except that (3-(trifluoromethyl)phenyl)boronic acid was used instead of (3-fluorophenyl)boronic acid.

$^1$H NMR (CDCl$_3$, 500 MHz) δ 8.49 (s, 1H), 8.28 (s, 1H), 8.22 (m, 2H), 8.08 (s, 1H), 7.97 (s, 1H), 7.94 (d, 1H), 7.73 (d, 1H), 7.60 (m, 1H), 7.01 (d, 1H), 6.88 (s, 1H), 6.85 (d, 1H), 6.53 (d, 1H)

Example 9

Preparation of 3-cyano-4-(2'-fluoro-4-(furan-3-yl)-2,4'-bipyridin-5-yloxy)-N-(thiazol-2-yl)benzenesulfonamide

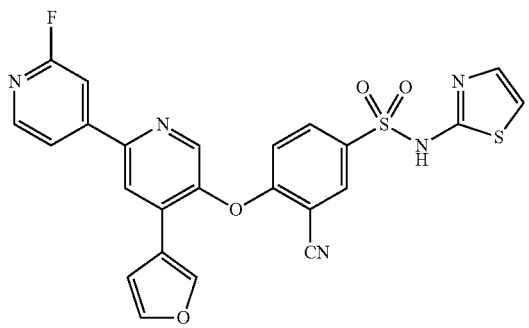 [SMILES: N#Cc1cc(S(=O)(=O)Nc2nccs2)ccc1Oc1cnc(-c2ccnc(F)c2)cc1-c1ccoc1]

74 mg (65% yield) of the title compound was obtained in the same manner as described in Example 5, except that (2-fluoropyridin-4-yl)boronic acid was used instead of (3-fluorophenyl)boronic acid.

$^1$H NMR (CD$_3$OD/CDCl$_3$, 500 MHz) δ 8.19 (s, 1H), 8.00 (d, 1H), 7.95 (s, 1H), 7.90 (s, 1H), 7.78 (s, 1H), 7.68 (d, 1H), 7.63 (d, 1H), 7.40 (s, 1H), 6.70 (d, 1H), 6.66 (s, 1H), 6.58 (d, 1H), 6.33 (d, 1H)

Example 10

Preparation of 3-cyano-4-(2'-fluoro-4-(furan-3-yl)-2,3'-bipyridin-5-yloxy)-N-(thiazol-2-yl)benzenesulfonamide

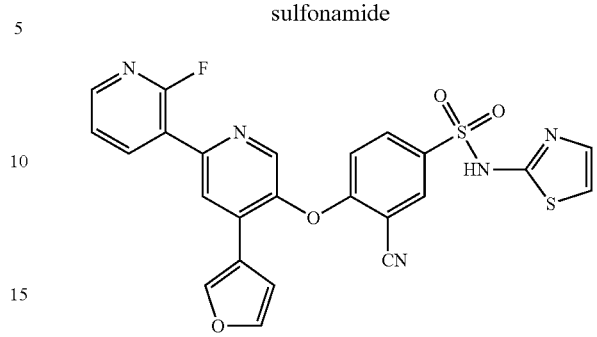

63 mg (55% yield) of the title compound was obtained in the same manner as described in Example 5, except that (2-fluoropyridin-3-yl)boronic acid was used instead of (3-fluorophenyl)boronic acid.

$^1$H NMR (CDCl$_3$, 500 MHz) δ 8.59 (t, 1H), 8.50 (s, 1H), 8.32 (d, 1H), 8.26 (d, 1H), 8.06 (s, 1H), 8.99 (d, 1H), 7.53 (s, 1H), 7.40 (t, 1H), 7.10 (d, 1H), 6.87 (d, 1H), 6.86 (s, 1H), 6.59 (d, 1H)

Example 11

Preparation of 3-cyano-4-(6'-fluoro-4-(furan-3-yl)-2,3'-bipyridin-5-yloxy)-N-(thiazol-2-yl)benzenesulfonamide

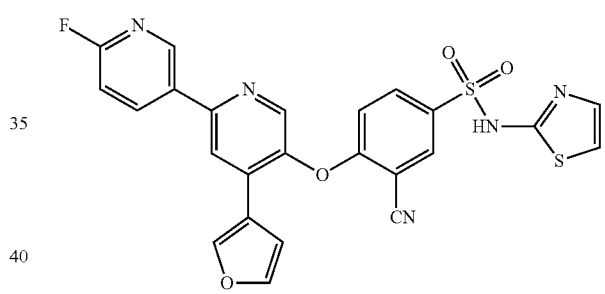

69 mg (60% yield) of the title compound was obtained in the same manner as described in Example 5, except that (6-fluoropyridin-3-yl)boronic acid was used instead of (3-fluorophenyl)boronic acid.

$^1$H NMR (CDCl$_3$, 500 MHz) δ 8.84 (s, 1H), 8.51 (t, 1H), 8.48 (s, 1H), 8.24 (s, 1H), 8.06 (s, 1H), 7.97 (d, 1H), 7.92 (s, 1H), 7.54 (s, 1H), 7.09 (m, 2H), 6.87 (m, 2H), 6.59 (d, 1H)

Example 12

Preparation of 3-cyano-4-(2',6'-difluoro-4-(furan-3-yl)-2,3'-bipyridin-5-yloxy)-N-(thiazol-2-yl)benzenesulfonamide

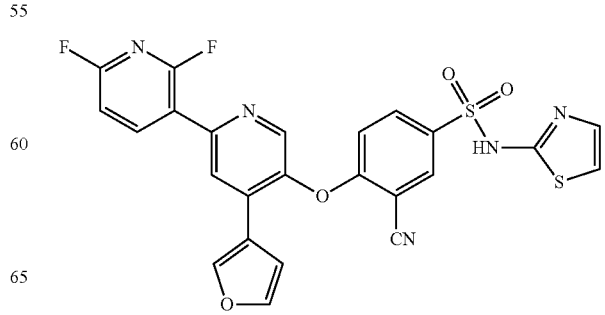

59 mg (50% yield) of the title compound was obtained in the same manner as described in Example 5, except that (2,6-difluoropyridin-3-yl)boronic acid was used instead of (3-fluorophenyl)boronic acid.

$^1$H NMR (CDCl$_3$, 500 MHz) δ 8.73 (q, 1H), 8.48 (s, 1H), 8.25 (d, 1H), 8.11 (s, 1H), 8.06 (s, 1H), 7.99 (dd, 1H), 7.67 (m, 1H), 7.11 (d, 1H), 7.04 (dd, 1H), 6.88 (d, 1H), 6.85 (s, 1H), 6.60 (d, 1H)

Example 13

Preparation of 3-cyano-4-(4-(furan-3-yl)-2,3'-bipyridin-5-yloxy)-N-(thiazol-2-yl)benzenesulfonamide

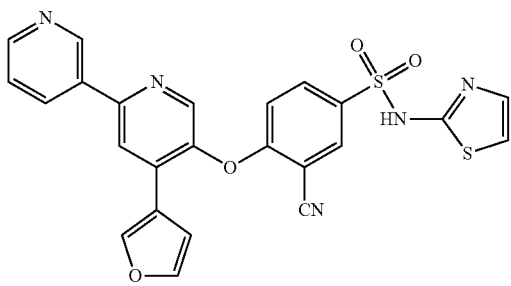 [SMILES: N#Cc1cc(S(=O)(=O)Nc2nccs2)ccc1Oc1cnc(-c2cccnc2)cc1-c1ccoc1]

66 mg (60% yield) of the title compound was obtained in the same manner as described in Example 5, except that pyridin-3-ylboronic acid was used instead of (3-fluorophenyl)boronic acid.

$^1$H NMR (CD$_3$OD/CDCl$_3$, 500 MHz) δ 9.67 (s, 1H), 9.20 (d, 1H), 8.79 (d, 1H), 8.42 (s, 1H), 8.34 (s, 1H), 8.21 (s, 1H), 8.08 (s, 1H), 8.05 (d, 1H), 7.94 (d, 1H), 7.47 (s, 1H), 6.98 (s, 1H), 6.88 (s, 1H), 6.79 (d, 1H), 6.48 (d, 1H)

Example 14

Preparation of 3-cyano-4-(4-(furan-3-yl)-2,4'-bipyridin-5-yloxy)-N-(thiazol-2-yl)benzenesulfonamide

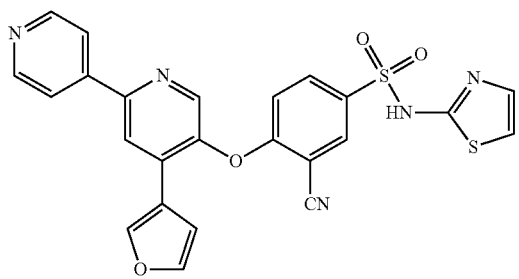 [SMILES: N#Cc1cc(S(=O)(=O)Nc2nccs2)ccc1Oc1cnc(-c2ccncc2)cc1-c1ccoc1]

61 mg (55% yield) of the title compound was obtained in the same manner as described in Example 5, except that pyridin-4-ylboronic acid was used instead of (3-fluorophenyl)boronic acid.

$^1$H NMR (CD$_3$OD/CDCl$_3$, 500 MHz) δ δ 8.76 (d, 2H), 8.57 (s, 1H), 8.43 (s, 1H), 8.37 (d, 2H), 8.29 (d, 1H), 8.17 (s, 1H), 8.03 (d, 1H), 7.62 (s, 1H), 7.10 (d, 1H), 7.07 (s, 1H), 7.00 (d, 1H), 6.73 (d, 1H)

Example 15

Preparation of 3-cyano-4-(4-(furan-3-yl)-6-(pyrimidin-5-yl)pyridin-3-yloxy)-N-(thiazol-2-yl)benzenesulfonamide

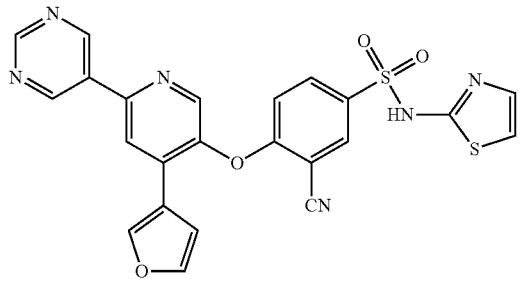 [SMILES: N#Cc1cc(S(=O)(=O)Nc2nccs2)ccc1Oc1cnc(-c2cncnc2)cc1-c1ccoc1]

66 mg (60% yield) of the title compound was obtained in the same manner as described in Example 5, except that (pyrimidin-5-yl)boronic acid was used instead of (3-fluorophenyl)boronic acid.

$^1$H NMR (CD$_3$OD/CDCl$_3$, 500 MHz) δ 9.38 (s, 2H), 9.22 (s, 1H), 8.43 (s, 1H), 8.20 (s, 1H), 8.00 (s, 2H), 7.92 (m, 1H), 7.46 (s, 1H), 6.87 (s, 2H), 6.84 (s, 1H), 6.76 (m, 1H), 6.48 (s, 1H)

Example 16

Preparation of 3-cyano-4-((4,6-di(furan-3-yl)pyridin-3-yl)oxy)-N-(thiazol-2-yl)benzenesulfonamide

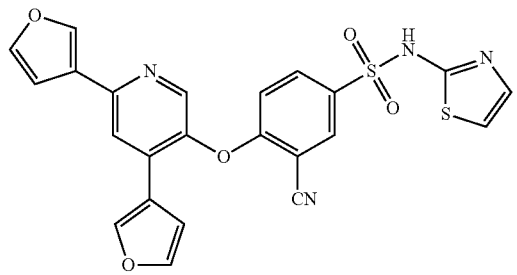 [SMILES: N#Cc1cc(S(=O)(=O)Nc2nccs2)ccc1Oc1cnc(-c2ccoc2)cc1-c1ccoc1]

20.0 mg of 4,6-di(furan-3-yl)pyridin-3-ol and 24.9 mg of 3-cyano-4-fluoro-N-(thiazol-2-yl)benzenesulfonamide were dissolved in DMF, and 86.0 mg (3.0 eq) of Cs$_2$CO$_3$ (86.0 mg, 3.0 eq) was added thereto. After reacting at room temperature for 2 hours, the resulting mixture was reacted at 60° C. for 16 hours. The solvent was removed by concentrating under reduced pressure. AS work-up with EA/H$_2$O, the ethyl acetate layer was treated with magnesium sulfate, and concentrated under reduced pressure. The residue was separated by PLC (developing solvent, EA:n-Hex=1:4) to obtain 10.1 mg (24% yield) of the title compound.

$^1$H NMR (CD$_3$OD/CDCl$_3$, 500 MHz) δ 8.39 (s, 1H), 8.24 (s, 2H), 8.09 (s, 1H), 8.00 (s, 1H), 7.96 (s, 1H), 7.63 (s, 1H), 7.60 (s, 1H), 7.10 (d, 1H), 7.07 (s, 1H), 7.01 (s, 1H), 6.89 (m, 1H), 6.71 (s, 1H)

Example 17

Preparation of 4-((4,6-di(furan-3-yl)pyridin-3-yl)oxy)-3-fluoro-N-(thiazol-2-yl)benzenesulfonamide

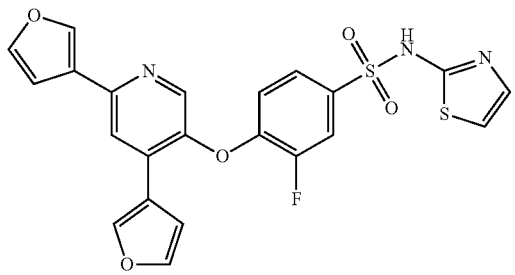 [SMILES: O=S(=O)(Nc1nccs1)c1ccc(Oc2cnc(-c3ccoc3)cc2-c2ccoc2)c(F)c1]

7.8 mg (18% yield) of the title compound was obtained in the same manner as described in Example 16, except that N-(tert-butyl)-3,4-fluoro-N-(thiazol-2-yl)benzenesulfonamide was used instead of 3-cyano-4-fluoro-N-(thiazol-2-yl)benzenesulfonamide.

$^1$H NMR (CDCl$_3$, 500 MHz) δ 8.41 (s, 1H), 8.21 (s, 1H), 8.18 (s, 1H), 7.81 (d, 1H), 7.76 (s, 1H), 7.69 (d, 1H), 7.58 (s, 1H), 7.54 (s, 1H), 7.18 (m, 1H), 7.12 (d, 1H), 7.06 (s, 1H), 6.90 (s, 1H), 6.58 (d, 1H)

Example 18

Preparation of 3-cyano-4-((2'-fluoro-4-(1-methyl-1H-pyrazol-5-yl)-[2,3'-bipyridin]-5-yl)oxy)-N-(thiazol-2-yl)benzenesulfonamide

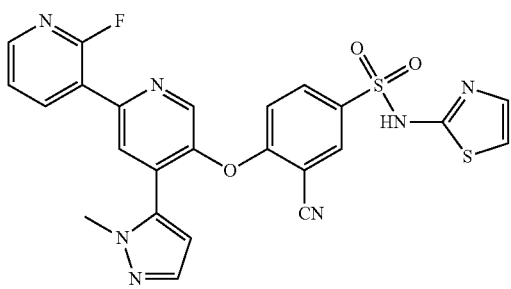 [SMILES: Cn1nccc1-c1cc(-c2cccnc2F)ncc1Oc1ccc(S(=O)(=O)Nc2nccs2)cc1C#N]

10 mg of 4-((6-chloro-4-(1-methyl-1H-pyrazol-5-yl)pyridin-3-yl)oxy)-3-cyano-N-(thiazol-2-yl)benzenesulfonamide was dissolved in DMF/H$_2$O=1:1 (0.46 mL), and 3.2 mg of (2-fluoropyridin-3-yl)boronic acid, 0.8 mg of Pd(PPh$_3$)$_4$ and 7.4 mg of Na$_2$CO$_3$ were added thereto. After reacting with microwave reactor at 120° C. for 5 minutes, DMF was removed by concentrating under reduced pressure. After extracting with EA, the extract was treated with MgSO$_4$ and concentrated under reduced pressure. The residue was separated by PLC (developing solvent, EA) to obtain 3.2 mg (28% yield) of the title compound.

$^1$H NMR (CD$_3$OD, 500 MHz) δ 8.79 (s, 1H), 8.63 (t, 1H), 8.31 (d, 1H), 8.14 (d, 1H), 8.07 (s, 1H), 7.98 (dd, 1H), 7.52 (t, 1H), 7.39 (d, 1H), 7.14 (d, 1H), 7.00 (d, 1H), 6.76 (d, 1H), 6.41 (d, 1H), 3.89 (s, 3H)

Example 19

Preparation of 3-cyano-4-((6'-fluoro-4-(1-methyl-1H-pyrazol-5-yl)-[2,3'-bipyridin]-5-yl)oxy)-N-(thiazol-2-yl)benzenesulfonamide

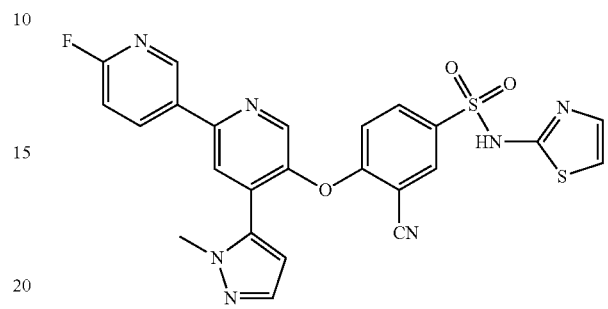

4.2 mg (37% yield) of the title compound was obtained in the same manner as described in Example 18, except that (6-fluoropyridin-3-yl)boronic acid was used instead of (2-fluoropyridin-3-yl)boronic acid.

$^1$H NMR (CD$_3$OD, 500 MHz) δ 8.95 (s, 1H), 8.75 (s, 1H), 8.67 (t, 1H), 8.13 (s, 1H), 7.96 (m, 2H), 7.39 (s, 1H), 7.22 (d, 1H), 7.14 (d, 1H), 6.98 (d, 1H), 6.76 (d, 1H), 6.40 (d, 1H), 3.88 (s, 3H)

Example 20

Preparation of 3-cyano-4-((4-(furan-3-yl)-6-(thiophen-3-yl)pyridin-3-yl)oxy)-N-(thiazol-2-yl)benzenesulfonamide

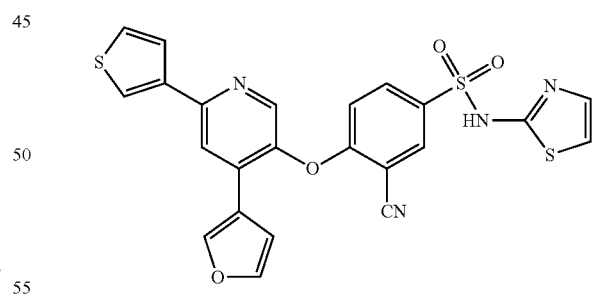

34 mg (31% yield) of the title compound was obtained in the same manner as described in Example 5, except that (thiophen-3-yl)boronic acid was used instead of (3-fluorophenyl)boronic acid.

$^1$H NMR (CD$_3$OD, 500 MHz) δ 8.43 (s, 1H), 8.26 (s, 1H), 8.13 (s, 2H), 8.10 (s, 1H), 8.00 (dd, 1H), 7.79 (d, 1H), 7.61 (s, 1H), 7.54 (dd, 1H), 7.12 (d, 1H), 7.02 (s, 1H), 6.94 (d, 1H), 6.75 (d, 1H)

Example 21

Preparation of 3-fluoro-4-((4-(1-methyl-1H-pyrazol-5-yl)-[2,3'-bipyridin]-5-yl)oxy)-N-(thiazol-2-yl)benzenesulfonamide

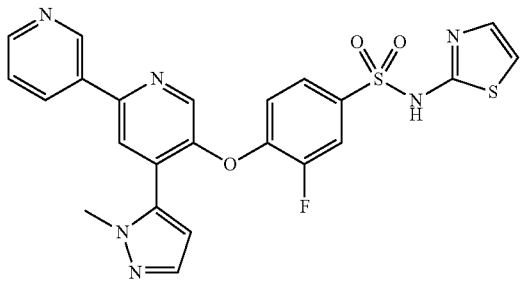 [SMILES: Cn1nccc1-c1cc(-c2cccnc2)ncc1Oc1ccc(S(=O)(=O)Nc2nccs2)cc1F]

10 mg (0.02 mmol) of 4-((6-chloro-4-(1-methyl-1H-pyrazol-5-yl)pyridin-3-yl)oxy)-3-fluoro-N-(thiazol-2-yl)benzenesulfonamide was dissolved in 3 mL of N,N-dimethylformamide, and 3.9 mg (0.03 mmol) of (pyridin-3-yl)boronic acid was added thereto, and then 2.4 mg (10 mol %) of Pd(PPh$_3$)$_4$, 6.8 mg (0.64 mmol) of Na$_2$CO$_3$, and 1 mL of H$_2$O were added thereto. After reacting with microwave reactor at 120° C. 10 minutes, the solvent was removed, and the remaining material was diluted with ethyl acetate and the organic layer was separated, and washed with saturated sodium chloride. The organic layer was collected, dried with magnesium sulfate to remove water, and concentrated under reduced pressure, and the residue was purified by column chromatography (developing solvent, hexane:ethyl acetate=3:1) to obtain 5 mg (45% yield) of the title compound.

$^1$H NMR (CD$_3$OD, 500 MHz) δ 9.23 (s, 1H), 8.80 (d, 1H), 8.60 (s, 1H), 8.53 (m, 1H), 8.10 (s, 1H), 7.70 (m, 1H), 7.67 (m, 1H), 7.62 (m, 1H), 7.43 (s, 1H), 7.13 (m, 2H), 6.76 (m, 1H), 6.45 (s, 1H), 3.87 (s, 3H)

Example 22

Preparation of 3-fluoro-4-((4-(1-methyl-1H-pyrazol-5-yl)-6-(thiophen-3-yl)pyridin-3-yl)oxy)-N-(thiazol-2-yl)benzenesulfonamide

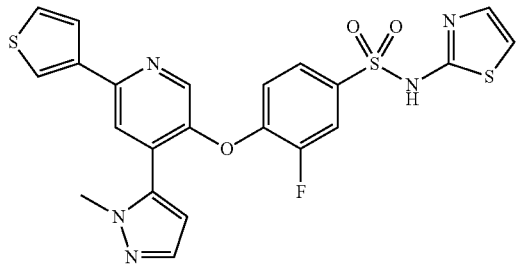 [SMILES: Cn1nccc1-c1cc(-c2ccsc2)ncc1Oc1ccc(S(=O)(=O)Nc2nccs2)cc1F]

5 mg (45% yield) of the title compound was obtained in the same manner as described in Example 21, except that (thiophen-3-yl)boronic acid was used instead of (pyridin-3-yl)boronic acid.

$^1$H NMR (CD$_3$OD/CDCl$_3$, 500 MHz) δ 8.45 (s, 1H), 8.23 (s, 1H), 8.09 (s, 1H), 7.92 (m, 1H), 7.59 (m, 4H), 7.40 (s, 1H), 7.12 (m, 1H), 7.03 (m, 1H), 6.76 (m, 1H), 6.40 (s, 1H), 3.85 (s, 3H)

Example 23

Preparation of 3-cyano-4-((6-(4-fluorophenyl)-4-(1-methyl-1H-pyrazol-5-yl)pyridin-3-yl)oxy)-N-(thiazol-2-yl)benzenesulfonamide

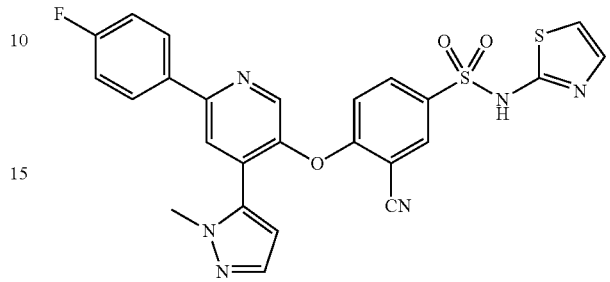

10 mg (0.02 mmol) of 4-((6-chloro-4-(1-methyl-1H-pyrazol-5-yl)pyridin-3-yl)oxy)-3-cyano-N-(thiazol-2-yl)benzenesulfonamide was dissolved in 3 mL of N,N-dimethylformamide, and 4.4 mg (0.03 mmol) of (4-fluorophenyl)boronic acid was added thereto, and then 2.4 mg (10 mol %) of Pd(PPh$_3$)$_4$, 6.7 mg (0.6 mmol) of Na$_2$CO$_3$, and 1 mL of H$_2$O were added thereto. After reacting with microwave reactor at 120° C. for 10 minutes, the solvent was removed, and the remaining material was diluted with ethyl acetate and the organic layer was separated, and washed with saturated sodium chloride. The organic layer was collected, dried with magnesium sulfate to remove water, and concentrated under reduced pressure, and the residue was purified by column chromatography (developing solvent, hexane:ethyl acetate=3:1) to obtain 5 mg (45% yield) of the title compound.

$^1$H NMR (CD$_3$OD, 500 MHz) δ 8.72 (s, 1H), 8.14 (m, 3H), 8.03 (s, 1H), 7.94 (m, 1H), 7.37 (d, 1H), 7.23 (m, 2H), 7.13 (m, 1H), 6.94 (m, 1H), 6.74 (d, 1H), 3.87 (s, 3H)

Example 24

Preparation of 3-cyano-4-((6-(2-fluorophenyl)-4-(1-methyl-1H-pyrazol-5-yl)pyridin-3-yl)oxy)-N-(thiazol-2-yl)benzenesulfonamide

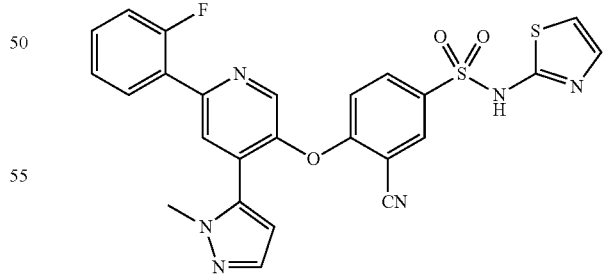

5 mg (45% yield) of the title compound was obtained in the same manner as described in Example 23, except that (pyridin-2-yl)boronic acid was used instead of (4-fluorophenyl)boronic acid.

$^1$H NMR (CD$_3$OD/CDCl$_3$, 500 MHz) δ 8.79 (s, 1H), 8.12 (s, 1H), 7.98 (m, 3H), 7.52 (m, 1H), 7.38 (m, 2H), 7.29 (m, 1H), 7.13 (m, 1H), 6.99 (m, 1H), 6.75 (d, 1H), 6.39 (s, 1H), 3.88 (s, 3H)

Example 25

Preparation of 3-cyano-4-((6-(furan-3-yl)-4-(1-methyl-1H-pyrazol-5-yl)pyridin-3-yl)oxy)-N-(thiazol-2-yl)benzenesulfonamide

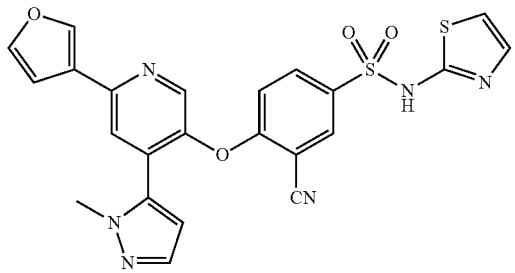 [SMILES: Cn1nccc1-c1cc(-c2ccoc2)ncc1Oc1ccc(S(=O)(=O)Nc2nccs2)cc1C#N]

5 mg (47% yield) of the title compound was obtained in the same manner as described in Example 23, except that (furan-3-yl)boronic acid was used instead of (4-fluorophenyl)boronic acid.

$^1$H NMR (CD$_3$OD/CDCl$_3$, 500 MHz) δ 8.61 (s, 1H), 8.23 (s, 1H), 8.11 (s, 1H), 7.93 (m, 1H), 7.84 (s, 1H), 7.62 (s, 1H), 7.36 (d, 1H), 7.13 (d, 1H), 7.05 (d, 1H), 6.92 (d, 1H), 6.75 (d, 1H), 6.35 (d, 1H), 3.86 (s, 3H)

Example 26

Preparation of 3-cyano-4-((6-(3-fluorophenyl)-4-(1-methyl-1H-pyrazol-5-yl)pyridin-3-yl)oxy)-N-(thiazol-2-yl)benzenesulfonamide

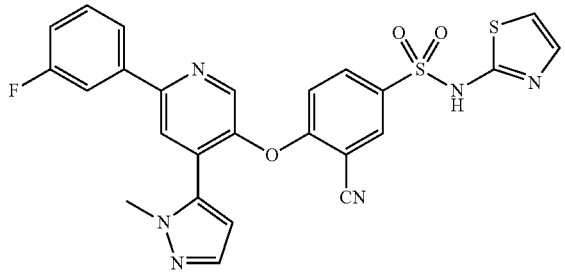 [SMILES: Cn1nccc1-c1cc(-c2cccc(F)c2)ncc1Oc1ccc(S(=O)(=O)Nc2nccs2)cc1C#N]

5 mg (45% yield) of the title compound was obtained in the same manner as described in Example 23, except that (pyridin-3-yl)boronic acid was used instead of (4-fluorophenyl)boronic acid.

$^1$H NMR (CD$_3$OD/CDCl$_3$, 500 MHz) δ 8.72 (s, 1H), 7.95 (d, 2H), 7.93 (m, 3H), 7.50 (m, 1H), 7.37 (s, 1H), 7.22 (m, 1H), 7.13 (m, 1H), 6.95 (d, 1H), 6.75 (d, 1H), 6.39 (s, 1H), 3.88 (s, 3H)

Example 27

Preparation of 3-cyano-4-((2'-fluoro-4-(1-methyl-1H-pyrazol-5-yl)-[2,4'-bipyridin]-5-yl)oxy)-N-(thiazol-2-yl)benzenesulfonamide

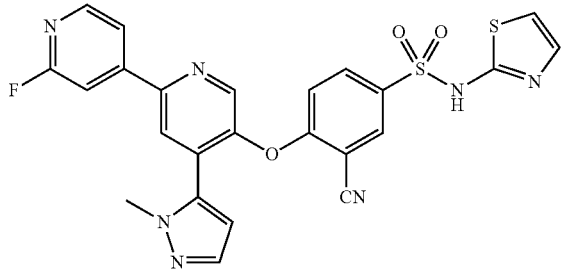 [SMILES: Cn1nccc1-c1cc(-c2ccnc(F)c2)ncc1Oc1ccc(S(=O)(=O)Nc2nccs2)cc1C#N]

5 mg (44% yield) of the title compound was obtained in the same manner as described in Example 23, except that (2-fluoropyridin-4-yl)boronic acid was used instead of (4-fluorophenyl)boronic acid.

$^1$H NMR (CD$_3$OD/CDCl$_3$, 500 MHz) δ 8.78 (s, 1H), 8.33 (m, 1H), 8.26 (s, 1H), 8.14 (d, 1H), 8.06 (m, 1H), 7.98 (m, 1H), 7.83 (s, 1H), 7.39 (m, 1H), 7.12 (d, 1H), 6.99 (d, 1H), 6.73 (m, 1H), 6.41 (d, 1H), 3.88 (s, 3H)

Example 28

Preparation of 4-((4,6-di(furan-3-yl)pyridin-3-yl)oxy)-N-(thiazol-2-yl)benzenesulfonamide

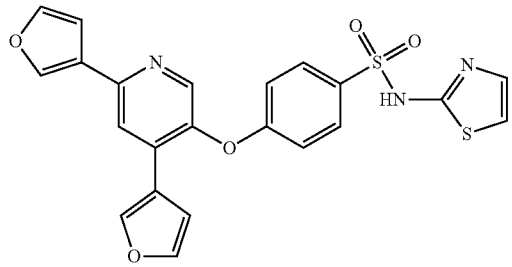 [SMILES: O=S(=O)(Nc1nccs1)c1ccc(Oc2cnc(-c3ccoc3)cc2-c2ccoc2)cc1]

2.8 mg (78% yield) of the title compound was obtained in the same manner as described in Example 16, except that N-(tert-butyl)-4-fluoro-N-(thiazol-2-yl)benzenesulfonamide was used instead of 3-cyano-4-fluoro-N-(thiazol-2-yl)benzenesulfonamide.

$^1$H NMR (CD$_3$OD, 500 MHz) δ 8.22 (s, 1H), 8.16 (s, 1H), 7.96 (s, 1H), 7.91 (s, 1H), 7.87 (d, 2H), 7.58 (s, 1H), 7.55 (s, 1H), 7.05 (m, 3H), 7.00 (dd, 2H), 6.66 (d, 1H)

Example 29

Preparation of 3-cyano-4-((2-fluoro-6'-phenyl-[3,4'-bipyridin]-3'-yl)oxy)-N-(thiazol-2-yl)benzenesulfonamide

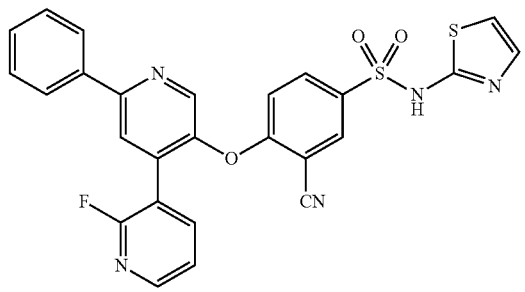 [SMILES: N#Cc1cc(S(=O)(=O)Nc2nccs2)ccc1Oc1cnc(-c2ccccc2)cc1-c1cccnc1F]

10 mg (0.02 mmol) of 3-cyano-4-((4-iodo-6-phenylpyridin-3-yl)oxy)-N-(thiazol-2-yl)benzenesulfonamide was dissolved in 3 mL of N,N-dimethylformamide, and 3.7 mg (0.03 mmol) of (2-fluoropyridin-3-yl)boronic acid was added thereto, and then 2.0 mg (10 mol %) of Pd(PPh$_3$)$_4$, 5.6 mg (0.6 mmol) of Na$_2$CO$_3$, and 1 mL of H$_2$O were added thereto. After reacting with microwave reactor at 120° C. for 5 minutes, the solvent was removed, and the remaining material was diluted with ethyl acetate and the organic layer was separated, and washed with saturated sodium chloride. The organic layer was collected, dried with magnesium sulfate to remove water, and concentrated under reduced pressure, and the residue was purified by column chromatography (developing solvent, hexane:ethyl acetate=3:1) to obtain 3 mg (30% yield) of the title compound.

$^1$H NMR (CD$_3$OD, 500 MHz) δ 8.61 (s, 1H), 8.08 (m, 3H), 8.04 (m, 1H), 7.84 (m, 2H), 7.52 (m, 4H), 7.15 (m, 1H), 6.77 (m, 2H), 6.64 (m, 1H)

Example 30

Preparation of 3-cyano-4-((6-fluoro-6'-phenyl-[3,4'-bipyridin]-3'-yl)oxy)-N-(thiazol-2-yl)benzenesulfonamide

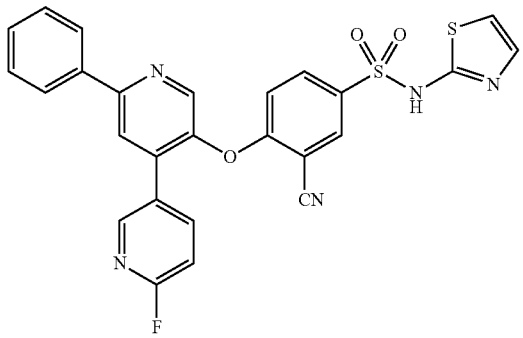 [SMILES: N#Cc1cc(S(=O)(=O)Nc2nccs2)ccc1Oc1cnc(-c2ccccc2)cc1-c1ccc(F)nc1]

3 mg (30% yield) of the title compound was obtained in the same manner as described in Example 29, except that (2-fluoropyridin-5-yl)boronic acid was used instead of (2-fluoropyridin-3-yl)boronic acid.

$^1$H NMR (CD$_3$OD/CDCl$_3$, 500 MHz) δ 8.52 (s, 1H), 8.35 (m, 1H), 8.15 (m, 1H), 8.05 (m, 2H), 7.99 (m, 1H), 7.92 (m, 1H), 7.86 (m, 1H), 7.52 (m, 2H), 7.45 (m, 1H), 7.11 (m, 1H), 6.86 (m, 1H), 6.72 (m, 1H), 6.64 (m, 1H)

Example 31

Preparation of 3-cyano-4-((2'-fluoro-6-phenyl-[4,4'-bipyridin]-3-yl)oxy)-N-(thiazol-2-yl)benzenesulfonamide

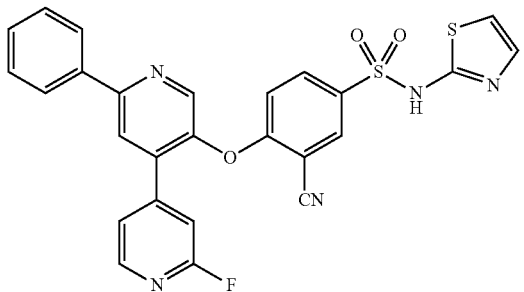 [SMILES: N#Cc1cc(S(=O)(=O)Nc2nccs2)ccc1Oc1cnc(-c2ccccc2)cc1-c1ccnc(F)c1]

3 mg (30% yield) of the title compound was obtained in the same manner as described in Example 29, except that (2-fluoropyridin-4-yl)boronic acid was used instead of (2-fluoropyridin-3-yl)boronic acid.

$^1$H NMR (CD$_3$OD/CDCl$_3$, 500 MHz) δ 8.63 (s, 1H), 8.11 (m, 1H), 8.08 (m, 2H), 8.02 (m, 2H), 7.93 (m, 1H), 7.52 (m, 3H), 7.12 (m, 1H), 6.91 (m, 1H), 6.71 (m, 3H)

Example 32

Preparation of 3-cyano-4-((6-fluoro-5-methyl-6'-phenyl-[3,4'-bipyridin]-3'-yl)oxy)-N-(thiazol-2-yl)benzenesulfonamide

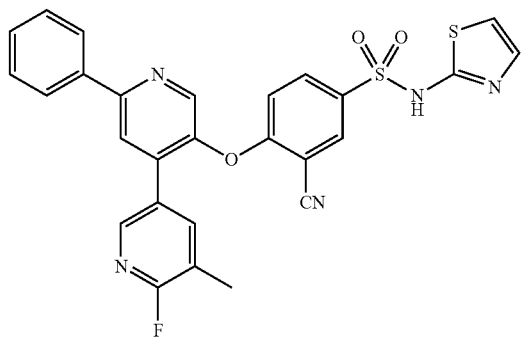 [SMILES: Cc1cc(-c2cc(-c3ccccc3)ncc2Oc2ccc(S(=O)(=O)Nc3nccs3)cc2C#N)cnc1F]

3 mg (30% yield) of the title compound was obtained in the same manner as described in Example 29, except that (6-fluoro-5-methylpyridin-3-yl)boronic acid was used instead of (2-fluoropyridin-3-yl)boronic acid.

$^1$H NMR (CD$_3$OD/CDCl$_3$, 500 MHz) δ 8.57 (s, 1H), 8.22 (m, 1H), 8.13 (m, 1H), 8.07 (m, 2H), 8.05 (m, 1H), 8.01 (m, 1H), 7.91 (m, 1H), 7.52 (m, 3H), 7.11 (m, 1H), 6.85 (m, 1H), 6.72 (m, 1H), 2.29 (s, 3H)

Example 33

Preparation of 3-cyano-4-((6'-phenyl-[3,4'-bipyridin]-3'-yl)oxy)-N-(thiazol-2-yl)benzenesulfonamide

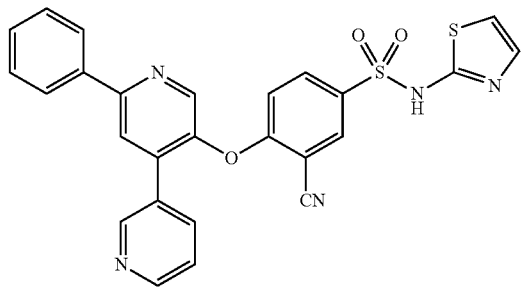 [SMILES: N#Cc1cc(S(=O)(=O)Nc2nccs2)ccc1Oc1cnc(-c2ccccc2)cc1-c1cccnc1]

3 mg (30% yield) of the title compound was obtained in the same manner as described in Example 29, except that pyridin-3-ylboronic acid was used instead of (2-fluoropyridin-3-yl)boronic acid.

$^1$H NMR (CD$_3$OD/CDCl$_3$, 500 MHz) δ 8.05 (m, 1H), 8.65 (s, 1H), 8.50 (m, 1H), 8.12 (m, 5H), 7.92 (m, 1H), 7.48 (m, 4H), 7.12 (m, 1H), 6.98 (d, 1H), 6.74 (d, 1H)

Example 34

Preparation of 3-cyano-4-((6-phenyl-4-(pyrimidin-5-yl)pyridin-3-yl)oxy)-N-(thiazol-2-yl)benzenesulfonamide

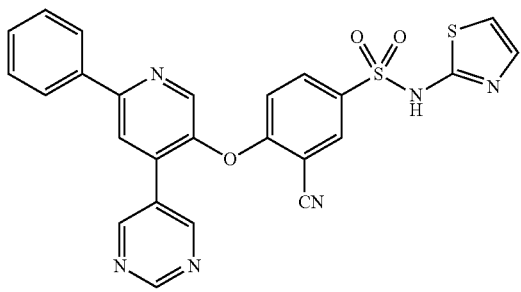 [SMILES: N#Cc1cc(S(=O)(=O)Nc2nccs2)ccc1Oc1cnc(-c2ccccc2)cc1-c1cncnc1]

3 mg (30% yield) of the title compound was obtained in the same manner as described in Example 29, except that (pyrimidin-5-yl)boronic acid was used instead of (2-fluoropyridin-3-yl)boronic acid.

$^1$H NMR (CD$_3$OD/CDCl$_3$, 500 MHz) δ 9.13 (m, 3H), 8.65 (s, 1H), 8.19 (m, 2H), 8.12 (m, 2H), 7.99 (m, 1H), 7.51 (m, 3H), 7.10 (m, 1H), 7.06 (m, 1H), 6.72 (m, 1H)

Example 35

Preparation of 4-((3'-chloro-6-phenyl-[4,4'-bipyridin]-3-yl)oxy)-3-cyano-N-(thiazol-2-yl)benzenesulfonamide

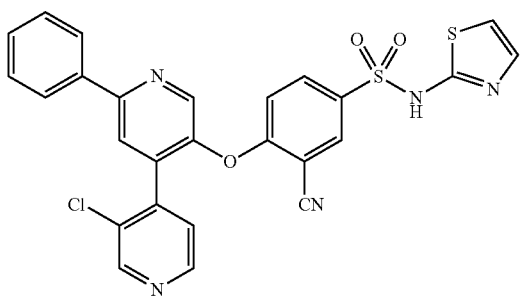 [SMILES: N#Cc1cc(S(=O)(=O)Nc2nccs2)ccc1Oc1cnc(-c2ccccc2)cc1-c1ccncc1Cl]

3 mg (30% yield) of the title compound was obtained in the same manner as described in Example 29, except that (3-chloropyridin-4-yl)boronic acid was used instead of (2-fluoropyridin-3-yl)boronic acid.

$^1$H NMR (CD$_3$OD/CDCl$_3$, 500 MHz) δ 8.55 (m, 1H), 8.26 (m, 1H), 8.10 (m, 1H), 7.99 (m, 3H), 7.72 (m, 1H), 7.66 (m, 1H), 7.57 (m, 1H), 7.50 (m, 2H), 7.44 (m, 1H), 7.13 (m, 2H), 6.75 (m, 1H)

Example 36

Preparation of 3-cyano-4-((2',3'-dichloro-6-phenyl-[4,4'-bipyridin]-3-yl)oxy)-N-(thiazol-2-yl)benzenesulfonamide

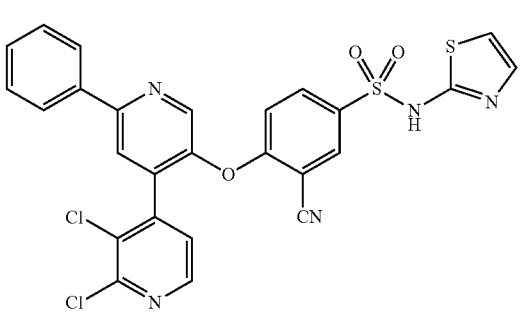 [SMILES: N#Cc1cc(S(=O)(=O)Nc2nccs2)ccc1Oc1cnc(-c2ccccc2)cc1-c1ccnc(Cl)c1Cl]

3 mg (30% yield) of the title compound was obtained in the same manner as described in Example 29, except that (2,3-dichloropyridin-4-yl)boronic acid was used instead of (2-fluoropyridin-3-yl)boronic acid.

$^1$H NMR (CD$_3$OD/CDCl$_3$, 500 MHz) δ 8.54 (m, 1H), 8.26 (m, 1H), 8.08 (m, 1H), 7.99 (m, 3H), 7.72 (m, 1H), 7.56 (m, 1H), 7.49 (m, 2H), 7.43 (m, 1H), 7.12 (m, 2H), 6.73 (m, 1H)

Example 37

Preparation of 3-cyano-4-((4-(3,5-dimethylisoxazol-4-yl)-6-phenylpyridin-3-yl)oxy)-N-(thiazol-2-yl)benzenesulfonamide

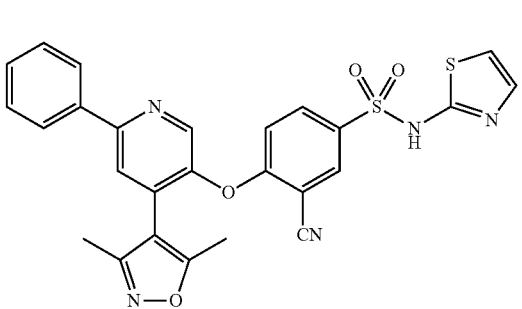 [SMILES: Cc1noc(C)c1-c1cc(-c2ccccc2)ncc1Oc1ccc(S(=O)(=O)Nc2nccs2)cc1C#N]

3 mg (30% yield) of the title compound was obtained in the same manner as described in Example 29, except that (3,5-dimethylisoxazol-4-yl)boronic acid was used instead of (2-fluoropyridin-3-yl)boronic acid.

$^1$H NMR (CD$_3$OD/CDCl$_3$, 500 MHz) δ 8.66 (s, 1H), 8.15 (m, 1H), 8.05 (m, 2H), 7.99 (m, 2H), 7.49 (m, 4H), 7.10 (m, 1H), 6.89 (m, 1H), 6.71 (m, 1H), 2.34 (s, 3H), 2.23 (s, 3H)

Example 38

Preparation of 3-cyano-4-((4-(1-methyl-1H-pyrazol-4-yl)-6-phenylpyridin-3-yl)oxy)-N-(thiazol-2-yl)benzenesulfonamide

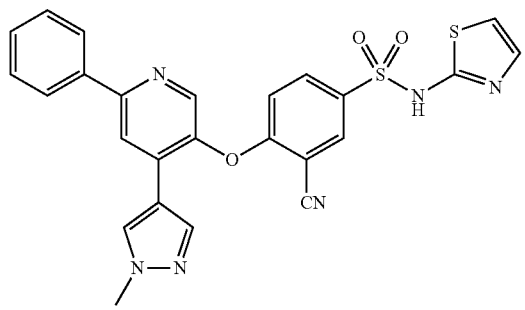 [SMILES: Cn1cc(-c2cc(-c3ccccc3)ncc2Oc2ccc(S(=O)(=O)Nc3nccs3)cc2C#N)cn1]

3 mg (30% yield) of the title compound was obtained in the same manner as described in Example 29, except that 1-methyl-4-(4,4,5,5-tetramethyl-1,3,2-dioxaboran-2-yl)-1H-pyrazole was used instead of (2-fluoropyridin-3-yl)boronic acid.

$^1$H NMR (CD$_3$OD/CDCl$_3$, 500 MHz) δ 8.45 (m, 1H), 8.27 (m, 1H), 8.20 (m, 2H), 8.05 (m, 3H), 7.98 (m, 1H), 7.50 (m, 2H), 7.47 (m, 1H), 7.10 (m, 1H), 6.94 (m, 1H), 6.71 (m, 1H), 3.89 (s, 2H)

Example 39

Preparation of 3-cyano-4-((6-phenyl-4-(1H-pyrazol-4-yl)pyridin-3-yl)oxy)-N-(thiazol-2-yl)benzenesulfonamide

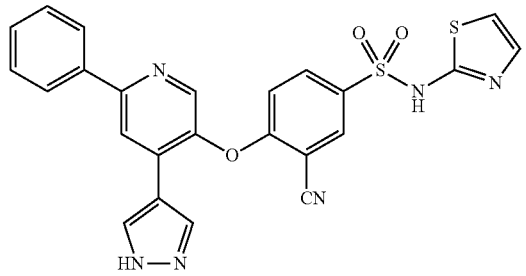 [SMILES: N#Cc1cc(S(=O)(=O)Nc2nccs2)ccc1Oc1cnc(-c2ccccc2)cc1-c1cn[nH]c1]

3 mg (30% yield) of the title compound was obtained in the same manner as described in Example 29, except that tert-butyl 4-(4,4,5,5-tetramethyl-1,3,2-dioxaboran-2-yl)-1H-pyrazol-1-carboxylate was used instead of (2-fluoropyridin-3-yl)boronic acid.

$^1$H NMR (CD$_3$OD/CDCl$_3$, 500 MHz) δ 8.47 (s, 1H), 8.24 (m, 4H), 8.05 (m, 2H), 7.97 (m, 1H), 7.52 (m, 2H), 7.49 (m, 1H), 7.10 (m, 1H), 6.93 (m, 1H), 6.71 (m, 1H)

Example 40

Preparation of 3-cyano-4-((6-phenyl-[4,4'-bipyridin]-3-yl)oxy)-N-(thiazol-2-yl)benzenesulfonamide

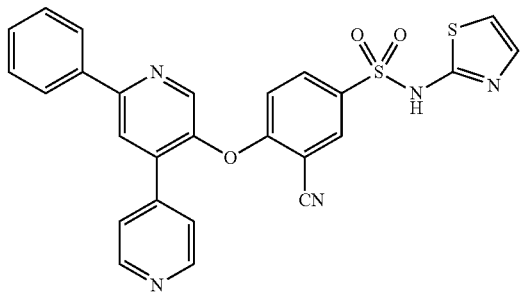 [SMILES: N#Cc1cc(S(=O)(=O)Nc2nccs2)ccc1Oc1cnc(-c2ccccc2)cc1-c1ccncc1]

3 mg (30% yield) of the title compound was obtained in the same manner as described in Example 29, except that (pyridin-4-yl)boronic acid was used instead of (2-fluoropyridin-3-yl)boronic acid.

$^1$H NMR (CD$_3$OD/CDCl$_3$, 500 MHz) δ 8.67 (s, 1H), 8.59 (m, 2H), 8.14 (m, 1H), 8.09 (m, 3H), 7.94 (m, 1H), 7.70 (m, 2H), 7.52 (m, 2H), 7.47 (m, 1H), 7.12 (m, 1H), 6.99 (m, 1H), 6.76 (m, 1H)

Example 41

Preparation of 3-cyano-4-((4-(2,5-dimethylthiophen-3-yl)-6-phenylpyridin-3-yl)oxy)-N-(thiazol-2-yl)benzenesulfonamide

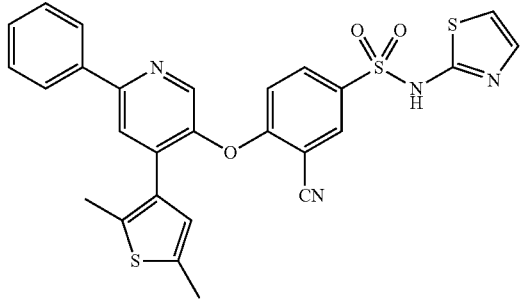 [SMILES: Cc1cc(-c2cc(-c3ccccc3)ncc2Oc2ccc(S(=O)(=O)Nc3nccs3)cc2C#N)c(C)s1]

3 mg (30% yield) of the title compound was obtained in the same manner as described in Example 29, except that (2,5-dimethylthiophen-3-yl)boronic acid was used instead of (2-fluoropyridin-3-yl)boronic acid.

$^1$H NMR (CD$_3$OD/CDCl$_3$, 500 MHz) δ 8.64 (s, 1H), 8.06 (m, 3H), 7.89 (m, 2H), 7.50 (m, 2H), 7.46 (m, 2H), 7.16 (d, 1H), 6.81 (m, 2H), 6.63 (s, 1H), 2.27 (s, 6H)

Example 42

Preparation of 3-cyano-4-((4-(5-methylthiophen-2-yl)-6-phenylpyridin-3-yl)oxy)-N-(thiazol-2-yl)benzenesulfonamide

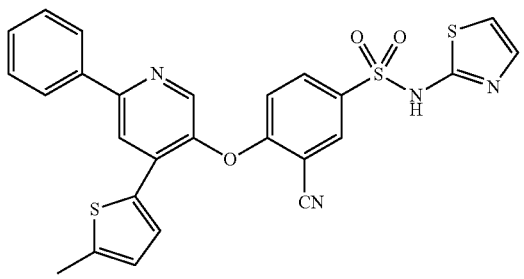 [SMILES: Cc1ccc(-c2cc(-c3ccccc3)ncc2Oc2ccc(S(=O)(=O)Nc3nccs3)cc2C#N)s1]

3 mg (30% yield) of the title compound was obtained in the same manner as described in Example 29, except that (5-methylthiophen-2-yl)boronic acid was used instead of (2-fluoropyridin-3-yl)boronic acid.

$^1$H NMR (CD$_3$OD/CDCl$_3$, 500 MHz) δ 8.54 (s, 1H), 8.27 (s, 1H), 8.10 (m, 1H), 8.07 (m, 3H), 7.74 (m, 1H), 7.72 (m, 2H), 7.50 (m, 1H), 7.47 (m, 1H), 7.45 (m, 2H), 7.13 (m, 1H), 6.75 (d, 1H), 2.13 (s, 3H)

Example 43

Preparation of 3-cyano-4-((4-(2-cyclopropylthiazol-4-yl)-6-phenylpyridin-3-yl)oxy)-N-(thiazol-2-yl)benzenesulfonamide

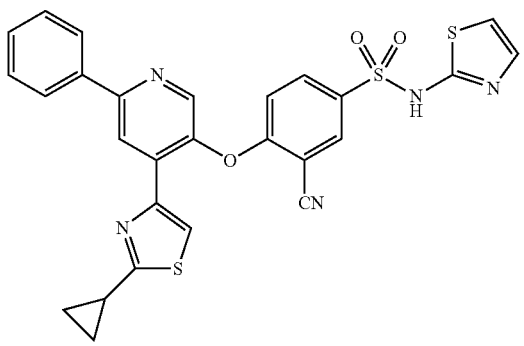 [SMILES: N#Cc1cc(S(=O)(=O)Nc2nccs2)ccc1Oc1cnc(-c2ccccc2)cc1-c1csc(C2CC2)n1]

3 mg (30% yield) of the title compound was obtained in the same manner as described in Example 29, except that 2-cyclopropyl-4-(4,4,5,5-tetramethyl-1,3,2-dioxaboran-2-yl)thiazole was used instead of (2-fluoropyridin-3-yl)boronic acid.

$^1$H NMR (CD$_3$OD/CDCl$_3$, 500 MHz) δ 8.54 (s, 1H), 8.48 (s, 1H), 8.24 (s, 1H), 8.05 (d, 1H), 7.97 (m, 1H), 7.88 (s, 1H), 7.64 (m, 1H), 7.55 (m, 2H), 7.50 (m, 1H), 7.13 (d, 1H), 6.93 (d, 1H), 6.74 (m, 1H), 2.33 (m, 1H), 1.61 (m, 4H)

Example 44

Preparation of 3-cyano-4-((4-(1-cyclopropyl-1H-pyrazol-4-yl)-6-phenylpyridin-3-yl)oxy)-N-(thiazol-2-yl)benzenesulfonamide

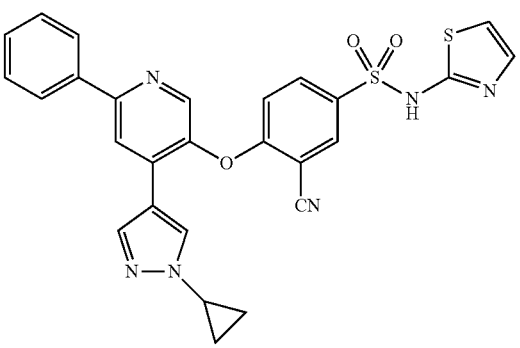 [SMILES: N#Cc1cc(S(=O)(=O)Nc2nccs2)ccc1Oc1cnc(-c2ccccc2)cc1-c1cnn(C2CC2)c1]

3 mg (30% yield) of the title compound was obtained in the same manner as described in Example 29, except that 1-cyclopropyl-4-(4,4,5,5-tetramethyl-1,3,2-dioxaboran-2-yl)-1H-pyrazole was used instead of (2-fluoropyridin-3-yl)boronic acid.

$^1$H NMR (CD$_3$OD/CDCl$_3$, 500 MHz) δ 8.56 (s, 1H), 8.23 (s, 1H), 8.08 (m, 2H), 8.00 (m, 2H), 7.74 (m, 1H), 7.72 (m, 1H), 7.66 (m, 1H), 7.56 (m, 2H), 7.29 (m, 1H), 7.13 (m, 2H), 6.75 (d, 1H), 2.32 (m, 1H), 1.61 (m, 4H)

Example 45

Preparation of 3-cyano-4-((4-(furan-3-yl)-6-(1H-pyrazol-4-yl)pyridin-3-yl)oxy)-N-(thiazol-2-yl)benzenesulfonamide

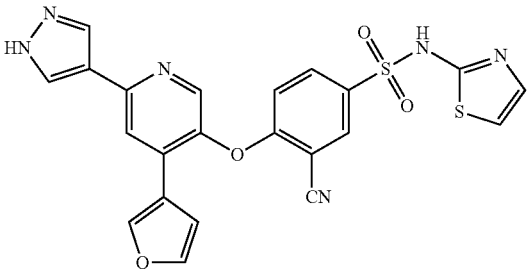 [SMILES: N#Cc1cc(S(=O)(=O)Nc2nccs2)ccc1Oc1cnc(-c2cn[nH]c2)cc1-c1ccoc1]

32 mg (30% yield) of the title compound was obtained in the same manner as described in Example 5, except that (1H-pyrzol-4-yl)boronic acid was used instead of (3-fluorophenyl)boronic acid.

$^1$H NMR (CDCl$_3$, 500 MHz) δ 8.53 (t, 1H), 8.36 (s, 1H), 8.28 (s, 1H), 8.09 (d, 2H), 7.80 (d, 1H), 7.67 (d, 1H), 7.52 (s, 1H), 7.36 (t, 1H), 7.09 (d, 1H), 7.00 (t, 1H), 6.87 (s, 1H), 6.56 (d, 1H)

Example 46

Preparation of 3-cyano-4-((4-(furan-3-yl)-6-(1-methyl-1H-pyrazol-4-yl)pyridin-3-yl)oxy)-N-(thiazol-2-yl)benzenesulfonamide

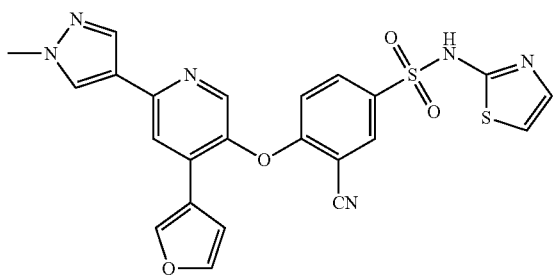 [SMILES: Cn1cc(-c2cc(-c3ccoc3)c(Oc3ccc(S(=O)(=O)Nc4nccs4)cc3C#N)cn2)cn1]

29 mg (26% yield) of the title compound was obtained in the same manner as described in Example 5, except that 1-methyl-4-(4,4,5,5-tetramethyl-1,3,2-dioxaboran-2-yl)-1H-pyrzole was used instead of (3-fluorophenyl)boronic acid.

$^1$H NMR (CD$_3$OD, 500 MHz) δ 8.89 (s, 1H), 8.61 (m, 1H), 8.33 (s, 1H), 8.23 (s, 1H), 8.20 (s, 1H), 7.79 (dd, 1H), 7.68 (d, 1H), 7.63 (s, 1H), 7.20 (dd, 1H), 7.13 (m, 3H), 6.75 (d, 1H)

Example 47

Preparation of 3-fluoro-4-((2'-fluoro-4-(furan-3-yl)-[2,3'-bipyridin]-5-yl)oxy)-N-(thiazol-2-yl)benzenesulfonamide

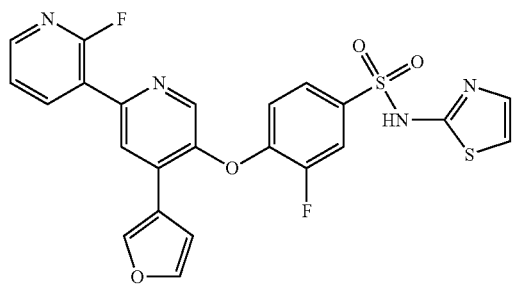 [SMILES: O=S(=O)(Nc1nccs1)c1ccc(Oc2cnc(-c3cccnc3F)cc2-c2ccoc2)c(F)c1]

10.0 mg of 4-((6-chloro-4-(furan-3-yl)pyridin-3-yl)oxy)-3-fluoro-N-(thiazol-2-yl)benzenesulfonamide was dissolved in 1,4-dioxane/H$_2$O=1:1 (0.48 mL), and 3.2 mg of 2-fluoropyridin-3-yl)boronic acid, 0.84 mg of Pd(PPh$_3$)$_4$ and 7.7 mg of Na$_2$CO$_3$, were added thereto. After reacting with microwave reactor at 120° C. for 5 minutes, 1,4-dioxane was removed by concentrating under reduced pressure. After extracting with ethyl acetate, the extract was treated with MgSO$_4$, and concentrated under reduced pressure. The residue was purified by PLC (developing solvent, EA:n-Hex=2:1) to obtain 3.9 mg (34% yield) of the title compound.

$^1$H NMR (CD$_3$OD, 500 MHz) δ 8.39 (s, 1H), 8.27 (s, 2H), 8.10 (s, 1H), 8.06 (s, 1H), 7.99 (d, 1H), 7.83 (s, 1H), 7.63 (s, 1H), 7.60 (s, 1H), 7.54 (s, 1H), 7.10 (d, 1H), 7.02 (s, 1H), 6.93 (d, 1H), 6.73 (d, 1H)

Example 48

Preparation of 3-fluoro-4-((6'-fluoro-4-(furan-3-yl)-[2,3'-bipyridin]-5-yl)oxy)-N-(thiazol-2-yl)benzenesulfonamide

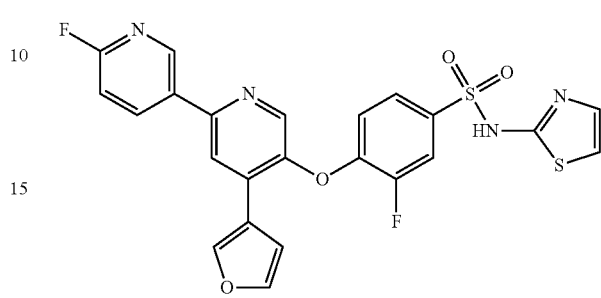

3.9 mg (34% yield) of the title compound was obtained in the same manner as described in Example 47, except that (6-fluoropyridin-3-yl)boronic acid was used instead of (2-fluoropyridin-3-yl)boronic acid.

$^1$H NMR (CDCl$_3$, 500 MHz) δ 8.29 (s, 1H), 8.00 (s, 1H), 7.97 (s, 1H), 7.94 (s, 1H), 7.71 (d, 1H), 7.66 (d, 1H), 7.62 (s, 1H), 7.56 (t, 1H), 7.54 (s, 1H), 7.38 (d, 1H), 6.89 (t, 1H), 6.83 (s, 1H), 3.98 (s, 3H)

Example 49

Preparation of 3-cyano-4-((6-fluoro-[3,2':4',3''-terpyridin]-5'-yl)oxy)-N-(thiazol-2-yl)benzenesulfonamide

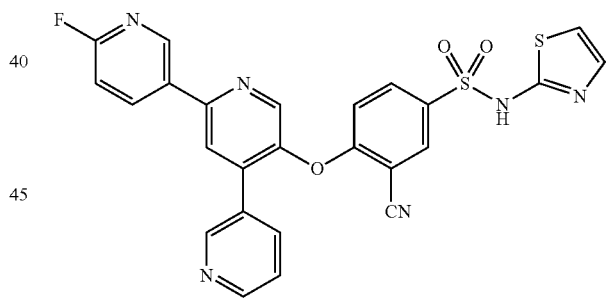

10 mg (0.02 mmol) of 4-((6'-chloro-[3,4'-bipyridin]-3'-yl)oxy)-3-cyano-N-(thiazol-2-yl)benzenesulfonamide was dissolved in 3 mL of N,N-dimethylformamide, and 4.5 mg (0.03 mmol) of (6-fluoropyridin-3-yl)boronic acid was added thereto, and then 2.4 mg (10 mol %) of Pd(PPh$_3$)$_4$, 6.7 mg (0.6 mmol) of Na$_2$CO$_3$, and 1 mL of H$_2$O were added thereto. After reacting with microwave reactor at 120° C. for 10 minutes, the solvent was removed, and the remaining material was diluted with ethyl acetate and the organic layer was separated, and washed with saturated sodium chloride. The organic layer was collected, dried with magnesium sulfate to remove water, and concentrated under reduced pressure, and the residue was purified by column chromatography (developing solvent, hexane:ethyl acetate=3:1) to obtain 3 mg (27% yield) of the title compound.

$^1$H NMR (CD$_3$OD, 500 MHz) δ 8.97 (d, 1H), 8.82 (s, 1H), 8.70 (m, 2H), 8.52 (m, 1H), 8.21 (m, 1H), 8.13 (m, 2H), 7.79

(m, 1H), 7.39 (m, 1H), 7.48 (m, 1H), 7.23 (m, 1H), 7.14 (m, 1H), 7.00 (d, 1H), 6.75 (d, 1H)

Example 50

Preparation of 3-cyano-4-((6'-(3-fluorophenyl)-[3,4'-bipyridin]-3'-yl)oxy)-N-(thiazol-2-yl)benzenesulfonamide

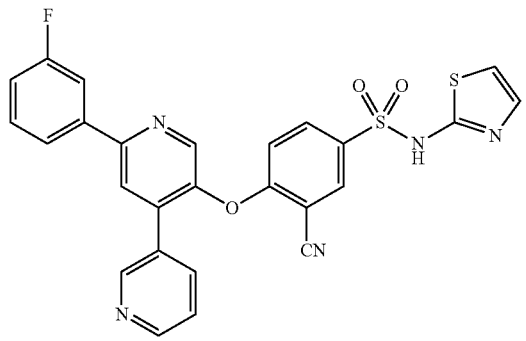 [SMILES: N#Cc1cc(S(=O)(=O)Nc2nccs2)ccc1Oc1cnc(-c2cccc(F)c2)cc1-c1cccnc1]

3 mg (30% yield) of the title compound was obtained in the same manner as described in Example 49, except that (3-fluorophenyl)boronic acid was used instead of (6-fluoropyridin-3-yl)boronic acid.

$^1$H NMR (CD$_3$OD/CDCl$_3$, 500 MHz) δ 8.80 (d, 1H), 8.67 (s, 1H), 8.50 (m, 1H), 8.15 (m, 3H), 7.94 (m, 3H), 7.52 (m, 2H), 7.22 (m, 1H), 7.13 (m, 1H), 6.99 (d, 1H), 6.75 (d, 1H)

Example 51

Preparation of 3-cyano-4-((2-fluoro-[3,2':4',3''-terpyridin]-5'-yl)oxy)-N-(thiazol-2-yl)benzenesulfonamide

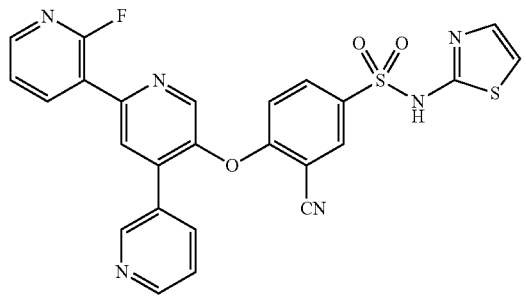 [SMILES: N#Cc1cc(S(=O)(=O)Nc2nccs2)ccc1Oc1cnc(-c2cccnc2F)cc1-c1cccnc1]

3 mg (30% yield) of the title compound was obtained in the same manner as described in Example 49, except that (2-fluoropyridin-3-yl)boronic acid was used instead of (6-fluoropyridin-3-yl)boronic acid.

$^1$H NMR (CD$_3$OD/CDCl$_3$, 500 MHz) δ 8.79 (s, 1H), 8.74 (s, 1H), 8.62 (m, 1H), 8.52 (m, 1H), 8.30 (m, 1H), 8.14 (m, 3H), 7.96 (m, 1H), 7.51 (m, 2H), 7.13 (d, 1H), 7.03 (d, 1H), 6.74 (d, 1H)

Example 52

Preparation of 3-cyano-4-((6'-(2-fluorophenyl)-[3,4'-bipyridin]-3'-yl)oxy)-N-(thiazol-2-yl)benzenesulfonamide

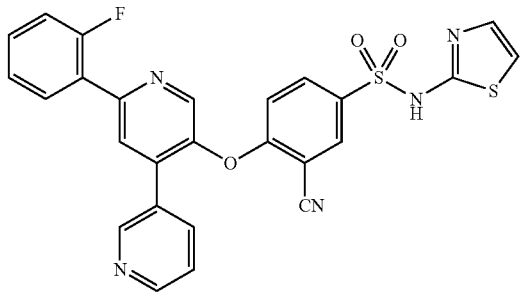 [SMILES: N#Cc1cc(S(=O)(=O)Nc2nccs2)ccc1Oc1cnc(-c2ccccc2F)cc1-c1cccnc1]

3 mg (30% yield) of the title compound was obtained in the same manner as described in Example 49, except that (2-fluorophenyl)boronic acid was used instead of (6-fluoropyridin-3-yl)boronic acid.

$^1$H NMR (CD$_3$OD/CDCl$_3$, 500 MHz) δ 8.78 (m, 1H), 8.69 (s, 1H), 8.51 (d, 1H), 8.13 (s, 1H), 8.09 (d, 1H), 8.03 (m, 2H), 7.96 (m, 1H), 7.49 (m, 2H), 7.45 (m, 1H), 7.34 (m, 1H), 7.10 (m, 1H), 7.00 (d, 1H), 6.71 (m, 1H)

Example 53

Preparation of 3-cyano-4-((2,6-difluoro-[3,2':4',4''-terpyridin]-5'-yl)oxy)-N-(thiazol-2-yl)benzenesulfonamide

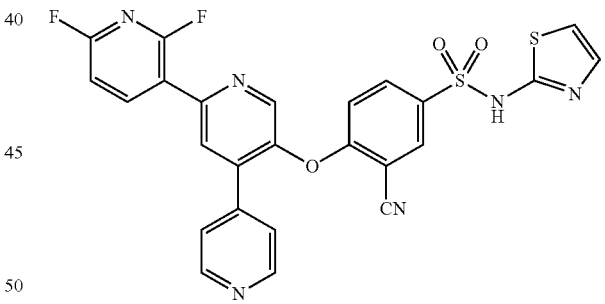

10 mg (0.02 mmol) of 4-((6-chloro-[4,4'-bipyridin]-3-yl)oxy)-3-cyano-N-(thiazol-2-yl)benzenesulfonamide was dissolved in 3 mL of N,N-dimethylformamide, and 5 mg (0.03 mmol) of (2,6-difluoropyridin-3-yl)boronic acid was added thereto, and then 2.4 mg (10 mol %) of Pd(PPh$_3$)$_4$, 6.7 mg (0.6 mmol) of Na$_2$CO$_3$, and 1 mL of H$_2$O were added thereto. After reacting with microwave reactor at 120° C. for 10 minutes, the solvent was removed, and the remaining material was diluted with ethyl acetate and the organic layer was separated, and washed with saturated sodium chloride. The organic layer was collected, dried with magnesium sulfate to remove water, and concentrated under reduced pressure, and the residue was purified by column chromatography (developing solvent, hexane:ethyl acetate=3:1) to obtain 2 mg (19% yield) of the title compound.

¹H NMR (CD₃OD, 500 MHz) δ 8.76 (m, 2H), 8.59 (m, 2H), 8.15 (s, 1H), 8.10 (s, 1H), 7.96 (d, 1H), 7.66 (m, 2H), 7.20 (m, 1H), 7.12 (m, 1H), 7.04 (d, 1H), 6.74 (m, 1H)

Example 54

Preparation of 4-((4,6-bis(1-methyl-1H-pyrazol-4-yl)pyridin-3-yl)oxy)-3-cyano-N-(thiazol-2-yl)benzenesulfonamide

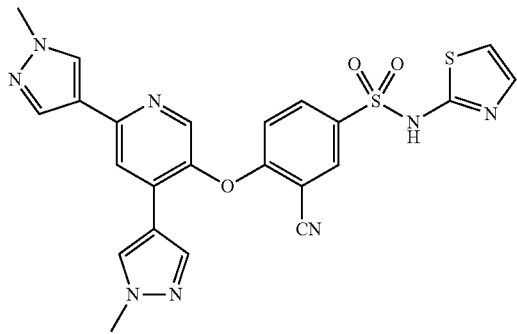 [SMILES: Cn1cc(-c2cc(-c3cnn(C)c3)c(Oc3ccc(S(=O)(=O)Nc4nccs4)cc3C#N)cn2)cn1]

10 mg (0.04 mmol) of 4,6-bis(1-methyl-1H-pyrazol-4-yl)pyridin-3-ol was dissolved in 3 mL of N,N-dimethylformamide, and 32 mg (0.1 mmol) of Cs₂CO₃ was added thereto, followed by stirring at room temperature for 10 minutes. Then, 11 mg (0.04 mmol) of 3-cyano-4-fluoro-N-(thiazol-2-yl)benzenesulfonamide was added thereto, and the solution was stirred at room temperature for 3 hours. After completion of the reaction as checked by TLC, the solvent was removed, and the remaining material was diluted with ethyl acetate and washed with saturated sodium chloride. The organic layer was collected, dried with magnesium sulfate to remove water, and concentrated under reduced pressure, and the residue was purified by column chromatography (developing solvent, hexane:ethyl acetate=3:1) to obtain 16.0 mg (80% yield) of the title compound.

¹H NMR (CDCl₃, 500 MHz) δ 8.34 (s, 1H), 8.24 (s, 1H), 8.20 (s, 1H), 8.14 (s, 1H), 8.08 (s, 1H), 7.98 (m, 3H), 7.10 (d, 1H), 6.90 (d, 1H), 6.71 (d, 1H), 3.96 (s, 3H), 3.88 (s, 3H)

Example 55

Preparation of 4-((4,6-bis(1-methyl-1H-pyrazol-4-yl)pyridin-3-yl)oxy)-3-cyano-N-(1,2,4-thiadiazol-5-yl)benzenesulfonamide

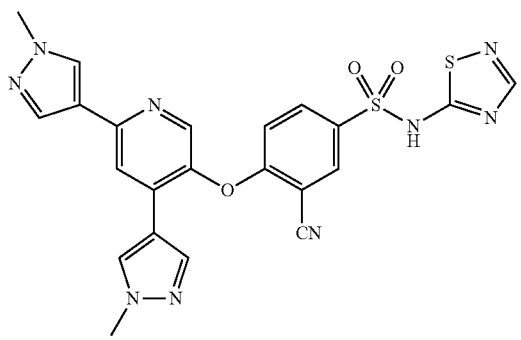 [SMILES: Cn1cc(-c2cc(-c3cnn(C)c3)c(Oc3ccc(S(=O)(=O)Nc4ncns4)cc3C#N)cn2)cn1]

16 mg (80% yield) of the title compound was obtained in the same manner as described in Example 54, except that 3-cyano-4-fluoro-N-(1,2,4-thiadiazol-5-yl)benzenesulfonamide was used instead of 3-cyano-4-fluoro-N-(thiazol-2-yl)benzenesulfonamide.

¹H NMR (CD₃OD/CDCl₃, 500 MHz) δ 8.31 (s, 1H), 8.22 (m, 2H), 8.13 (s, 1H), 8.09 (s, 1H), 7.96 (m, 3H), 7.92 (s, 1H), 6.86 (d, 1H), 3.96 (s, 3H), 3.87 (s, 3H)

Example 56

Preparation of 5-chloro-2-fluoro-4-((2'-fluoro-4-(furan-3-yl)-[2,3'-bipyridin]-5-yl)oxy)-N-(thiazol-4-yl)benzenesulfonamide

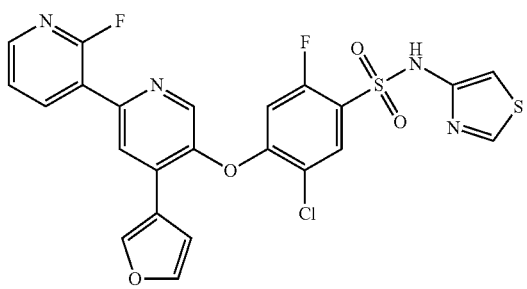 [SMILES: O=S(=O)(Nc1cscn1)c1cc(Cl)c(Oc2cnc(-c3cccnc3F)cc2-c2ccoc2)cc1F]

10 mg of tert-butyl((5-chloro-4-((6-chloro-4-(furan-3-yl)pyridin-3-yl)oxy)-2-fluorophenyl)sulfonyl)(thiazol-4-yl)carbamate was dissolved in 1,4-dioxane/H₂O=1:1 (0.38 mL), and 3.5 mg of (2-fluoropyridin-3-yl)boronic acid, 0.65 mg (3 mol %) of Pd(PPh₃)₄ and 5.96 mg of Na₂CO₃ were added thereto. After reacting with microwave reactor at 120° C. for 5 minutes, 1,4-dioxane was removed by concentrating under reduced pressure. After extracting with ethyl acetate, the extract was treated with MgSO4, and concentrated under reduced pressure. The residue was separated by PLC (developing solvent, EA:n-Hex=1:1) to obtain 6.7 mg (72% yield) of the title compound.

¹H NMR (CDCl₃, 500 MHz) δ 9.49 (s, 1H), 8.64 (s, 1H), 8.58 (t, 1H), 8.43 (s, 1H), 8.29 (s, 1H), 8.12 (s, 1H), 8.00 (d, 2H), 7.50 (s, 1H), 7.37 (t, 1H), 7.04 (s, 1H), 6.82 (s, 1H), 6.50 (d, 1H)

Example 57

Preparation of 5-chloro-2-fluoro-4-((6'-fluoro-4-(furan-3-yl)-[2,3'-bipyridin]-5-yl)oxy)-N-(thiazol-4-yl)benzenesulfonamide

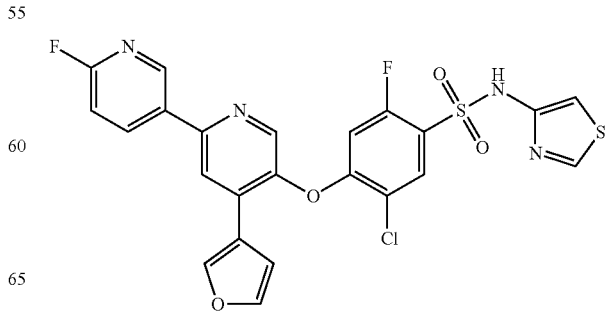

9.1 mg (97% yield) of the title compound was obtained in the same manner as described in Example 56, except that (6-fluoropyridin-3-yl)boronic acid was used instead of (2-fluoropyridin-3-yl)boronic acid.

¹H NMR (CDCl₃, 500 MHz) δ 10.3 (s, 1H), 8.80 (s, 1H), 8.68 (s, 1H), 8.45 (m, 1H), 8.43 (s, 1H), 8.00 (d, 1H), 7.99 (s, 1H), 7.85 (s, 1H), 7.50 (s, 1H), 7.05 (d, 1H), 7.00 (s, 1H), 6.81 (s, 1H), 6.47 (d, 1H)

Example 58

Preparation of 5-chloro-4-((2',6'-difluoro-4-(furan-3-yl)-[2,3'-bipyridin]-5-yl)oxy)-2-fluoro-N-(thiazol-4-yl)benzenesulfonamide

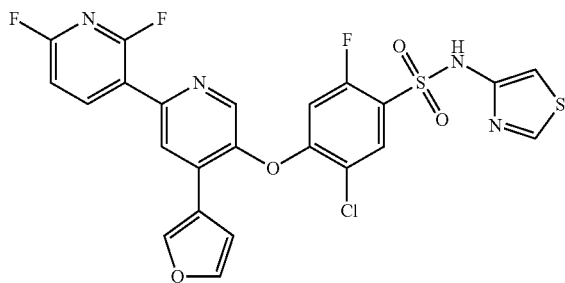 [SMILES: O=S(=O)(Nc1cscn1)c1cc(Cl)c(Oc2cnc(-c3ccc(F)nc3F)cc2-c2ccoc2)cc1F]

8.6 mg (89% yield) of the title compound was obtained in the same manner as described in Example 56, except that (2,6-difluoropyridin-3-yl)boronic acid was used instead of (2-fluoropyridin-3-yl)boronic acid.

¹H NMR (CDCl₃, 500 MHz) δ 10.1 (s, 1H), 8.70 (s, 1H), 8.67 (s, 1H), 8.40 (s, 1H), 8.06 (s, 1H), 8.01 (s, 1H), 7.99 (s, 1H), 7.50 (s, 1H), 7.01 (s, 1H), 6.99 (s, 1H), 6.81 (s, 1H), 6.48 (d, 1H)

Example 59

Preparation of 5-chloro-2-fluoro-4-((6-(3-fluorophenyl)-4-(furan-3-yl)pyridin-3-yl)oxy)-N-(thiazol-4-yl)benzenesulfonamide

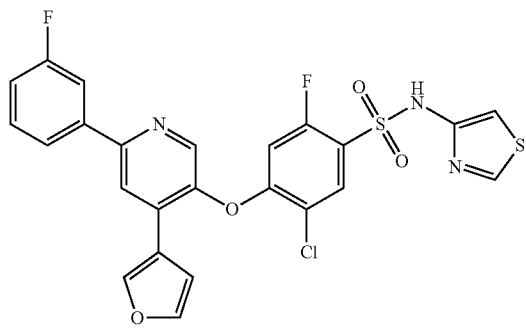 [SMILES: O=S(=O)(Nc1cscn1)c1cc(Cl)c(Oc2cnc(-c3cccc(F)c3)cc2-c2ccoc2)cc1F]

8.7 mg (93% yield) of the title compound was obtained in the same manner as described in Example 56, except that (3-fluorophenyl)boronic acid was used instead of (2-fluoropyridin-3-yl)boronic acid.

¹H NMR (CDCl₃, 500 MHz) δ 9.75 (s, 1H), 8.66 (d, 1H), 8.40 (d, 1H), 7.99 (d, 1H), 7.98 (d, 1H), 7.86 (d, 1H), 7.76 (dd, 1H), 7.72 (d, 1H), 7.50 (s, 1H), 7.46 (d, 1H), 7.14 (t, 1H), 7.02 (d, 1H), 6.81 (s, 1H), 6.46 (dd, 1H)

Example 60

Preparation of 5-chloro-2-fluoro-4-((6-(2-fluorophenyl)-4-(furan-3-yl)pyridin-3-yl)oxy)-N-(thiazol-4-yl)benzenesulfonamide

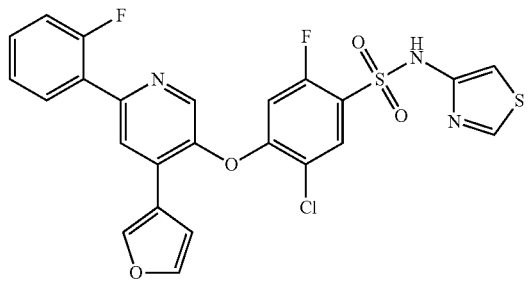 [SMILES: O=S(=O)(Nc1cscn1)c1cc(Cl)c(Oc2cnc(-c3ccccc3F)cc2-c2ccoc2)cc1F]

9.0 mg (97% yield) of the title compound was obtained in the same manner as described in Example 56, except that (2-fluorophenyl)boronic acid was used instead of (2-fluoropyridin-3-yl)boronic acid.

¹H NMR (CDCl₃, 500 MHz) δ 9.98 (s, 1H), 8.66 (s, 1H), 8.43 (s, 1H), 7.99 (m, 3H), 7.96 (s, 1H), 7.47 (s, 1H), 7.41 (m, 1H), 7.29 (m, 1H), 7.19 (m, 1H), 7.00 (s, 1H), 6.79 (s, 1H), 6.48 (d, 1H)

Example 61

Preparation of 5-chloro-2-fluoro-4-((6-(4-fluorophenyl)-4-(furan-3-yl)pyridin-3-yl)oxy)-N-(thiazol-4-yl)benzenesulfonamide

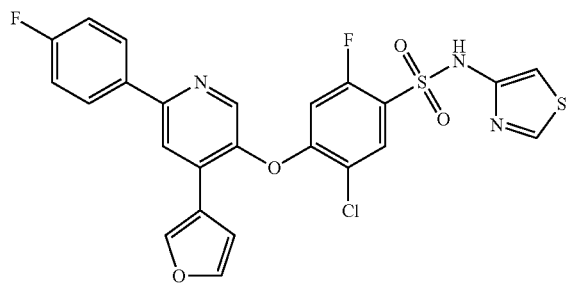

8.2 mg (88% yield) of the title compound was obtained in the same manner as described in Example 56, except that (4-fluorophenyl)boronic acid was used instead of (2-fluoropyridin-3-yl)boronic acid.

¹H NMR (CDCl₃, 500 MHz) δ 10.2 (s, 1H), 8.67 (s, 1H), 8.38 (s, 1H), 7.97 (m, 4H), 7.82 (s, 1H), 7.49 (s, 1H), 7.17 (t, 2H), 6.99 (d, 1H), 6.80 (s, 1H), 6.44 (d, 1H)

Example 62

Preparation of 5-chloro-2-fluoro-4-((2'-fluoro-4-(furan-3-yl)-[2,4'-bipyridin]-5-yl)oxy)-N-(thiazol-4-yl)benzenesulfonamide

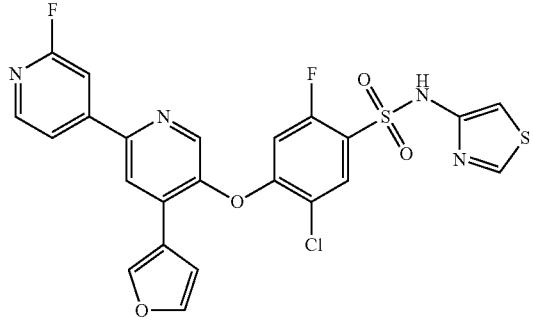 [SMILES: O=S(=O)(Nc1cscn1)c1cc(Cl)c(Oc2cnc(-c3ccnc(F)c3)cc2-c2ccoc2)cc1F]

8.3 mg (89% yield) of the title compound was obtained in the same manner as described in Example 56, except that (2-fluoropyridin-4-yl)boronic acid was used instead of (2-fluoropyridin-3-yl)boronic acid.

$^1$H NMR (CDCl$_3$, 500 MHz) δ 9.57 (s, 1H), 8.66 (s, 1H), 8.42 (s, 1H), 8.35 (d, 1H), 8.02 (s, 1H), 8.00 (s, 1H), 7.95 (s, 1H), 7.79 (d, 1H), 7.56 (d, 1H), 7.53 (d, 1H), 7.04 (d, 1H), 6.83 (d, 1H), 6.51 (d, 1H)

Example 63

Preparation of 5-chloro-2-fluoro-4-((6-(2-fluorophenyl)-4-(1-methyl-1H-pyrazol-4-yl)pyridin-3-yl)oxy)-N-(thiazol-4-yl)benzenesulfonamide 2,2,2-trifluoroacetate

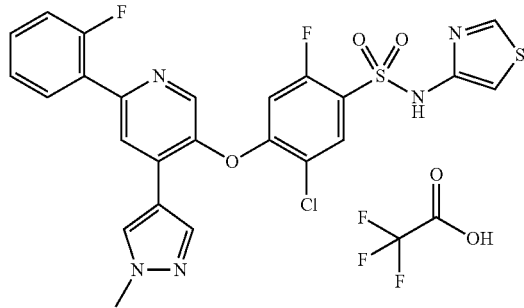

20 mg (0.03 mmol) of tert-butyl((5-chloro-2-fluoro-4-((6-(2-fluorophenyl)-4-(1-methyl-1H-pyrazol-4-yl)pyridin-3-yl)oxy)phenyl)sulfonyl)(thiazol-4-yl)carbamate was dissolved in 3 mL of dichloromethane, and 30 uL of trifluoroacetic acid was added thereto, followed by stirring at room temperature for 5 hours. After completion of the reaction as checked by TLC, the solvent was removed to obtain 7.0 mg (35% yield) of the title compound.

$^1$H NMR (CDCl$_3$, 500 MHz) δ 8.75 (m, 1H), 8.52 (s, 1H), 8.39 (d, 1H), 8.35 (d, 1H), 8.14 (m, 1H), 8.07 (m, 1H), 7.84 (m, 1H), 7.61 (m, 1H), 7.39 (m, 2H), 7.10 (m, 2H), 3.93 (s, 3H)

Example 64

Preparation of 5-chloro-2-fluoro-4-((6-(3-fluorophenyl)-4-(1-methyl-1H-pyrazol-5-yl)pyridin-3-yl)oxy)-N-(thiazol-2-yl)benzenesulfonamide

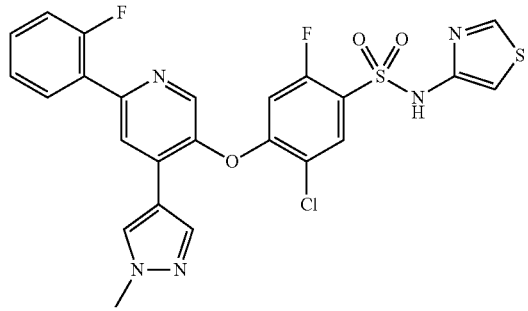 [SMILES: Cn1cc(-c2cc(-c3ccccc3F)ncc2Oc2cc(F)c(S(=O)(=O)Nc3cscn3)cc2Cl)cn1]

10 mg (0.02 mmol) of 5-chloro-4-((6-chloro-4-(1-methyl-1H-pyrazol-5-yl)pyridin-3-yl)oxy)-2-fluoro-N-(thiazol-2-yl)benzenesulfonamide was dissolved in 3 mL of N,N-dimethylformamide, and 4.2 mg (0.03 mmol) of (3-fluorophenyl)boronic acid was added thereto, and then 2.3 mg (10 mol %) of Pd(PPh$_3$)$_4$, 6.3 mg (0.6 mmol) of Na$_2$CO$_3$, and 1 mL of H$_2$O were added thereto. After reacting with microwave reactor at 120° C. for 10 minutes, the solvent was removed, and the remaining material was diluted with ethyl acetate and the organic layer was separated, and washed with saturated sodium chloride. The organic layer was collected, dried with magnesium sulfate to remove water, and concentrated under reduced pressure, and the residue was purified by column chromatography (developing solvent, hexane:ethyl acetate=3:1) to obtain 4 mg (36% yield) of the title compound.

$^1$H NMR (CD$_3$OD, 500 MHz) δ 8.51 (s, 1H), 8.06 (s, 2H), 7.98 (m, 1H), 7.89 (m, 2H), 7.49 (m, 3H), 7.18 (m, 1H), 7.00 (m, 1H), 6.52 (s, 1H), 3.92 (s, 3H)

Example 65

Preparation of 5-chloro-2-fluoro-4-((6-(4-fluorophenyl)-4-(1-methyl-1H-pyrazol-4-yl)pyridin-3-yl)oxy)-N-(thiazol-4-yl)benzenesulfonamide 2,2,2-trifluoroacetate

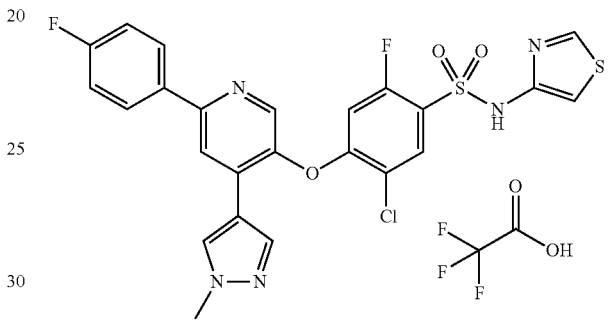

16 mg (80% yield) of the title compound was obtained in the same manner as described in Example 63, except that tert-butyl((5-chloro-2-fluoro-4-((6-(4-fluorophenyl)-4-(1-methyl-1H-pyrazol-4-yl)pyridin-3-yl)oxy)phenyl)sulfonyl)(thiazol-4-yl)carbamate was used instead of tert-butyl((5-chloro-2-fluoro-4-((6-(2-fluorophenyl)-4-(1-methyl-1H-pyrazol-4-yl)pyridin-3-yl)oxy)phenyl)sulfonyl)(thiazol-4-yl)carbamate.

$^1$H NMR (CD$_3$OD, 500 MHz) δ 8.73 (s, 1H), 8.45 (s, 1H), 8.36 (s, 2H), 8.17 (m, 1H), 8.05 (m, 3H), 7.34 (m, 2H), 7.09 (m, 1H), 7.01 (m, 1H), 3.93 (s, 3H)

Example 66

Preparation of 5-chloro-4-((6-(2,4-difluorophenyl)-4-(1-methyl-1H-pyrazol-4-yl)pyridin-3-yl)oxy)-2-fluoro-N-(thiazol-4-yl)benzenesulfonamide 2,2,2-trifluoroacetate

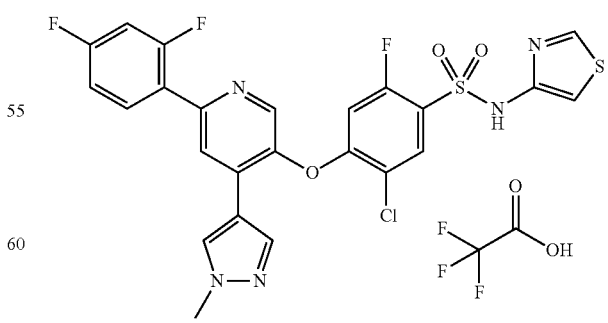

16 mg (80% yield) of the title compound was obtained in the same manner as described in Example 63, except that tert-butyl((5-chloro-4-((6-(2,4-difluorophenyl)-4-(1-methyl-1H-pyrazol-4-yl)pyridin-3-yl)oxy)-2-fluorophenyl)sulfonyl)(thiazol-4-yl)carbamate was used instead of tert-butyl ((5-chloro-2-fluoro-4-((6-(2-fluorophenyl)-4-(1-methyl-1H-pyrazol-4-yl)pyridin-3-yl)oxy)phenyl)sulfonyl)(thiazol-4-yl)carbamate.

$^1$H NMR (CD$_3$OD, 500 MHz) δ 8.73 (s, 1H), 8.40 (s, 1H), 8.30 (s, 1H), 8.24 (s, 1H), 8.08 (m, 2H), 7.92 (m, 1H), 7.20 (m, 2H), 7.09 (s, 1H), 6.99 (m, 1H)

Example 67

Preparation of 5-chloro-4-((6-(3,4-difluorophenyl)-4-(1-methyl-1H-pyrazol-4-yl)pyridin-3-yl)oxy)-2-fluoro-N-(thiazol-4-yl)benzenesulfonamide 2,2,2-trifluoroacetate

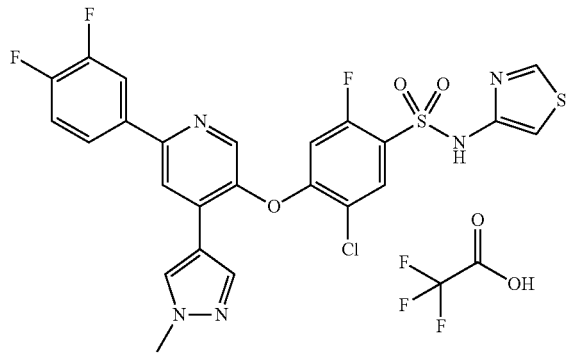

16 mg (80% yield) of the title compound was obtained in the same manner as described in Example 63, except that tert-butyl((5-chloro-4-((6-(3,4-difluorophenyl)-4-(1-methyl-1H-pyrazol-4-yl)pyridin-3-yl)oxy)-2-fluorophenyl)sulfonyl)(thiazol-4-yl)carbamate was used instead of tert-butyl ((5-chloro-2-fluoro-4-((6-(2-fluorophenyl)-4-(1-methyl-1H-pyrazol-4-yl)pyridin-3-yl)oxy)phenyl)sulfonyl)(thiazol-4-yl)carbamate.

$^1$H NMR (CD$_3$OD, 500 MHz) δ 8.73 (d, 1H), 8.40 (s, 1H), 8.29 (m, 2H), 8.10 (m, 1H), 8.03 (m, 2H), 7.89 (m, 1H), 7.43 (m, 1H), 7.08 (m, 1H), 6.87 (d, 1H), 3.91 (s, 3H)

Example 68

Preparation of 5-chloro-2-fluoro-4-((2'-fluoro-4-(1-methyl-1H-pyrazol-4-yl)-[2,4'-bipyridin]-5-yl)oxy)-N-(thiazol-4-yl)benzenesulfonamide 2,2,2-trifluoroacetate

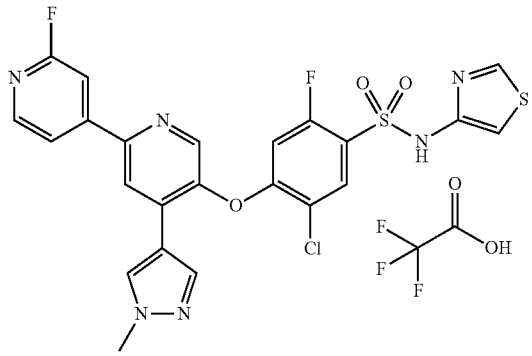

16 mg (80% yield) of the title compound was obtained in the same manner as described in Example 63, except that tert-butyl((5-chloro-2-fluoro-4-((2'-fluoro-4-(1-methyl-1H-pyrazol-4-yl)-[2,4'-bipyridin]-5-yl)oxy)phenyl)sulfonyl)(thiazol-4-yl)carbamate was used instead of tert-butyl((5-chloro-2-fluoro-4-((6-(2-fluorophenyl)-4-(1-methyl-1H-pyrazol-4-yl)pyridin-3-yl)oxy)phenyl)sulfonyl)(thiazol-4-yl)carbamate.

$^1$H NMR (CD$_3$OD, 500 MHz) δ 8.73 (s, 1H), 8.40 (s, 2H), 8.32 (m, 1H), 8.25 (d, 1H), 8.10 (m, 1H), 8.03 (m, 1H), 7.81 (s, 1H), 7.08 (s, 1H), 6.85 (d, 1H), 3.92 (s, 3H)

Example 69

Preparation of 5-chloro-2-fluoro-4-((2'-fluoro-4-(1-methyl-1H-pyrazol-4-yl)-[2,3'-bipyridin]-5-yl)oxy)-N-(thiazol-4-yl)benzenesulfonamide 2,2,2-trifluoroacetate

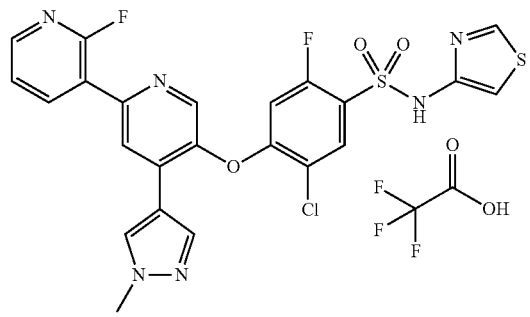

16 mg (80% yield) of the title compound was obtained in the same manner as described in Example 63, except that tert-butyl((5-chloro-2-fluoro-4-((2'-fluoro-4-(1-methyl-1H-pyrazol-4-yl)-[2,3'-bipyridin]-5-yl)oxy)phenyl)sulfonyl)(thiazol-4-yl)carbamate was used instead of tert-butyl((5-chloro-2-fluoro-4-((6-(2-fluorophenyl)-4-(1-methyl-1H-pyrazol-4-yl)pyridin-3-yl)oxy)phenyl)sulfonyl)(thiazol-4-yl)carbamate.

$^1$H NMR (CD$_3$OD, 500 MHz) δ 8.73 (s, 1H), 8.46 (m, 2H), 8.30 (m, 1H), 8.25 (m, 2H), 8.03 (m, 2H), 7.50 (s, 1H), 7.08 (s, 1H), 6.90 (m, 1H), 3.91 (s, 3H)

Example 70

Preparation of 5-chloro-2-fluoro-4-((6'-fluoro-4-(1-methyl-1H-pyrazol-4-yl)-[2,3'-bipyridin]-5-yl)oxy)-N-(thiazol-4-yl)benzenesulfonamide 2,2,2-trifluoroacetate

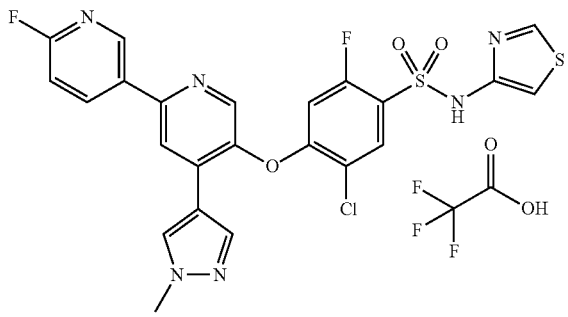

16 mg (80% yield) of the title compound was obtained in the same manner as described in Example 63, except that tert-butyl((5-chloro-2-fluoro-4-((6'-fluoro-4-(1-methyl-1H-pyrazol-4-yl)-[2,3'-bipyridin]-5-yl)oxy)phenyl)sulfonyl)(thiazol-4-yl)carbamate was used instead of tert-butyl((5-chloro-2-fluoro-4-((6-(2-fluorophenyl)-4-(1-methyl-1H-pyrazol-4-yl)pyridin-3-yl)oxy)phenyl)sulfonyl)(thiazol-4-yl)carbamate.

¹H NMR (CD₃OD, 500 MHz) δ 8.91 (m, 1H), 8.72 (m, 1H), 8.61 (m, 1H), 8.41 (m, 1H), 8.31 (m, 1H), 8.25 (m, 1H), 8.09 (m, 2H), 7.22 (m, 1H), 7.07 (m, 1H), 6.82 (m, 1H), 3.90 (s, 3H)

Example 71

Preparation of 5-chloro-2-fluoro-4-((6-(3-fluorophenyl)-4-(1-methyl-1H-pyrazol-5-yl)pyridin-3-yl)oxy)-N-(thiazol-4-yl)benzenesulfonamide

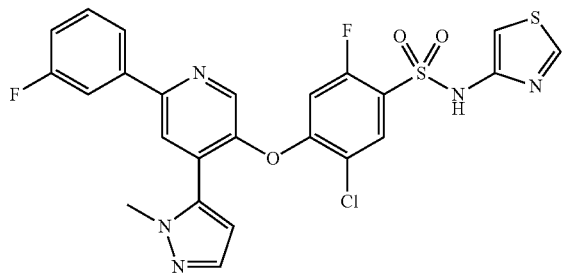 [SMILES: Cn1nccc1-c1cc(-c2cccc(F)c2)ncc1Oc1cc(F)c(S(=O)(=O)Nc2cscn2)cc1Cl]

20 mg (0.03 mmol) of tert-butyl((5-chloro-4-((6-chloro-4-(1-methyl-1H-pyrazol-5-yl)pyridin-3-yl)oxy)-2-fluorophenyl)sulfonyl)(thiazol-4-yl)carbamate was dissolved in 3 mL of N,N-dimethylformamide, and 6.9 mg (0.05 mmol) of (3-fluorophenyl)boronic acid was added thereto, and then 3.8 mg (10 mol %) of Pd(PPh₃)₄, 10.5 mg (0.1 mmol) of Na₂CO₃, and 1 mL of H₂O were added thereto. After reacting with microwave reactor at 120° C. for 10 minutes, the solvent was removed, and the remaining material was diluted with ethyl acetate and the organic layer was separated, and washed with saturated sodium chloride. The organic layer was collected, dried with magnesium sulfate to remove water, and concentrated under reduced pressure, and the residue was purified by column chromatography (developing solvent, hexane:ethyl acetate=3:1) to obtain 5 mg (27% yield) of the title compound.

¹H NMR (CD₃OD, 500 MHz) δ 8.72 (s, 1H), 8.59 (s, 1H), 8.05 (s, 1H), 7.89 (m, 3H), 7.52 (m, 1H), 7.41 (m, 1H), 7.21 (m, 1H), 7.02 (m, 1H), 6.82 (m, 1H), 6.41 (s, 1H), 3.87 (s, 3H)

Example 72

Preparation of 5-chloro-2-fluoro-4-((6-(3-fluorophenyl)-4-(2-(piperazin-1-yl)pyrimidin-4-yl)pyridin-3-yl)oxy)-N-(thiazol-4-yl)benzenesulfonamide

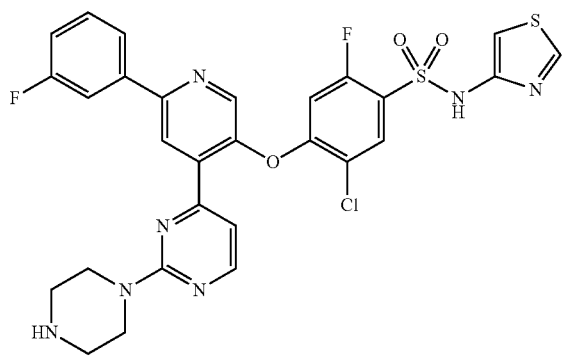

1000 mg (1 eq) of 6-chloropyridin-3-ol was dissolved in 50 mL of N,N-dimethylformamide, and 370 mg (1.2 eq) of sodium hydride was added thereto, followed by stirring at room temperature for 1 hour. Then, 688 uL (1.1 eq) of chloro (methoxy)methane was added slowly thereto, and the solution was stirred at room temperature for 2 hours. N,N-dimethylformamide was removed by concentrating under reduced pressure. After extracting with ethyl acetate, the extract was treated with anhydrous magnesium sulfate, and concentrated under reduced pressure. The residue was separated by column chromatography (developing solvent, hexane:ethyl acetate=9:1) to obtain 1200 mg of 2-chloro-5-(methoxymethoxy)pyridine.

200 mg (1.0 eq) of the obtained 2-chloro-5-(methoxymethoxy)pyridine was dissolved in N,N-dimethylformamide/H₂O=5:1 (16 mL), 193 mg (1.2 eq) of (3-fluorophenyl)boronic acid, 48 mg (3 mol %) of Pd(PPh₃)₄ and 586 mg (4.0 eq) of Na₂CO₃ were added. After reacting with microwave reactor at 120° C. for 30 minutes, N,N-dimethylformamide was removed by concentrating under reduced pressure. After extracting with ethyl acetate, the extract was treated with anhydrous magnesium sulfate, and concentrated under reduced pressure. The residue was separated by column chromatography (developing solvent, hexane:ethyl acetate=9:1) to obtain 220 mg of 2-(3-fluorophenyl)-5-(methoxymethoxy)pyridine.

100 mg (1.0 eq) of the obtained 2-(3-fluorophenyl)-5-(methoxymethoxy)pyridine was dissolved in 4.3 mL of tetrahydrofuran. After cooling to −78° C., tert-butyllithium 1.7 M solution (0.5 mL, 2.0 eq) was added slowly. The mixture was stirred at the same temperature for 30 minutes. 121 mg (1.5 eq) of B(O-iPr)₃ was dissolved in 2.1 mL of tetrahydrofuran, and added to the above mixture. The mixture was stirred at the same temperature for 1 hour, and stirred for 3 hours as warming to room temperature. After quenching by adding distilled water, tetrahydrofuran solution was added, and washed with brine. The reaction solution was dried with magnesium sulfate to remove water, concentrated under reduced pressure, and crystallized with methylchloride to obtain 50 mg of (2-(3-fluorophenyl)-5-hydroxypyridin-4-yl)boronic acid as white solid.

15.0 mg (1.0 eq) of the obtained (2-(3-fluorophenyl)-5-hydroxypyridin-4-yl)boronic acid was dissolved in 4.3 mL of 1,4-dioxane/H₂O=1:1 (1.0 mL), and 11.7 mg (1.0 eq) of (2-(3-fluorophenyl)-5-hydroxypyridin-4-yl)boronic acid, 1.74 mg (3 mol %) of Pd(PPh₃)₄ and 16.0 mg (3.0 eq) of Na₂CO₃ were added. After reacting with microwave reactor at 120° C. for 5 minutes, 1,4-dioxane was removed by concentrating under reduced pressure. After extracting with ethyl acetate, the extract was treated by anhydrous magnesium sulfate, and concentrated under reduced pressure. The residue was separated by column chromatography (developing solvent, hexane:ethyl acetate=4:1) to obtain 10.0 mg of tert-butyl 4-(4-(2-(3-fluorophenyl)-5-hydroxypyridin-4-yl)pyrimidin-2-yl)piperazine-1-carboxylate.

10.0 mg (1.0 eq) of the obtained tert-butyl 4-(4-(2-(3-fluorophenyl)-5-hydroxypyridin-4-yl)pyrimidin-2-yl)piperazin-1-carboxylate and 9.1 mg (1.0 eq) of the obtained tert-butyl((5-chloro-2,4-difluorophenyl)sulfonyl)(thiazol-4-yl)carbamate were dissolved in 0.2 mL of N,N-dimethylformamide 0.2 mL, then 21.6 mg (3.0 eq) of Cs₂CO₃ was added thereto. The mixture was reacted at room temperature for 16 hours. The solvent was removed by concentrating under reduced pressure. The residue was separated by PLC (developing solvent, hexane:ethyl acetate=2:1) to obtain 10 mg of tert-butyl 4-(4-(5-(4-(N-(tert-butoxycarbonyl)-N-(thiazol-4-yl)sulfamoyl)-2-chloro-5-fluorophenoxy)-2-(3-fluorophenyl)pyridin-4-yl)pyrimidin-2-yl)piperazin-1-carboxylate.

10 mg (1.0 eq) of the obtained tert-butyl 4-(4-(5-(4-(N-(tert-butoxycarbonyl)-N-(thiazol-4-yl)sulfamoyl)-2-chloro-5-fluorophenoxy)-2-(3-fluorophenyl)pyridin-4-yl)pyrimidin-2-yl)piperazin-1-carboxylate was dissolved in 0.2 oL dimethylchloride, and 0.2 mL of trifluoroacetic acid was added thereto. The mixture was reacted at room temperature for 2 hours. The solvent was removed by concentrating under reduced pressure. The residue was separated by PLC (developing solvent, dimethylchloride:methanol=15:1) to obtain 2.0 mg of 5-chloro-2-fluoro-4-((6-(3-fluorophenyl)-4-(2-(piperazin-1-yl)pyrimidin-4-yl)pyridin-3-yl)oxy)-N-(thiazol-4-yl)benzenesulfonamide.

$^1$H NMR (CDCl$_3$, 500 MHz) δ 8.70 (s, 1H), 8.59 (s, 1H), 8.47 (d, 1H), 8.25 (s, 1H), 7.93 (m, 2H), 7.87 (d, 1H), 7.53 (q, 1H), 7.21 (m, 1H), 7.11 (d, 1H), 6.85 (d, 1H), 6.76 (d, 1H), 4.62 (br, 1H), 3.80 (br, 4H), 3.07 (t, 4H)

Example 73

Preparation of 5-chloro-2-fluoro-4-((6'-(3-fluorophenyl)-[3,4'-bibyridin]-3'-yl)oxy)-N-(thiazol-2-yl)benzenesulfonamide

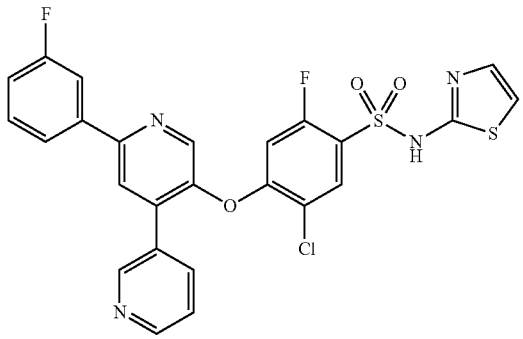 [SMILES: O=S(=O)(Nc1nccs1)c1cc(Cl)c(Oc2cnc(-c3cccc(F)c3)cc2-c2cccnc2)cc1F]

20 mg (0.03 mmol) of tert-butyl((5-chloro-4-((6'-chloro-[3,4'-bipyridin]-3'-yl)oxy)-2-fluorophenyl)sulfonyl)(thiazol-2-yl)carbamate was dissolved in 3 mL of N,N-dimethylformamide, and 7 mg (0.05 mmol) of (3-fluorophenyl)boronic acid was added thereto, and then 3.8 mg (10 mol %) of Pd(PPh$_3$)$_4$, 10.6 mg (0.10 mmol) of Na$_2$CO$_3$, and 1 mL of H$_2$O were added thereto. After reacting with microwave reactor at 120° C. for 10 minutes, the solvent was removed, and the remaining material was diluted with ethyl acetate and the organic layer was separated, and washed with saturated sodium chloride. The organic layer was collected, dried with magnesium sulfate to remove water, and concentrated under reduced pressure, and the residue was purified by column chromatography (developing solvent, hexane:ethyl acetate=3:1) to obtain 5 mg (27% yield) of the title compound.

$^1$H NMR (CD$_3$OD, 500 MHz) δ 8.88 (m, 1H), 8.60 (s, 1H), 8.55 (m, 1H), 8.18 (m, 1H), 8.07 (s, 1H), 7.93 (m, 1H), 7.90 (m, 1H), 7.54 (m, 3H), 7.21 (m, 1H), 6.97 (m, 1H), 6.71 (s, 1H)

Example 74

Preparation of 5-chloro-2-fluoro-4-((6'-(3-fluorophenyl)-[3,4'-bibyridin]-3'-yl)oxy)-N-(thiazol-4-yl)benzenesulfonamide

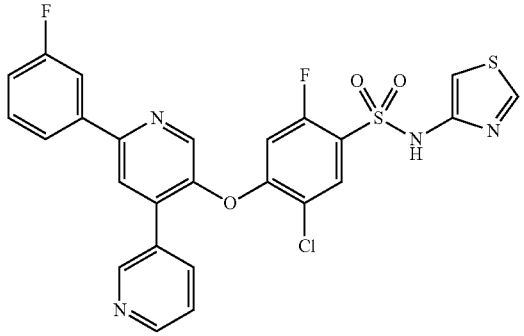 [SMILES: O=S(=O)(Nc1cscn1)c1cc(Cl)c(Oc2cnc(-c3cccc(F)c3)cc2-c2cccnc2)cc1F]

20 mg (0.03 mmol) of tert-butyl((5-chloro-4-((6'-chloro-[3,4'-bibyridin]-3'-yl)oxy)-2-fluorophenyl)sulfonyl)(thiazol-4-yl)carbamate was dissolved in 3 mL of N,N-dimethylformamide, and 3.8 mg (10 mol %) of (3-fluorophenyl)boronic acid was added thereto, and then 8.3 mg (3 mol %) of Pd(PPh$_3$)$_4$, 10.6 mg (0.10 mmol) of Na$_2$CO$_3$, and 1 mL of H$_2$O were added thereto. After reacting with microwave reactor at 120° C. for 10 minutes, the solvent was removed, and the remaining material was diluted with ethyl acetate and the organic layer was separated, and washed with saturated sodium chloride. The organic layer was collected, dried with magnesium sulfate to remove water, and concentrated under reduced pressure, and the residue was purified by column chromatography (developing solvent, hexane:ethyl acetate=3:1) to obtain 5 mg (27% yield) of the title compound.

$^1$H NMR (CD$_3$OD, 500 MHz) δ 8.82 (m, 1H), 8.72 (m, 1H), 8.54 (m, 2H), 8.13 (m, 2H), 7.92 (m, 3H), 7.62 (m, 1H), 7.54 (m, 1H), 7.20 (m, 1H), 7.00 (m, 1H), 6.82 (d, 1H)

Example 75

Preparation of 5-chloro-2-fluoro-4-((2''-fluoro-[3,4':2',4''-terpyridin]-5'-yl)oxy)-N-(thiazol-4-yl)benzenesulfonamide

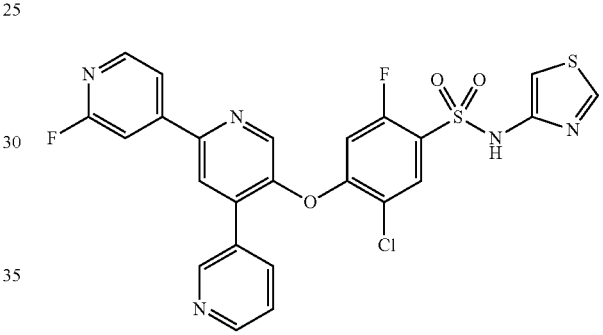

16 mg (80% yield) of the title compound was obtained in the same manner as described in Example 74, except that (2-fluoropyridin-4-yl)boronic acid was used instead of (3-fluorophenyl)boronic acid.

$^1$H NMR (CD$_3$OD/CDCl$_3$, 500 MHz) δ 8.82 (s, 1H), 8.73 (s, 1H), 8.60 (s, 1H), 8.56 (m, 1H), 8.32 (m, 2H), 8.15 (m, 1H), 8.07 (m, 1H), 7.91 (m, 1H), 7.84 (s, 1H), 7.50 (m, 1H), 7.01 (s, 1H), 6.89 (d, 1H)

Example 76

Preparation of 5-chloro-2-fluoro-4-((6-(3-fluorophenyl)-4-(pyrimidin-5-yl)pyridin-3-yl)oxy)-N-(thiazol-4-yl)benzenesulfonamide

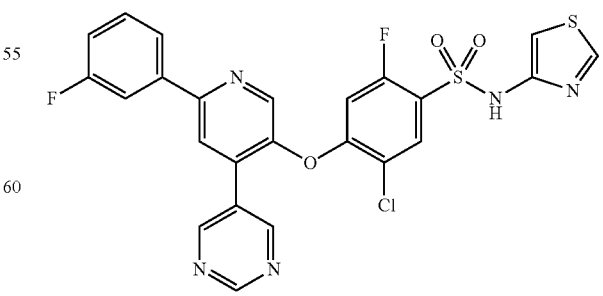

20 mg (0.03 mmol) of tert-butyl((5-chloro-4-((6-chloro-4-(pyrimidin-5-yl)pyridin-3-yl)oxy)-2-fluorophenyl)sulfonyl)

(thiazol-4-yl)carbamate was dissolved in 3 mL of N,N-dimethylformamide, and 7 mg (0.05 mmol) of (3-fluorophenyl)boronic acid was added thereto, and then 3.8 mg (10 mol %) of Pd(PPh$_3$)$_4$, 10.6 mg (0.10 mmol) of Na$_2$CO$_3$, and 1 mL of H$_2$O were added thereto. After reacting with microwave reactor at 120° C. for 10 minutes, the solvent was removed, and the remaining material was diluted with ethyl acetate and the organic layer was separated, and washed with saturated sodium chloride. The organic layer was collected, dried with magnesium sulfate to remove water, and concentrated under reduced pressure, and the residue was purified by column chromatography (developing solvent, hexane:ethyl acetate=3:1) to obtain 5 mg (27% yield) of the title compound.

$^1$H NMR (CD$_3$OD, 500 MHz) δ 9.17 (s, 1H), 9.11 (m, 2H), 8.74 (m, 1H), 8.54 (s, 1H), 8.21 (s, 1H), 7.93 (m, 3H), 7.52 (m, 1H), 7.20 (m, 1H), 7.04 (m, 1H), 6.95 (d, 1H)

Example 77

Preparation of 5-chloro-2-fluoro-4-((2'-fluoro-4-(pyrimidin-5-yl)-[2,4'-bipyridin]-5-yl)oxy)-N-(thiazol-4-yl)benzenesulfonamide

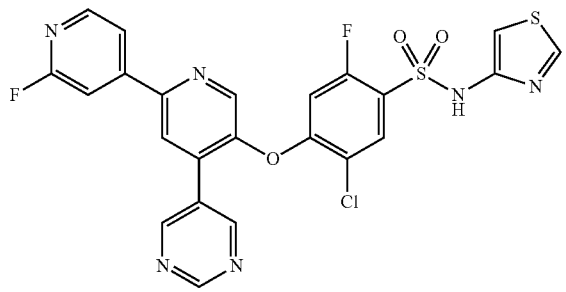 [SMILES: O=S(=O)(Nc1cscn1)c1cc(Cl)c(Oc2cnc(-c3ccnc(F)c3)cc2-c2cncnc2)cc1F]

16 mg (80% yield) of the title compound was obtained in the same manner as described in Example 76, except that (2-fluoropyridin-4-yl)boronic acid was used instead of (3-fluorophenyl)boronic acid.

$^1$H NMR (CD$_3$OD/CDCl$_3$, 500 MHz) δ 9.19 (s, 1H), 9.14 (s, 2H, 8.74 (m, 1H), 8.59 (s, 1H), 8.39 (m, 1H), 8.33 (m, 1H), 8.06 (m, 1H), 7.95 (m, 1H), 7.85 (m, 1H), 7.05 (m, 2H)

Example 78

Preparation of 5-chloro-2-fluoro-4-((6-(3-fluorophenyl)-4-(1H-pyrazol-4-yl)pyridin-3-yl)oxy)-N-(thiazol-4-yl)benzenesulfonamide

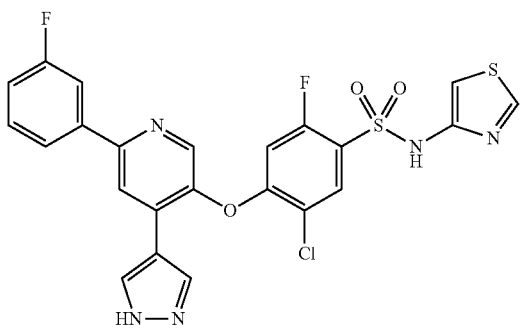 [SMILES: O=S(=O)(Nc1cscn1)c1cc(Cl)c(Oc2cnc(-c3cccc(F)c3)cc2-c2cn[nH]c2)cc1F]

13.9 mg (0.03 mmol) of 5-chloro-4-((6-chloro-4-(1H-pyrazol-4-yl)pyridin-3-yl)oxy)-2-fluoro-N-(thiazol-4-yl)benzenesulfonamide was dissolved in 1 mL of 1,4-dioxane, and 6.3 mg (0.05 mmol) of (3-fluorophenyl)boronic acid was added thereto, and then 3.5 mg (10 mol %) of Pd(PPh$_3$)$_4$, 12.4 mg (0.09 mmol) of Na$_2$CO$_3$, and 0.2 mL of H$_2$O were added thereto. After reacting with microwave reactor at 120° C. for 20 minutes, the solvent was removed, and the remaining material was diluted with ethyl acetate and the organic layer was separated, and washed with saturated sodium chloride. The organic layer was collected, dried with magnesium sulfate to remove water, and concentrated under reduced pressure, and the residue was purified by column chromatography (developing solvent, dimethylchloride:ethanol=15:1) to obtain 3.2 mg (19.7% yield) of the title compound.

$^1$H NMR (CD$_3$OD, 500 MHz) δ 6.73 (1H), 7.05 (1H), 7.19 (1H), 7.51 (1H), 7.85 (1H), 7.91 (1H), 8.00 (1H), 8.23 (3H), 8.39 (1H), 7.81 (1H)

Example 79

Preparation of 5-chloro-2-fluoro-4-((2'-fluoro-6-(3-fluorophenyl)-[4,4'-bipyridin]-3-yl)oxy)-N-(thiazol-4-yl)benzenesulfonamide

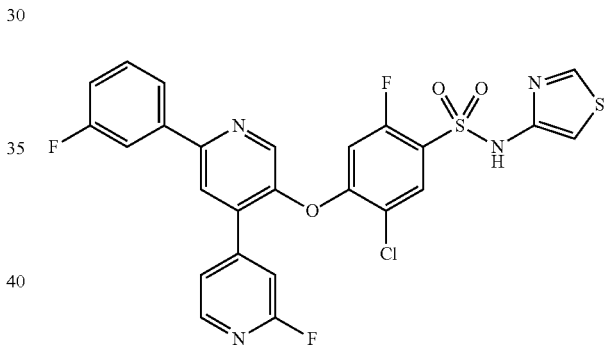

20 mg (0.03 mmol) of tert-butyl((5-chloro-4-((6-chloro-2'-fluoro-[4,4'-bipyridin]-3-yl)oxy)-2-fluorophenyl)sulfonyl)(thiazol-4-yl)carbamate was dissolved in 3 mL of N,N-dimethylformamide, and 6.8 mg (0.05 mmol) of (3-fluorophenyl)boronic acid was added thereto, and then 3.7 mg (10 mol %) of Pd(PPh$_3$)$_4$, 10 mg (0.10 mmol) of Na$_2$CO$_3$, and 1 mL of H$_2$O were added thereto. After reacting with microwave reactor at 120° C. for 5 minutes, the solvent was removed, and the remaining material was diluted with ethyl acetate and the organic layer was separated, and washed with saturated sodium chloride. The organic layer was collected, dried with magnesium sulfate to remove water, and concentrated under reduced pressure, and the residue was purified by column chromatography (developing solvent, hexane:ethyl acetate=3:1) to obtain 5 mg (27% yield) of the title compound.

$^1$H NMR (CD$_3$OD, 500 MHz) δ 8.72 (m, 1H), 8.54 (s, 1H), 8.24 (d, 1H), 8.12 (m, 1H), 7.87 (m, 3H), 7.57 (m, 1H), 7.52 (m, 1H), 7.49 (m, 1H), 7.21 (m, 1H), 7.02 (m, 1H), 6.87 (d, 1H)

Example 80

Preparation of 5-chloro-4-((6-(3,4-difluorophenyl)-2'-fluoro-[4,4'-bipyridin]-3-yl)oxy)-2-fluoro-N-(thiazol-4-yl)benzenesulfonamide

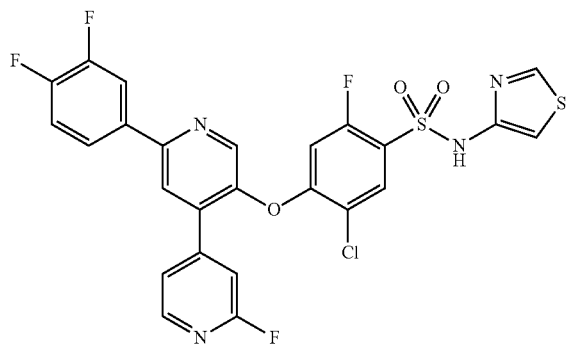 [SMILES: O=S(=O)(Nc1cscn1)c1cc(Cl)c(Oc2cnc(-c3ccc(F)c(F)c3)cc2-c2ccnc(F)c2)cc1F]

16 mg (80% yield) of the title compound was obtained in the same manner as described in Example 79, except that (3,4-fluorophenyl)boronic acid was used instead of (3-fluorophenyl)boronic acid.

$^1$H NMR (CD$_3$OD/CDCl$_3$, 500 MHz) δ 8.72 (s, 1H), 8.53 (s, 1H), 8.24 (m, 1H), 8.11 (m, 2H), 7.91 (m, 2H), 7.56 (m, 1H), 7.40 (m, 2H), 7.01 (s, 1H), 6.88 (d, 1H)

Example 81

Preparation of 5-chloro-4-((6'-(5-chloro-2-fluorophenyl)-[3,4'-bipyridin]-3'-yl)oxy)-2-fluoro-N-(thiazol-4-yl)benzenesulfonamide

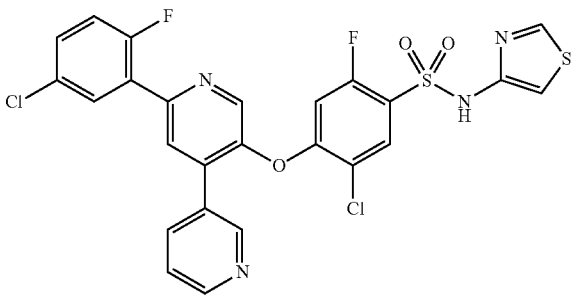 [SMILES: O=S(=O)(Nc1cscn1)c1cc(Cl)c(Oc2cnc(-c3cc(Cl)ccc3F)cc2-c2cccnc2)cc1F]

16 mg (80% yield) of the title compound was obtained in the same manner as described in Example 74, except that (5-chloro-2-fluorophenyl)boronic acid was used instead of (3-fluorophenyl)boronic acid.

$^1$H NMR (CD$_3$OD/CDCl$_3$, 500 MHz) δ 8.96 (s, 1H), 8.87 (s, 1H), 8.70 (s, 1H), 8.58 (m, 1H), 8.12 (m, 4H), 7.70 (s, 1H), 7.52 (m, 2H), 7.30 (m, 1H), 6.98 (d, 1H)

Example 82

Preparation of 5-chloro-4-((6'-(3,4-difluorophenyl)-[3,4'-bipyridin]-3'-yl)oxy)-2-fluoro-N-(thiazol-4-yl)benzenesulfonamide

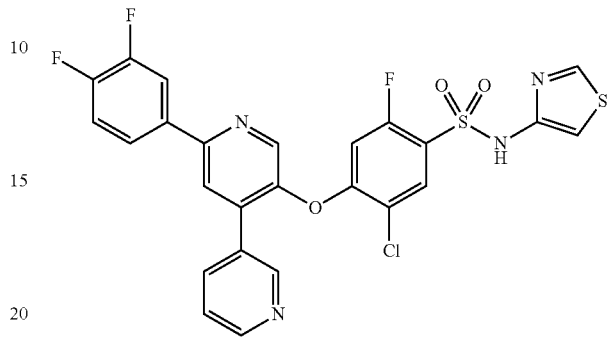

16 mg (80% yield) of the title compound was obtained in the same manner as described in Example 74, except that (3,4-fluorophenyl)boronic acid was used instead of (3-fluorophenyl)boronic acid.

$^1$H NMR (CD$_3$OD/CDCl$_3$, 500 MHz) δ 8.82 (s, 1H), 8.71 (s, 1H), 8.53 (s, 2H), 8.11 (m, 3H), 7.94 (m, 1H), 7.87 (d, 1H), 7.47 (m, 1H), 7.40 (m, 1H), 6.95 (s, 1H), 6.80 (d, 1H)

Example 83

Preparation of 3-cyano-4-((6-(3-fluorophenyl)-4-(1H-pyrazol-4-yl)pyridin-3-yl)oxy)-N-(thiazol-4-yl)benzenesulfonamide

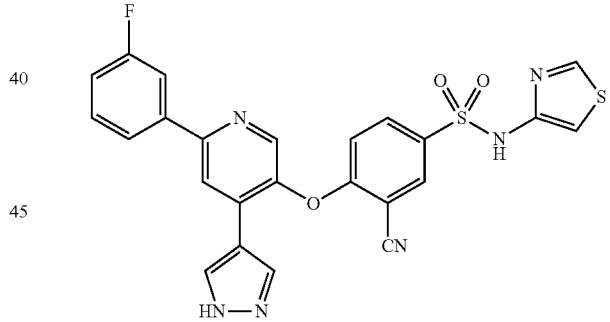

25.0 mg (0.05 mmol) of 4-((6-chloro-4-(1H-pyrazol-4-yl)pyridin-3-yl)oxy)-3-cyano-N-(thiazol-4-yl)benzenesulfonamide was dissolved in 1.5 mL of 1,4-dioxane, and 10.5 mg (0.08 mmol) of (3-fluorophenyl)boronic acid was added thereto, and then 5.8 mg (10 mol %) of Pd(PPh$_3$)$_4$, 20.7 mg (0.15 mmol) of K$_2$CO$_3$, and 0.3 mL of H$_2$O were added thereto. After reacting with microwave reactor at 120° C. for 20 minutes, the solvent was removed, and the remaining material was diluted with ethyl acetate and the organic layer was separated, and washed with saturated sodium chloride. The organic layer was collected, dried with magnesium sulfate to remove water, and concentrated under reduced pressure, and the residue was purified by column chromatography (developing solvent, hexane:ethyl acetate=1:1) to obtain 9.0 mg (31.9% yield) of the title compound.

$^1$H NMR (CD$_3$OD, 500 MHz) δ 6.92 (1H), 7.07 (1H), 7.19 (1H), 7.53 (1H), 7.86 (1H), 7.92 (2H), 8.26 (4H), 8.49 (1H), 8.71 (1H)

Example 84

Preparation of 3-cyano-4-((6'-(3-fluorophenyl)-[3,4'-bipyridin]-3'-yl)oxy)-N-(thiazol-4-yl)benzenesulfonamide

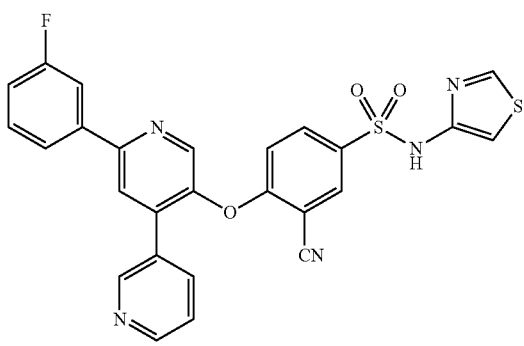 [SMILES: N#Cc1cc(S(=O)(=O)Nc2cscn2)ccc1Oc1cnc(-c2cccc(F)c2)cc1-c1cccnc1]

10 mg (0.03 mmol) of tert-butyl((4-((6'-chloro-[3,4'-bipyridin]-3'-yl)oxy)-3-cyanophenyl)sulfonyl)(thiazol-4-yl)carbamate was dissolved in 3 mL of N,N-dimethylformamide, and 3.7 mg (0.03 mmol) of (3-fluorophenyl)boronic acid was added thereto, and then 2 mg (10 mol %) of Pd(PPh$_3$)$_4$, 5.6 mg (0.05 mmol) of Na$_2$CO$_3$, and 1 mL of H$_2$O were added thereto. After reacting with microwave reactor at 120° C. for 5 minutes, the solvent was removed, and the remaining material was diluted with ethyl acetate and the organic layer was separated, and washed with saturated sodium chloride. The organic layer was collected, dried with magnesium sulfate to remove water, and concentrated under reduced pressure, and the residue was purified by column chromatography (developing solvent, hexane:ethyl acetate=3:1) to obtain 5 mg (27% yield) of the title compound.

$^1$H NMR (CD$_3$OD, 500 MHz) δ 8.79 (s, 1H), 8.71 (m, 1H), 8.67 (s, 1H), 8.52 (m, 1H), 8.13 (m, 3H), 7.91 (m, 3H), 7.51 (m, 1H), 7.48 (m, 1H), 7.21 (m, 1H), 7.19 (m, 1H), 6.95 (d, 1H)

Example 85

Preparation of 3-cyano-4-((6'-(3,4-difluorophenyl)-[3,4'-bipyridin]-3'-yl)oxy)-N-(thiazol-4-yl)benzenesulfonamide

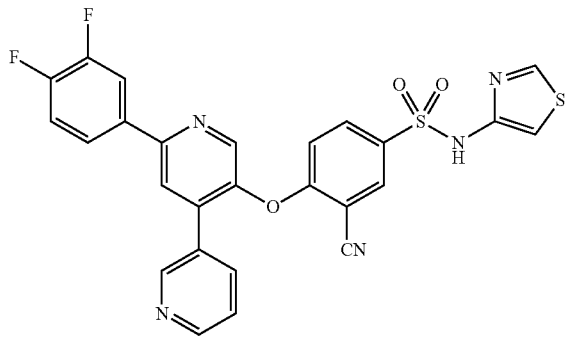 [SMILES: N#Cc1cc(S(=O)(=O)Nc2cscn2)ccc1Oc1cnc(-c2ccc(F)c(F)c2)cc1-c1cccnc1]

16 mg (80% yield) of the title compound was obtained in the same manner as described in Example 84, except that (3,4-fluorophenyl)boronic acid was used instead of (3-fluorophenyl)boronic acid.

$^1$H NMR (CD$_3$OD/CDCl$_3$, 500 MHz) δ 8.78 (s, 1H), 8.72 (s, 1H), 8.65 (s, 1H), 8.52 (m, 1H), 8.12 (m, 4H), 7.99 (m, 1H), 7.88 (m, 1H), 7.46 (m, 1H), 7.39 (m, 1H), 7.02 (s, 1H), 6.93 (d, 1H)

Example 86

Preparation of 3-cyano-4-((6'-(3-fluoro-4-(trifluoromethyl)phenyl)-[3,4'-bipyridin]-3'-yl)oxy)-N-(thiazol-4-yl)benzenesulfonamide

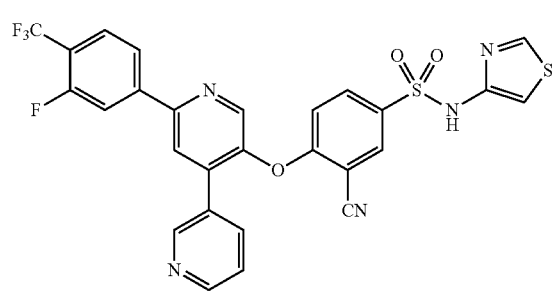 [SMILES: N#Cc1cc(S(=O)(=O)Nc2cscn2)ccc1Oc1cnc(-c2ccc(C(F)(F)F)c(F)c2)cc1-c1cccnc1]

16 mg (80% yield) of the title compound was obtained in the same manner as described in Example 84, except that (3-fluoro-4-(trifluoromethyl)phenyl)boronic acid was used instead of (3-fluorophenyl)boronic acid.

$^1$H NMR (CD$_3$OD/CDCl$_3$, 500 MHz) δ 8.81 (s, 1H), 8.71 (s, 2H), 8.53 (m, 1H), 8.27 (m, 1H), 8.12 (m, 4H), 7.88 (m, 2H), 7.49 (m, 1H), 7.01 (m, 2H)

Example 87

Preparation of 2,5-difluoro-4-((6'-(3-fluorophenyl)-[3,4'-bipyridin]-3'-yl)oxy)-N-(thiazol-4-yl)benzenesulfonamide

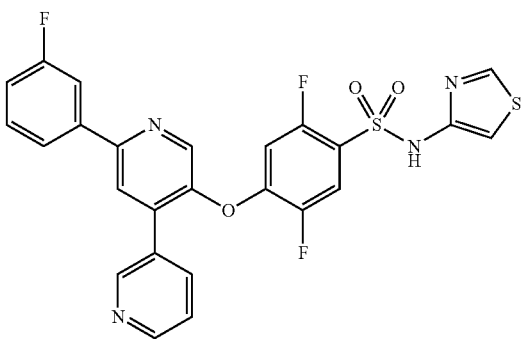 [SMILES: O=S(=O)(Nc1cscn1)c1cc(F)c(Oc2cnc(-c3cccc(F)c3)cc2-c2cccnc2)cc1F]

10 mg (0.03 mmol) of tert-butyl((4-((6'-chloro-[3,4'-bipyridin]-3'-yl)oxy)-2,5-difluorophenyl)sulfonyl)(thiazol-4-yl)carbamate was dissolved in 3 mL of N,N-dimethylformamide, and 3.7 mg (0.03 mmol) of (3-fluorophenyl)boronic acid was added thereto, and then 2 mg (10 mol %) of Pd(PPh$_3$)$_4$, 5.5 mg (0.05 mmol) of Na$_2$CO$_3$, and 1 mL of H$_2$O were added thereto. After reacting with microwave reactor at 120° C. for 10 minutes, the solvent was removed, and the remaining material was diluted with ethyl acetate and the organic layer was separated, and washed with saturated sodium chloride. The organic layer was collected, dried with magnesium sulfate to remove water, and concentrated under reduced pressure, and the residue was purified by column chromatography (developing solvent, hexane:ethyl acetate=3:1) to obtain 5 mg (27% yield) of the title compound.

$^1$H NMR (CD$_3$OD, 500 MHz) δ 8.81 (m, 1H), 8.73 (m, 1H), 8.54 (m, 2H), 8.12 (m, 2H), 7.91 (d, 1H), 7.86 (m, 1H), 7.68 (m, 1H), 7.50 (m, 2H), 7.19 (m, 1H), 6.99 (m, 1H), 6.94 (m, 1H)

Example 88

Preparation of 4-((6'-(3,4-difluorophenyl)-[3,4'-bipyridin]-3'-yl)oxy)-2,5-difluoro-N-(thiazol-4-yl)benzenesulfonamide

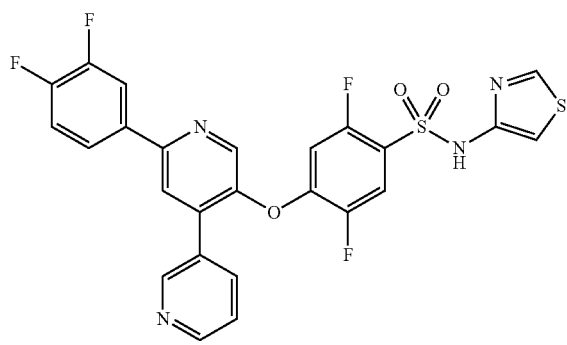 [SMILES: O=S(=O)(Nc1cscn1)c1cc(F)c(Oc2cnc(-c3ccc(F)c(F)c3)cc2-c2cccnc2)cc1F]

16 mg (80% yield) of the title compound was obtained in the same manner as described in Example 87, except that (3,4-fluorophenyl)boronic acid was used instead of (3-fluorophenyl)boronic acid.

$^1$H NMR (CD$_3$OD/CDCl$_3$, 500 MHz) δ 8.81 (s, 1H), 8.73 (s, 1H), 8.54 (m, 2H), 8.12 (m, 3H), 7.93 (m, 1H), 7.67 (m, 1H), 7.50 (m, 1H), 7.39 (m, 1H), 7.00 (s, 1H), 6.91 (m, 1H)

Example 89

Preparation of 2,5-difluoro-4-((6'-(3-fluoro-4-(trifluoromethyl)phenyl)-[3,4'-bipyridin]-3'-yl)oxy)-N-(thiazol-4-yl)benzenesulfonamide

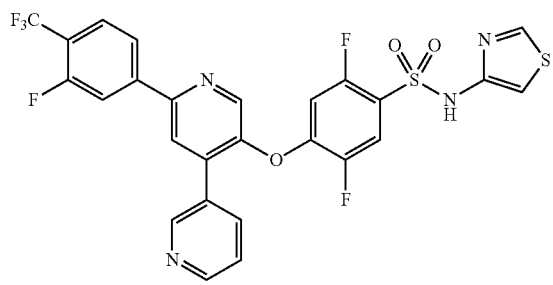 [SMILES: O=S(=O)(Nc1cscn1)c1cc(F)c(Oc2cnc(-c3ccc(C(F)(F)F)c(F)c3)cc2-c2cccnc2)cc1F]

16 mg (80% yield) of the title compound was obtained in the same manner as described in Example 87, except that (3-fluoro-4-(trifluoromethyl)phenyl)boronic acid was used instead of (3-fluorophenyl)boronic acid.

$^1$H NMR (CD$_3$OD/CDCl$_3$, 500 MHz) δ 8.83 (m, 1H), 8.78 (m, 1H), 8.56 (m, 2H), 8.21 (s, 1H), 8.12 (m, 3H), 7.81 (m, 1H), 7.68 (m, 1H), 7.51 (m, 1H), 6.96 (m, 2H)

Example 90

Preparation of 3-cyano-4-((6-(4-fluorophenyl)-4-(1H-pyrazol-4-yl)pyridin-3-yl)oxy)-N-(thiazol-4-yl)benzenesulfonamide

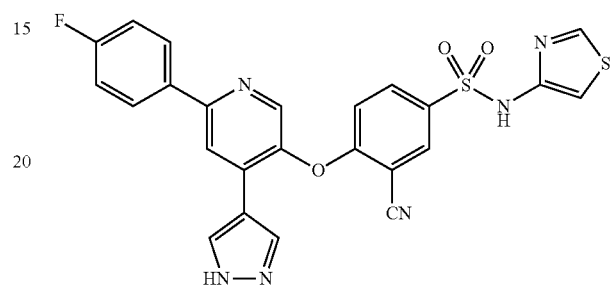

5.5 mg (29.5% yield) of the title compound was obtained in the same manner as described in Example 83, except that 4-((6-chloro-4-(1H-pyrazol-4-yl)pyridin-3-yl)oxy)-3-cyano-N-(thiazol-4-yl)benzenesulfonamide and (4-fluorophenyl)boronic acid were used instead of 4-((6-chloro-4-(1H-pyrazol-4-yl)pyridin-3-yl)oxy)-3-cyano-N-(thiazol-4-yl)benzenesulfonamide and (3-fluorophenyl)boronic acid.

$^1$H NMR (CD$_3$OD, 500 MHz) δ 6.91 (1H), 7.05 (1H), 7.24 (2H), 7.92 (1H), 8.12 (3H), 8.24 (3H), 8.47 (1H), 8.70 (1H)

Example 91

Preparation of 3-cyano-4-((6-(3,4-difluorophenyl)-4-(1H-pyrazol-4-yl)pyridin-3-yl)oxy)-N-(thiazol-4-yl)benzenesulfonamide

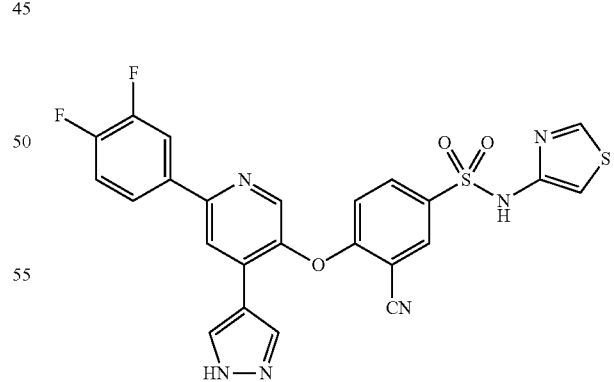

5.7 mg (29.5% yield) of the title compound was obtained in the same manner as described in Example 83, except that (3,4-difluorophenyl)boronic acid was used instead of (3-fluorophenyl)boronic acid.

$^1$H NMR (CD$_3$OD, 500 MHz) δ 6.91 (1H), 7.06 (1H), 7.40 (1H), 7.94 (2H), 8.07 (1H), 8.23 (4H), 8.49 (1H), 8.71 (1H)

Example 92

Preparation of 3-cyano-4-((6-(3-fluorophenyl)-4-(pyrimidin-5-yl)pyridin-3-yl)oxy)-N-(thiazol-4-yl)benzenesulfonamide

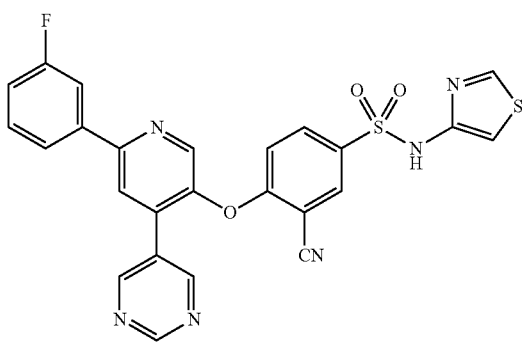 [SMILES: N#Cc1cc(S(=O)(=O)Nc2cscn2)ccc1Oc1cnc(-c2cccc(F)c2)cc1-c1cncnc1]

10 mg (0.02 mmol) of tert-butyl((4-((6-chloro-4-(pyrimidin-5-yl)pyridin-3-yl)oxy)-3-cyanophenyl)sulfonyl)(thiazol-4-yl)carbamate was dissolved in 3 mL of N,N-dimethylformamide, and 3.7 mg (0.03 mmol) of (3-fluorophenyl)boronic acid was added thereto, and then 2 mg (10 mol %) of Pd(PPh$_3$)$_4$, 5.5 mg (0.05 mmol) of Na$_2$CO$_3$, and 1 mL of H$_2$O were added thereto. After reacting with microwave reactor at 120° C. for 10 minutes, the solvent was removed, and the remaining material was diluted with ethyl acetate and the organic layer was separated, and washed with saturated sodium chloride. The organic layer was collected, dried with magnesium sulfate to remove water, and concentrated under reduced pressure, and the residue was purified by column chromatography (developing solvent, hexane:ethyl acetate=3:1) to obtain 80 mg (70% yield) of the title compound.

$^1$H NMR (CD$_3$OD, 500 MHz) δ 9.15 (s, 1H), 9.08 (s, 2H), 8.73 (s, 1H), 8.67 (s, 1H), 8.23 (s, 1H), 8.18 (m, 1H), 7.97 (m, 1H), 7.93 (m, 2H), 7.53 (m, 1H), 7.21 (m, 1H), 7.05 (m, 2H)

Example 93

Preparation of 3-cyano-4-((6-(3,4-difluorophenyl)-4-(pyrimidin-5-yl)pyridin-3-yl)oxy)-N-(thiazol-4-yl)benzenesulfonamide

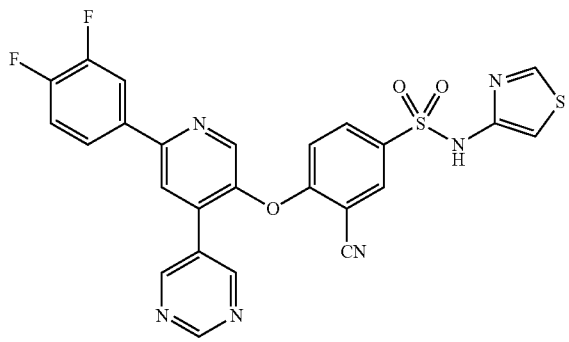 [SMILES: N#Cc1cc(S(=O)(=O)Nc2cscn2)ccc1Oc1cnc(-c2ccc(F)c(F)c2)cc1-c1cncnc1]

16 mg (80% yield) of the title compound was obtained in the same manner as described in Example 92, except that (3,4-fluorophenyl)boronic acid was used instead of (3-fluorophenyl)boronic acid.

$^1$H NMR (CD$_3$OD/CDCl$_3$, 500 MHz) δ 9.16 (s, 1H), 9.08 (s, 2H), 8.72 (s, 1H), 8.66 (s, 1H), 8.22 (s, 1H), 8.18 (s, 1H), 8.11 (m, 1H), 7.98 (m, 1H), 7.91 (m, 1H), 7.42 (m, 1H), 7.05 (m, 2H)

Example 94

Preparation of 3-cyano-4-((6-(3-fluoro-4-(trifluoromethyl)phenyl)-4-(pyrimidin-5-yl)pyridin-3-yl)oxy)-N-(thiazol-4-yl)benzenesulfonamide

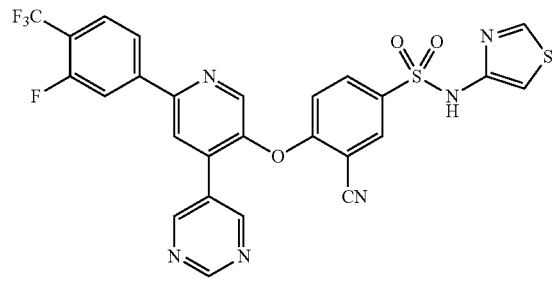 [SMILES: N#Cc1cc(S(=O)(=O)Nc2cscn2)ccc1Oc1cnc(-c2ccc(C(F)(F)F)c(F)c2)cc1-c1cncnc1]

16 mg (80% yield) of the title compound was obtained in the same manner as described in Example 92, except that (3-fluoro-4-(trifluoromethyl)phenyl)boronic acid was used instead of (3-fluorophenyl)boronic acid.

$^1$H NMR (CD$_3$OD/CDCl$_3$, 500 MHz) δ 9.17 (s, 1H), 9.10 (s, 2H), 8.73 (m, 2H), 8.35 (s, 1H), 8.19 (m, 3H), 7.94 (m, 1H), 7.83 (m, 1H), 7.09 (m, 2H)

Example 95

Preparation of 2,5-difluoro-4-((6-(3-fluorophenyl)-4-(pyrimidin-5-yl)pyridin-3-yl)oxy)-N-(thiazol-4-yl)benzenesulfonamide

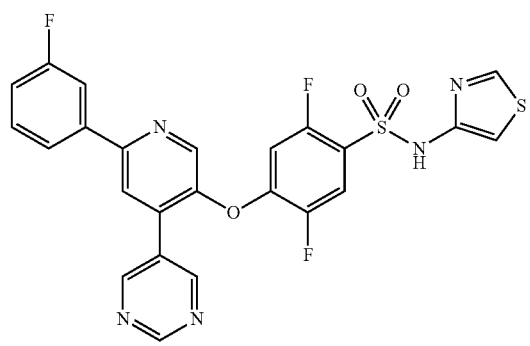 [SMILES: O=S(=O)(Nc1cscn1)c1cc(F)c(Oc2cnc(-c3cccc(F)c3)cc2-c2cncnc2)cc1F]

10 mg (0.02 mmol) of tert-butyl((4-((6-chloro-4-(pyrimidin-5-yl)pyridin-3-yl)oxy)-2,5-difluorophenyl)sulfonyl)(thiazol-4-yl)carbamate was dissolved in 3 mL of N,N-dimethylformamide, and 3.6 mg (0.03 mmol) of (3-fluorophenyl)boronic acid was added thereto, and then 2 mg (10 mol %) of Pd(PPh$_3$)$_4$, 5.4 mg (0.05 mmol) of Na$_2$CO$_3$, and 1 mL of H$_2$O were added thereto. After reacting with microwave reactor at 120° C. for 10 minutes, the solvent was removed, and the remaining material was diluted with ethyl acetate and the organic layer was separated, and washed with saturated sodium chloride. The organic layer was collected, dried with magnesium sulfate to remove water, and concentrated under reduced pressure, and the residue was purified by column chromatography (developing solvent, hexane:ethyl acetate=3:1) to obtain 5 mg (27% yield) of the title compound.

$^1$H NMR (CD$_3$OD, 500 MHz) δ 9.18 (s, 1H), 9.10 (s, 2H), 8.73 (s, 1H), 8.54 (s, 1H), 8.19 (s, 1H), 7.92 (m, 2H), 7.72 (m, 1H), 7.52 (m, 1H), 7.21 (m, 1H), 7.09 (m, 1H), 7.01 (s, 1H)

Example 96

Preparation of 4-((6-(3,4-difluorophenyl)-4-(pyrimidin-5-yl)pyridin-3-yl)oxy)-2,5-difluoro-N-(thiazol-4-yl)benzenesulfonamide

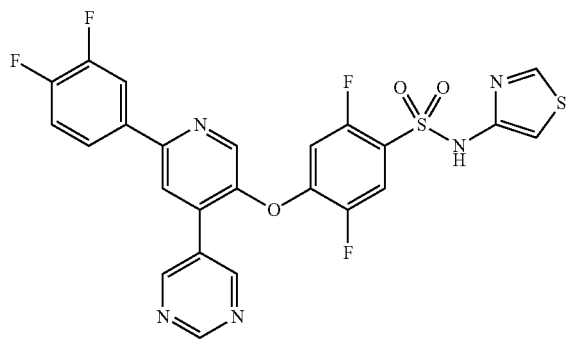 [SMILES: O=S(=O)(Nc1cscn1)c1cc(F)c(Oc2cnc(-c3ccc(F)c(F)c3)cc2-c2cncnc2)cc1F]

16 mg (80% yield) of the title compound was obtained in the same manner as described in Example 95, except that (3,4-difluorophenyl)boronic acid was used instead of (3-fluorophenyl)boronic acid.

$^1$H NMR (CD$_3$OD/CDCl$_3$, 500 MHz) δ 9.18 (s, 1H), 9.10 (s, 2H), 8.73 (s, 1H), 8.53 (s, 1H), 8.17 (s, 1H), 8.08 (m, 1H), 7.95 (m, 1H), 7.73 (m, 1H), 7.38 (m, 1H), 7.08 (m, 1H), 7.01 (s, 1H)

Example 97

Preparation of 2,5-difluoro-4-((6-(3-fluoro-4-(trifluoromethyl)phenyl)-4-(pyrimidin-5-yl)pyridin-3-yl)oxy)-N-(thiazol-4-yl)benzenesulfonamide

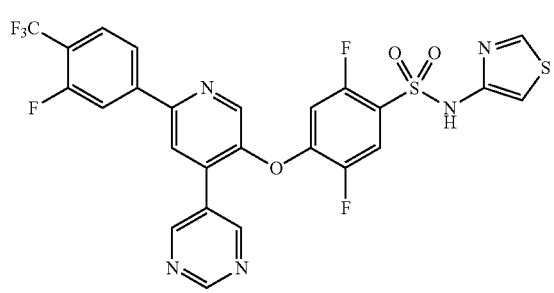 [SMILES: O=S(=O)(Nc1cscn1)c1cc(F)c(Oc2cnc(-c3ccc(C(F)(F)F)c(F)c3)cc2-c2cncnc2)cc1F]

16 mg (80% yield) of the title compound was obtained in the same manner as described in Example 95, except that (3-fluoro-4-(trifluoromethyl)phenyl)boronic acid was used instead of (3-fluorophenyl)boronic acid.

$^1$H NMR (CD$_3$OD/CDCl$_3$, 500 MHz) δ 9.19 (s, 1H), 9.12 (s, 2H), 8.73 (s, 1H), 8.57 (s, 1H), 8.30 (s, 1H), 8.14 (m, 2H), 7.82 (m, 1H), 7.77 (m, 1H), 7.14 (m, 1H), 7.02 (s, 1H)

Example 98

Preparation of 5-chloro-4-((6-(3,4-difluorophenyl)-4-(1H-pyrazol-4-yl)pyridin-3-yl)oxy)-2-fluoro-N-(thiazol-4-yl)benzenesulfonamide

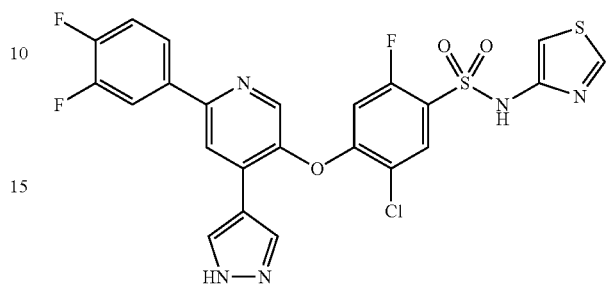

15.0 mg (0.03 mmol) of 5-chloro-4-((6-chloro-4-(1H-pyrazol-4-yl)pyridin-3-yl)oxy)-2-fluoro-N-(thiazol-4-yl)benzenesulfonamide was dissolved in 1.5 mL of 1,4-dioxane, and 7.1 mg (0.05 mmol) of (3,4-difluorophenyl)boronic acid was added thereto, and then 3.5 mg (10 mol %) of Pd(PPh$_3$)$_4$, 12.4 mg (0.09 mmol) of K$_2$CO$_3$, and 0.3 mL of H$_2$O were added thereto. After reacting with microwave reactor at 150° C. for 30 minutes, the solvent was removed, and the remaining material was diluted with ethyl acetate and the organic layer was separated, and washed with saturated sodium chloride. The organic layer was collected, dried with magnesium sulfate to remove water, and concentrated under reduced pressure, and the residue was purified by column chromatography (developing solvent, dimethylchloride:methanol=20:1) to obtain 9.0 mg (31.9% yield) of the title compound.

$^1$H NMR (DMSO-d$_6$, 500 MHz) δ 8.86 (1H), 8.59 (1H), 8.35 (1H), 8.04 (2H), 7.88 (3H), 7.37 (1H), 7.17 (1H), 6.31 (1H)

Example 99

Preparation of 5-chloro-2-fluoro-4-((6'-(3-fluorophenyl)-5-(pyrrolidin-1-yl)-[3,4'-bipyridin]-3'-yl)oxy)-N-(thiazol-4-yl)benzenesulfonamide

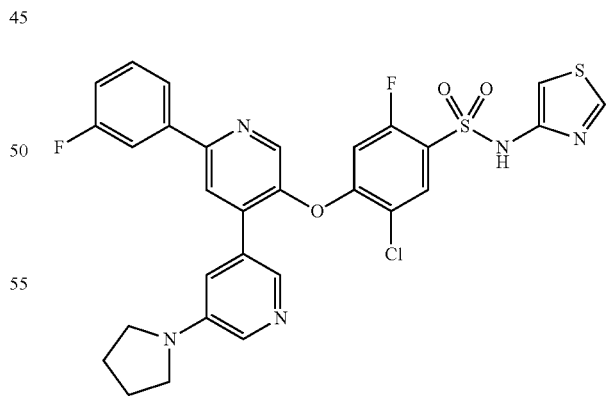

30 mg (0.05 mmol) of 5-chloro-2-fluoro-4-((6-(3-fluorophenyl)-4-iodipyridin-3-yl)oxy)-N-(thiazol-4-yl)benzenesulfonamide was dissolved in 0.9 mL of N,N-dimethylformamide, and 13.2 mg (0.05 mmol) of (5-(pyrrolidin-1-yl)pyridin-3-yl)boronic acid was added thereto, and then 5.3 mg (10 mol %) of Pd(PPh$_3$)$_4$, 14.5 mg (0.15 mmol) of Na$_2$CO$_3$, and 0.1 mL of H$_2$O were added thereto. After reacting with microwave reactor at 120° C. for 10 minutes, the solvent was removed, and the remaining material was diluted with ethyl acetate and the organic layer was separated, and washed with saturated sodium chloride. The organic layer was collected, dried with magnesium sulfate to remove water, and concentrated under reduced pressure, and the residue was purified by column chromatography (developing solvent, hexane:ethyl acetate=1:2) to obtain 5.0 mg (17.5% yield) of the title compound.

$^1$H NMR (CD$_3$OD, 500 MHz) δ 8.71 (1H), 8.70 (1H), 8.56 (1H), 8.08 (1H), 7.87 (4H), 7.51 (1H), 7.19 (1H), 7.12 (1H), 6.97 (1H), 6.73 (1H), 2.00 (4H)

Example 100

Preparation of 5-chloro-2-fluoro-4-((6-(3-fluorophenyl)-4-(1-(pyridin-3-yl)-1H-imidazol-4-yl)pyridin-3-yl)oxy)-N-(thiazol-4-yl)benzenesulfonamide

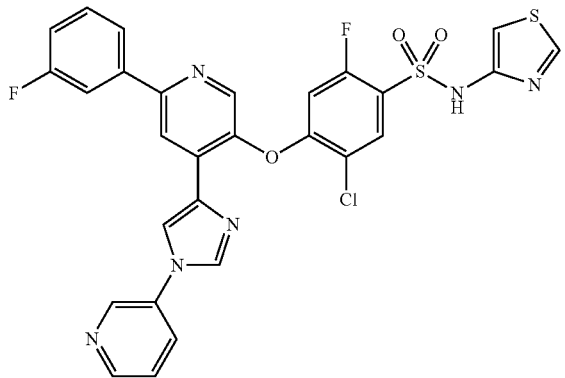 [SMILES: O=S(=O)(Nc1cscn1)c1cc(Cl)c(Oc2cnc(-c3cccc(F)c3)cc2-c2cn(-c3cccnc3)cn2)cc1F]

3.0 mg (10.5% yield) of the title compound was obtained in the same manner as described in Example 99, except that 3-(4-(4,4,5,5,-tetramethyl-1,3,2-dioxaboran-2-yl)-1H-imidazol-1-yl)pyridine was used instead of (5-(pyrrolidin-1-yl)pyridin-3-yl)boronic acid.

$^1$H NMR (CD$_3$OD, 500 MHz) δ 8.30 (1H), 8.11 (1H), 7.78 (3H), 7.67 (3H), 7.56 (3H), 7.45 (1H), 7.11 (1H)

Example 101

Preparation of 5-chloro-2-fluoro-4-((6-(3-fluorophenyl)-2'-morpholino-[4,4'-bipyridin]-3-yl)oxy)-N-(thiazol-4-yl)benzenesulfonamide

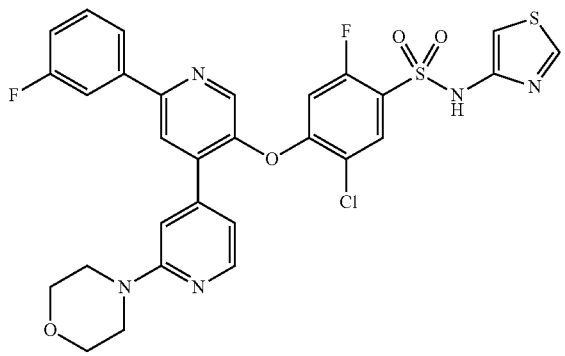 [SMILES: O=S(=O)(Nc1cscn1)c1cc(Cl)c(Oc2cnc(-c3cccc(F)c3)cc2-c2ccnc(N3CCOCC3)c2)cc1F]

4.5 mg (15.4% yield) of the title compound was obtained in the same manner as described in Example 99, except that (2-morpholinopyridin-4-yl)boronic acid was used instead of (5-(pyrrolidin-1-yl)pyridin-3-yl)boronic acid.

$^1$H NMR (CD$_3$OD, 500 MHz) δ 8.71 (1H), 8.56 (1H), 8.11 (1H), 8.06 (1H), 7.92 (1H), 7.87 (2H), 7.53 (1H), 7.20 (1H), 6.94 (2H), 6.86 (1H), 6.72 (1H), 3.75 (4H), 3.46 (4H)

Example 102

Preparation of 5-chloro-2-fluoro-4-((6-(3-fluorophenyl)-2'-(piperidin-1-yl)-[4,4'-bipyridin]-3-yl)oxy)-N-(thiazol-4-yl)benzenesulfonamide

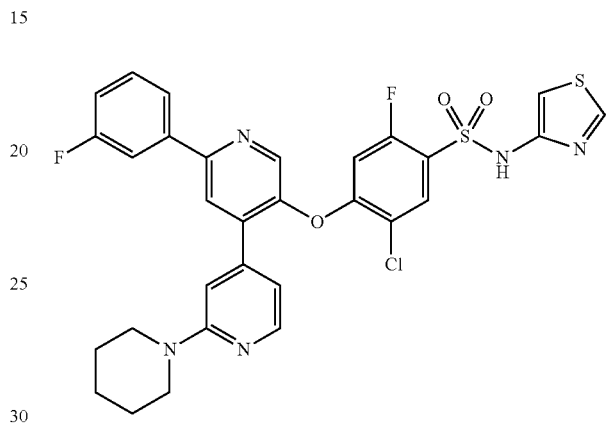

4.8 mg (16.4% yield) of the title compound was obtained in the same manner as described in Example 99, except that (2-(piperidin-1-yl)pyridin-4-yl)boronic acid was used instead of (5-(pyrrolidin-1-yl)pyridin-3-yl)boronic acid.

$^1$H NMR (CD$_3$OD, 500 MHz) δ 8.71 (1H), 8.55 (1H), 8.05 (2H), 7.91 (1H), 7.87 (2H), 7.52 (1H), 7.20 (1H), 6.94 (1H), 6.87 (1H), 6.77 (1H), 6.72 (1H), 3.49 (4H), 1.65 (2H), 1.56 (4H)

Example 103

Preparation of 3-cyano-4-((2'-fluoro-6-(furan-3-yl)-[2,3'-bipyridin]-5-yl)oxy)-N-(thiazol-2-yl)benzenesulfonamide

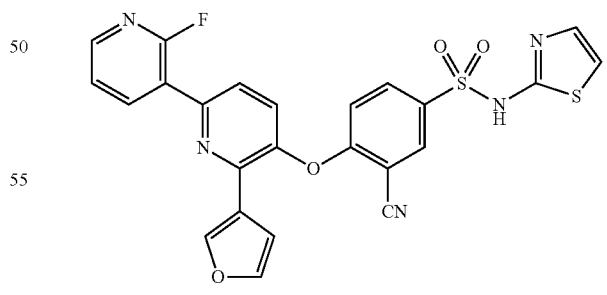

2.5 mg (22.1% yield) of the title compound was obtained in the same manner as described in Example 5, except that 4-((6-chloro-2-(furan-3-yl)pyridin-3-yl)oxy)-3-cyano-N-(thiazol-2-yl)benzenesulfonamide and (2-fluoropyridin-3-yl)boronic acid were used instead of 4-((6-chloro-4-(furan-3-yl)pyridin-3-yl)oxy)-3-cyano-N-(thiazol-2-yl)benzenesulfonamide and (3-fluorophenyl)boronic acid.

$^1$H NMR (DMSO-d$_6$, 500 MHz) δ 6.87 (1H), 7.18 (2H), 7.28 (1H), 7.56 (1H), 7.89 (2H), 7.99 (1H), 7.28 (2H), 8.34 (1H), 8.70 (1H)

Example 104

Preparation of 3-cyano-4-((6'-fluoro-6-(furan-3-yl)-[2,3'-bipyridin]-5-yl)oxy)-N-(thiazol-2-yl)benzenesulfonamide

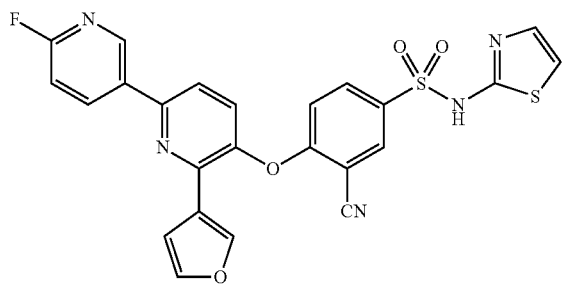 [SMILES: N#Cc1cc(S(=O)(=O)Nc2nccs2)ccc1Oc1ccc(-c2ccc(F)nc2)nc1-c1ccoc1]

2.5 mg (11.0% yield) of the title compound was obtained in the same manner as described in Example 5, except that 4-((6-chloro-2-(furan-3-yl)pyridin-3-yl)oxy)-3-cyano-N-(thiazol-2-yl)benzenesulfonamide and (6-fluoropyridin-3-yl)boronic acid were used instead of 4-((6-chloro-4-(furan-3-yl)pyridin-3-yl)oxy)-3-cyano-N-(thiazol-2-yl)benzenesulfonamide and (3-fluorophenyl)boronic acid.

$^1$H NMR (CD$_3$OD, 500 MHz) δ 6.86 (1H), 7.10 (1H), 7.20 (1H), 7.28 (1H), 7.34 (1H), 7.81 (1H), 7.92 (1H), 7.96 (1H), 8.08 (1H), 8.28 (2H), 8.77 (1H), 9.10 (1H)

Example 105

Preparation of 3-cyano-4-((6-(furan-3-yl)-[2,3'-bipyridin]-5-yl)oxy)-N-(thiazol-2-yl)benzenesulfonamide

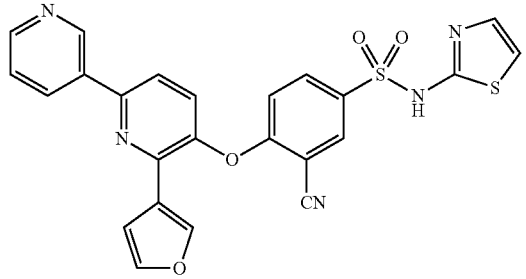 [SMILES: N#Cc1cc(S(=O)(=O)Nc2nccs2)ccc1Oc1ccc(-c2cccnc2)nc1-c1ccoc1]

2.5 mg (11.5% yield) of the title compound was obtained in the same manner as described in Example 5, except that 4-((6-chloro-4-(furan-3-yl)pyridin-3-yl)oxy)-3-cyano-N-(thiazol-2-yl)benzenesulfonamide and (3-fluorophenyl)boronic acid were used instead of 4-((6-chloro-2-(furan-3-yl)pyridin-3-yl)oxy)-3-cyano-N-(thiazol-2-yl)benzenesulfonamide and pyridin-3-ylboronic acid.

$^1$H NMR (CD$_3$OD, 500 MHz) δ 6.73 (1H), 7.04 (1H), 7.11 (1H), 7.21 (1H), 7.59 (2H), 7.71 (1H), 7.95 (1H), 8.05 (1H), 8.19 (1H), 8.30 (1H), 8.61 (2H), 9.31 (1H)

Example 106

Preparation of 3-cyano-4-((2-(furan-3-yl)-6-(pyrimidin-5-yl)pyridin-3-yl)oxy)-N-(thiazol-2-yl)benzenesulfonamide

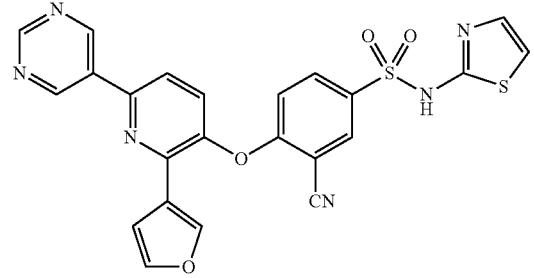 [SMILES: N#Cc1cc(S(=O)(=O)Nc2nccs2)ccc1Oc1ccc(-c2cncnc2)nc1-c1ccoc1]

2.4 mg (11.0% yield) of the title compound was obtained in the same manner as described in Example 5, except that 4-((6-chloro-2-(furan-3-yl)pyridin-3-yl)oxy)-3-cyano-N-(thiazol-2-yl)benzenesulfonamide and (pyrimidin-5-yl)boronic acid were used instead of 4-((6-chloro-4-(furan-3-yl)pyridin-3-yl)oxy)-3-cyano-N-(thiazol-2-yl)benzenesulfonamide and (3-fluorophenyl)boronic acid.

$^1$H NMR (DMSO-d$_6$, 500 MHz) δ 6.74 (1H), 7.08 (1H), 7.12 (1H), 7.22 (1H), 7.60 (1H), 7.73 (1H), 8.00 (1H), 8.06 (1H), 8.22 (1H), 8.31 (1H), 9.22 (1H), 9.52 (2H)

Example 107

Preparation of 3-cyano-4-((2'-fluoro-6-(1-methyl-1H-pyrazol-5-yl)-[2,4'-bipyridin]-5-yl)oxy)-N-(thiazol-2-yl)benzenesulfonamide

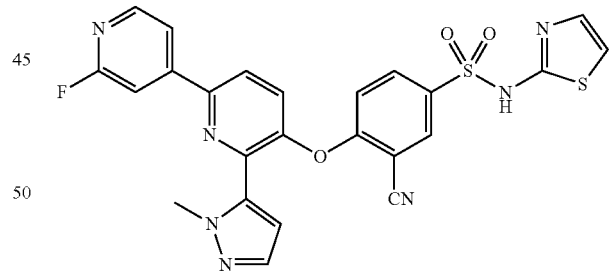

2.0 mg (15.2% yield) of the title compound was obtained in the same manner as described in Example 5, except that 4-((6-chloro-2-(1-methyl-1H-pyrazol-5-yl)pyridin-3-yl)oxy)-3-cyano-N-(thiazol-2-yl)benzenesulfonamide and (2-fluoropyridin-4-yl)boronic acid were used instead of 4-((6-chloro-4-(furan-3-yl)pyridin-3-yl)oxy)-3-cyano-N-(thiazol-2-yl)benzenesulfonamide and (3-fluorophenyl)boronic acid.

$^1$H NMR (DMSO-d$_6$, 500 MHz) δ 4.10 (3H), 6.61 (1H), 6.88 (1H), 7.15 (1H), 7.29 (1H), 7.47 (1H), 7.92 (2H), 8.12 (2H), 8.23 (1H), 8.39 (2H), 12.88 (1H)

Example 108

Preparation of 3-cyano-4-((6-(2-fluorophenyl)-2-(furan-3-yl)pyridin-3-yl)oxy)-N-(thiazol-2-yl)benzenesulfonamide

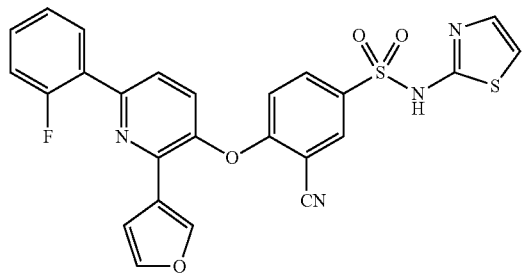 [SMILES: N#Cc1cc(S(=O)(=O)Nc2nccs2)ccc1Oc1ccc(-c2ccccc2F)nc1-c1ccoc1]

3.0 mg (13.2% yield) of the title compound was obtained in the same manner as described in Example 5, except that 4-((6-chloro-2-(furan-3-yl)pyridin-3-yl)oxy)-3-cyano-N-(thiazol-2-yl)benzenesulfonamide and (2-fluorophenyl)boronic acid were used instead of 4-((6-chloro-4-(furan-3-yl)pyridin-3-yl)oxy)-3-cyano-N-(thiazol-2-yl)benzenesulfonamide and (3-fluorophenyl)boronic acid.

$^1$H NMR (DMSO-$d_6$, 500 MHz) δ 6.86 (1H), 7.14 (2H), 7.28 (1H), 7.37 (2H), 7.52 (1H), 7.79 (2H), 7.86 (1H), 7.98 (1H), 8.10 (1H), 8.30 (2H)

Example 109

Preparation of 3-cyano-4-((6-(4-fluorophenyl)-2-(furan-3-yl)pyridin-3-yl)oxy)-N-(thiazol-2-yl)benzenesulfonamide

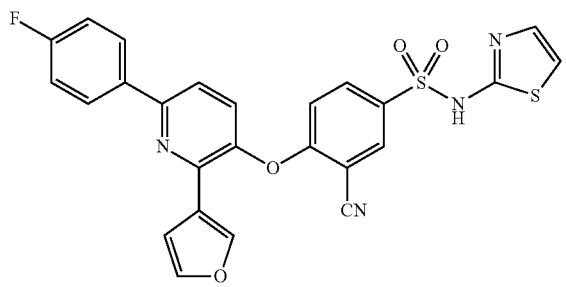 [SMILES: N#Cc1cc(S(=O)(=O)Nc2nccs2)ccc1Oc1ccc(-c2ccc(F)cc2)nc1-c1ccoc1]

4.5 mg (19.7% yield) of the title compound was obtained in the same manner as described in Example 5, except that 4-((6-chloro-2-(furan-3-yl)pyridin-3-yl)oxy)-3-cyano-N-(thiazol-2-yl)benzenesulfonamide and (4-fluorophenyl)boronic acid were used instead of 4-((6-chloro-4-(furan-3-yl)pyridin-3-yl)oxy)-3-cyano-N-(thiazol-2-yl)benzenesulfonamide and (3-fluorophenyl)boronic acid.

$^1$H NMR (DMSO-$d_6$, 500 MHz) δ 6.86 (1H), 7.08 (1H), 7.16 (1H), 7.27 (1H), 7.34 (2H), 7.80 (1H), 7.86 (1H), 7.97 (2H), 8.25 (4H)

Example 110

Preparation of 3-cyano-4-((6-(3-fluorophenyl)-2-(furan-3-yl)pyridin-3-yl)oxy)-N-(thiazol-2-yl)benzenesulfonamide

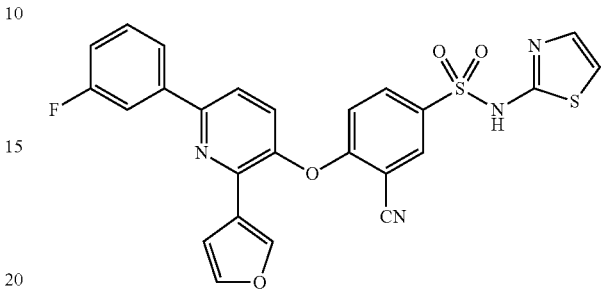

4.3 mg (18.9% yield) of the title compound was obtained in the same manner as described in Example 5, except that 4-((6-chloro-2-(furan-3-yl)pyridin-3-yl)oxy)-3-cyano-N-(thiazol-2-yl)benzenesulfonamide and (3-fluorophenyl)boronic acid were used instead of 4-((6-chloro-4-(furan-3-yl)pyridin-3-yl)oxy)-3-cyano-N-(thiazol-2-yl)benzenesulfonamide and (3-fluorophenyl)boronic acid.

$^1$H NMR (DMSO-$d_6$, 500 MHz) δ 6.86 (1H), 7.10 (1H), 7.19 (1H), 7.28 (2H), 7.56 (1H), 7.80 (1H), 7.87 (1H), 7.96 (1H), 8.04 (3H), 8.27 (2H)

Example 111

Preparation of 3-cyano-4-((6-(furan-3-yl)-[2,4'-bipyridin]-5-yl)oxy)-N-(thiazol-2-yl)benzenesulfonamide

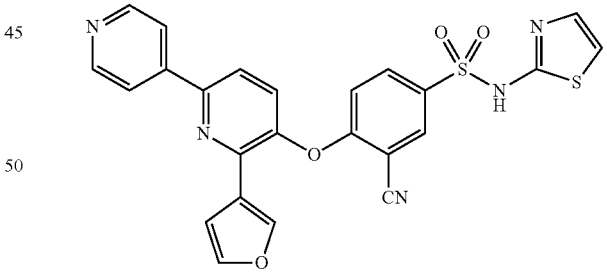

2.5 mg (11.3% yield) of the title compound was obtained in the same manner as described in Example 5, except that 4-((6-chloro-2-(furan-3-yl)pyridin-3-yl)oxy)-3-cyano-N-(thiazol-2-yl)benzenesulfonamide and pyridin-4-ylboronic acid were used instead of 4-((6-chloro-4-(furan-3-yl)pyridin-3-yl)oxy)-3-cyano-N-(thiazol-2-yl)benzenesulfonamide and (3-fluorophenyl)boronic acid.

$^1$H NMR (CD$_3$OD, 500 MHz) δ 6.76 (1H), 7.08 (1H), 7.13 (1H), 7.24 (1H), 7.61 (1H), 7.73 (1H), 8.05 (2H), 8.21 (3H), 8.32 (1H), 8.68 (2H)

Example 112

Preparation of 3-cyano-4-((2'-fluoro-6-(furan-3-yl)-[2,4'-bipyridin]-5-yl)oxy)-N-(thiazol-2-yl)benzenesulfonamide

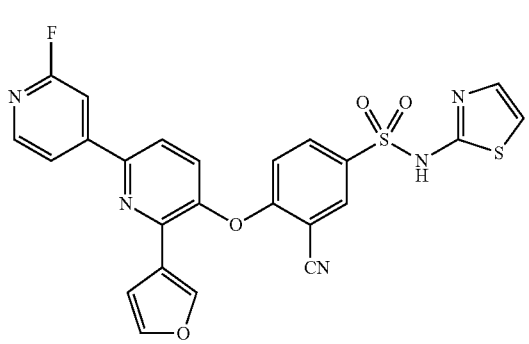 [SMILES: N#Cc1cc(S(=O)(=O)Nc2nccs2)ccc1Oc1ccc(-c2ccnc(F)c2)nc1-c1ccoc1]

2.5 mg (11.0% yield) of the title compound was obtained in the same manner as described in Example 5, except that 4-((6-chloro-2-(furan-3-yl)pyridin-3-yl)oxy)-3-cyano-N-(thiazol-2-yl)benzenesulfonamide and (2-fluoropyridin-4-yl)boronic acid were used instead of 4-((6-chloro-4-(furan-3-yl)pyridin-3-yl)oxy)-3-cyano-N-(thiazol-2-yl)benzenesulfonamide and (3-fluorophenyl)boronic acid.

$^1$H NMR (CD$_3$OD, 500 MHz) δ 6.75 (1H), 7.09 (1H), 7.13 (1H), 7.24 (1H), 7.61 (1H), 7.72 (1H), 7.85 (1H), 7.94 (3H), 8.23 (1H), 8.33 (1H)

Example 113

Preparation of 3-cyano-4-((2-(furan-3-yl)-6-(thiophen-3-yl)pyridin-3-yl)oxy)-N-(thiazol-2-yl)benzenesulfonamide

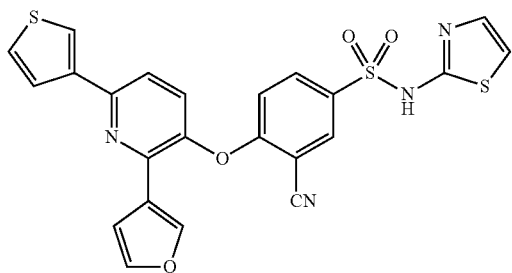 [SMILES: N#Cc1cc(S(=O)(=O)Nc2nccs2)ccc1Oc1ccc(-c2ccsc2)nc1-c1ccoc1]

3.0 mg (13.4% yield) of the title compound was obtained in the same manner as described in Example 5, except that 4-((6-chloro-2-(furan-3-yl)pyridin-3-yl)oxy)-3-cyano-N-(thiazol-2-yl)benzenesulfonamide and thiophen-3-ylboronic acid were used instead of 4-((6-chloro-4-(furan-3-yl)pyridin-3-yl)oxy)-3-cyano-N-(thiazol-2-yl)benzenesulfonamide and (3-fluorophenyl)boronic acid.

$^1$H NMR (CD$_3$OD, 500 MHz) δ 6.75 (1H), 6.95 (1H), 7.14 (1H), 7.52 (1H), 7.56 (1H) 7.61 (1H), 7.76 (1H), 7.80 (1H), 8.01 (1H), 8.11 (2H), 8.30 (1H)

Example 114

Preparation of 3-cyano-4-((2,6-di(furan-3-yl)pyridin-3-yl)oxy)-N-(thiazol-2-yl)benzenesulfonamide

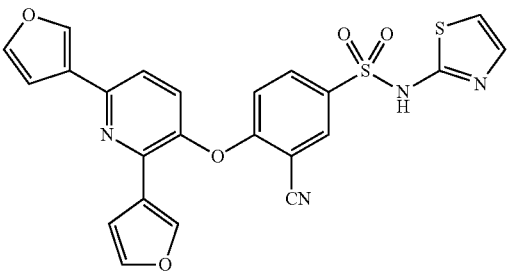 [SMILES: N#Cc1cc(S(=O)(=O)Nc2nccs2)ccc1Oc1ccc(-c2ccoc2)nc1-c1ccoc1]

3.2 mg (14.8% yield) of the title compound was obtained in the same manner as described in Example 5, except that 4-((6-chloro-2-(furan-3-yl)pyridin-3-yl)oxy)-3-cyano-N-(thiazol-2-yl)benzenesulfonamide and furan-3-ylboronic acid were used instead of 4-((6-chloro-4-(furan-3-yl)pyridin-3-yl)oxy)-3-cyano-N-(thiazol-2-yl)benzenesulfonamide and (3-fluorophenyl)boronic acid.

$^1$H NMR (CD$_3$OD, 500 MHz) δ 6.71 (1H), 6.92 (1H), 7.05 (1H), 7.09 (1H), 7.12 (1H), 7.58 (4H), 8.01 (1H), 8.09 (1H), 8.20 (1H), 8.27 (1H)

Example 115

Preparation of 3-cyano-4-((6'-fluoro-6-(1-methyl-1H-pyrazol-5-yl)-[2,3'-bipyridin]-5-yl)oxy)-N-(thiazol-2-yl)benzenesulfonamide

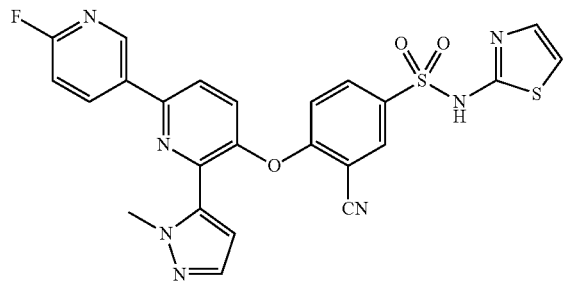

2.4 mg (18.2% yield) of the title compound was obtained in the same manner as described in Example 5, except that 4-((6-chloro-2-(1-methyl-1H-pyrazol-5-yl)pyridin-3-yl)oxy)-3-cyano-N-(thiazol-2-yl)benzenesulfonamide and (6-fluoropyridin-3-yl)boronic acid were used instead of 4-((6-chloro-4-(furan-3-yl)pyridin-3-yl)oxy)-3-cyano-N-(thiazol-2-yl)benzenesulfonamide and (3-fluorophenyl)boronic acid.

$^1$H NMR (CD$_3$OD, 500 MHz) δ 4.11 (3H), 6.69 (1H), 6.76 (1H), 7.02 (1H), 7.13 (1H), 7.23 (1H), 7.44 (1H), 7.89 (1H), 8.00 (1H), 8.11 (1H), 8.20 (1H), 8.68 (1H), 8.98 (1H)

Example 116

Preparation of 3-cyano-4-((2'-fluoro-6-(1-methyl-1H-pyrazol-5-yl)-[2,3'-bipyridin]-5-yl)oxy)-N-(thiazol-2-yl)benzenesulfonamide

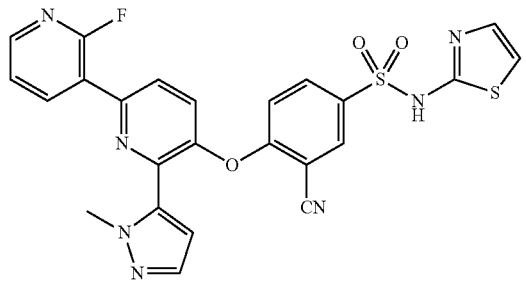 [SMILES: Cn1nccc1-c1nc(-c2cccnc2F)ccc1Oc1ccc(S(=O)(=O)Nc2nccs2)cc1C#N]

1.9 mg (13.7% yield) of the title compound was obtained in the same manner as described in Example 5, except that 4-((6-chloro-2-(1-methyl-1H-pyrazol-5-yl)pyridin-3-yl)oxy)-3-cyano-N-(thiazol-2-yl)benzenesulfonamide and (2-fluoropyridin-3-yl)boronic acid were used instead of 4-((6-chloro-4-(furan-3-yl)pyridin-3-yl)oxy)-3-cyano-N-(thiazol-2-yl)benzenesulfonamide and (3-fluorophenyl)boronic acid.

$^1$H NMR (CD$_3$OD, 500 MHz) δ 4.10 (3H), 6.71 (1H), 6.76 (1H), 7.05 (1H), 7.13 (1H), 7.45 (1H), 7.51 (1H), 7.90 (1H), 8.02 (1H), 8.08 (1H), 8.22 (1H), 8.32 (1H), 8.65 (1H)

Example 117

Preparation of 3-cyano-4-((6-(3-fluorophenyl)-2-(1-methyl-1H-pyrazol-5-yl)pyridin-3-yl)oxy)-N-(thiazol-2-yl)benzenesulfonamide

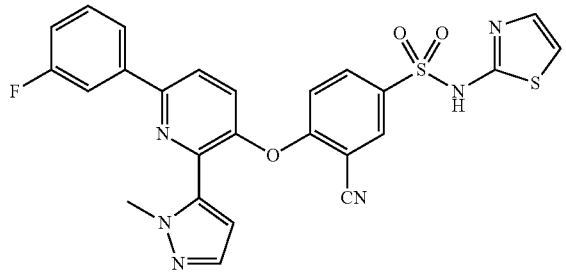 [SMILES: Cn1nccc1-c1nc(-c2cccc(F)c2)ccc1Oc1ccc(S(=O)(=O)Nc2nccs2)cc1C#N]

1.5 mg (17.6% yield) of the title compound was obtained in the same manner as described in Example 5, except that 4-((6-chloro-2-(1-methyl-1H-pyrazol-5-yl)pyridin-3-yl)oxy)-3-cyano-N-(thiazol-2-yl)benzenesulfonamide and (3-fluorophenyl)boronic acid were used instead of 4-((6-chloro-4-(furan-3-yl)pyridin-3-yl)oxy)-3-cyano-N-(thiazol-2-yl)benzenesulfonamide and (3-fluorophenyl)boronic acid.

$^1$H NMR (CD$_3$OD, 500 MHz) δ 4.12 (3H), 6.68 (1H), 6.76 (1H), 6.99 (1H), 7.13 (1H), 7.20 (1H), 7.44 (1H), 7.53 (1H), 7.89 (2H), 7.96 (1H), 7.99 (1H), 8.08 (1H), 8.20 (1H)

Example 118

Preparation of 3-cyano-4-((6-(2-fluorophenyl)-2-(1-methyl-1H-pyrazol-5-yl)pyridin-3-yl)oxy)-N-(thiazol-2-yl)benzenesulfonamide

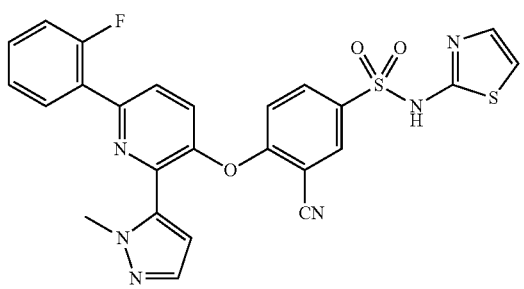 [SMILES: Cn1nccc1-c1nc(-c2ccccc2F)ccc1Oc1ccc(S(=O)(=O)Nc2nccs2)cc1C#N]

1.3 mg (15.3% yield) of the title compound was obtained in the same manner as described in Example 5, except that 4-((6-chloro-2-(1-methyl-1H-pyrazol-5-yl)pyridin-3-yl)oxy)-3-cyano-N-(thiazol-2-yl)benzenesulfonamide and (2-fluorophenyl)boronic acid were used instead of 4-((6-chloro-4-(furan-3-yl)pyridin-3-yl)oxy)-3-cyano-N-(thiazol-2-yl)benzenesulfonamide and (3-fluorophenyl)boronic acid.

$^1$H NMR (CD$_3$OD, 500 MHz) δ 4.09 (3H), 6.68 (1H), 6.75 (1H), 7.01 (1H), 7.13 (1H), 7.28 (1H), 7.35 (1H), 7.43 (1H), 7.85 (1H), 8.00 (3H), 8.20 (1H)

Example 119

Preparation of 3-cyano-4-((2-(1-methyl-1H-pyrazol-5-yl)-6-(thiophen-3-yl)pyridin-3-yl)oxy)-N-(thiazol-2-yl)benzenesulfonamide

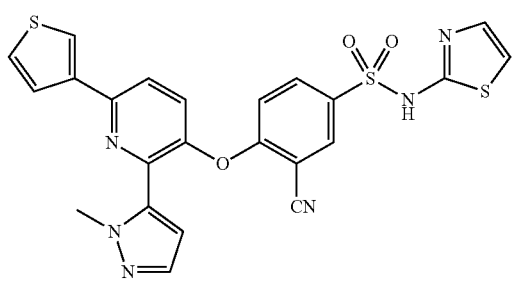 [SMILES: Cn1nccc1-c1nc(-c2ccsc2)ccc1Oc1ccc(S(=O)(=O)Nc2nccs2)cc1C#N]

4.5 mg (20.4% yield) of the title compound was obtained in the same manner as described in Example 5, except that 4-((6-chloro-2-(1-methyl-1H-pyrazol-5-yl)pyridin-3-yl)oxy)-3-cyano-N-(thiazol-2-yl)benzenesulfonamide and (thiophen-3-yl)boronic acid were used instead of 4-((6-chloro-4-(furan-3-yl)pyridin-3-yl)oxy)-3-cyano-N-(thiazol-2-yl)benzenesulfonamide and (3-fluorophenyl)boronic acid.

$^1$H NMR (DMSO-d$_6$, 500 MHz) δ 4.09 (3H), 6.53 (1H), 6.80 (1H), 7.02 (1H), 7.22 (1H), 7.43 (1H), 7.70 (1H), 7.82 (1H), 7.89 (1H), 7.97 (1H), 8.05 (1H), 8.18 (1H), 8.31 (1H)

Example 120

Preparation of 3-cyano-4-((6-(1-methyl-1H-pyrazol-4-yl)-2-(1-methyl-1H-pyrazol-5-yl)pyridin-3-yl)oxy)-N-(thiazol-2-yl)benzenesulfonamide

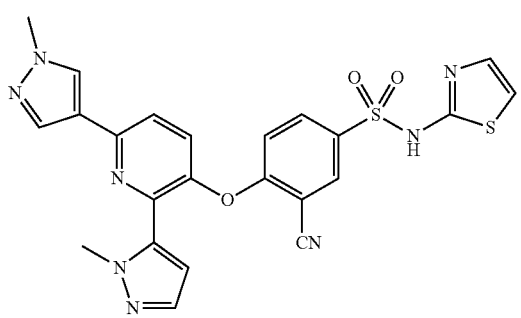 [SMILES: Cn1cc(-c2ccc(Oc3ccc(S(=O)(=O)Nc4nccs4)cc3C#N)c(-c3ccnn3C)n2)cn1]

2.5 mg (11.4% yield) of the title compound was obtained in the same manner as described in Example 5, except that 4-((6-chloro-2-(1-methyl-1H-pyrazol-5-yl)pyridin-3-yl)oxy)-3-cyano-N-(thiazol-2-yl)benzenesulfonamide and (1-methyl-1H-pyrazol-4-yl)boronic acid were used instead of 4-((6-chloro-4-(furan-3-yl)pyridin-3-yl)oxy)-3-cyano-N-(thiazol-2-yl)benzenesulfonamide and (3-fluorophenyl)boronic acid.

$^1$H NMR (CD$_3$OD, 500 MHz) δ 3.97 (3H), 4.09 (3H), 6.61 (1H), 6.73 (1H), 6.92 (1H), 7.12 (1H), 7.76 (1H), 7.97 (1H), 8.07 (1H), 8.17 (1H), 8.25 (1H)

Example 121

Preparation of 3-cyano-4-((6-(isoxazol-4-yl)-2-(1-methyl-1H-pyrazol-5-yl)pyridin-3-yl)oxy)-N-(thiazol-2-yl)benzenesulfonamide

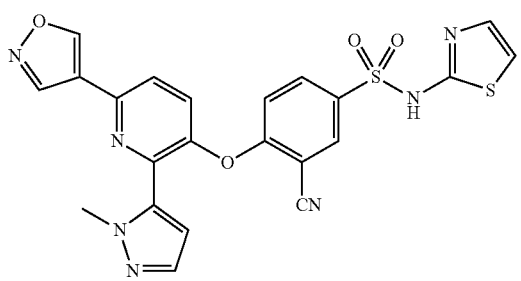 [SMILES: Cn1nccc1-c1nc(-c2cnoc2)ccc1Oc1ccc(S(=O)(=O)Nc2nccs2)cc1C#N]

3.0 mg (14.0% yield) of the title compound was obtained in the same manner as described in Example 5, except that 4-((6-chloro-2-(1-methyl-1H-pyrazol-5-yl)pyridin-3-yl)oxy)-3-cyano-N-(thiazol-2-yl)benzenesulfonamide and (isoxazol-4-yl)boronic acid were used instead of 4-((6-chloro-4-(furan-3-yl)pyridin-3-yl)oxy)-3-cyano-N-(thiazol-2-yl)benzenesulfonamide and (3-fluorophenyl)boronic acid.

$^1$H NMR (CD$_3$OD, 500 MHz) δ 3.90 (3H), 6.48 (1H), 6.75 (1H), 6.89 (1H), 7.12 (1H), 7.40 (1H), 7.64 (1H), 7.79 (1H), 7.96 (1H), 8.13 (1H), 8.84 (1H), 9.08 (1H)

Example 122

Preparation of 3-cyano-4-((6-(3-fluorophenyl)-2-(1-methyl-1H-pyrazol-4-yl)pyridin-3-yl)oxy)-N-(thiazol-2-yl)benzenesulfonamide

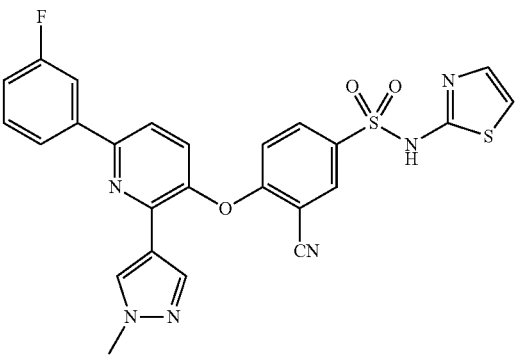 [SMILES: Cn1cc(-c2nc(-c3cccc(F)c3)ccc2Oc2ccc(S(=O)(=O)Nc3nccs3)cc2C#N)cn1]

10 mg (0.02 mmol) of 4-((6-chloro-2-(1-methyl-1H-pyrazol-4-yl)pyridin-3-yl)oxy)-3-cyano-N-(thiazol-2-yl)benzenesulfonamide was dissolved in 3 mL of N,N-dimethylformamide, and 4.4 mg (0.03 mmol) of (3-fluorophenyl)boronic acid was added thereto, and then 2.4 mg (10 mol %) of Pd(PPh$_3$)$_4$, 6.7 mg (0.63 mmol) of Na$_2$CO$_3$, and 1 mL of H$_2$O were added thereto. After reacting with microwave reactor at 120° C. for 10 minutes, the solvent was removed, and the remaining material was diluted with ethyl acetate and the organic layer was separated, and washed with saturated sodium chloride. The organic layer was collected, dried with magnesium sulfate to remove water, and concentrated under reduced pressure, and the residue was purified by column chromatography (developing solvent, hexane:ethyl acetate=3:1) to obtain 5 mg (45% yield) of the title compound.

$^1$H NMR (CD$_3$OD, 500 MHz) δ 8.30 (s, 1H), 8.27 (s, 1H), 8.10 (s, 1H), 8.02 (d, 1H), 7.96 (m, 1H), 7.84 (d, 1H), 7.66 (d, 1H), 7.52 (m, 1H), 7.18 (m, 1H), 7.12 (d, 1H), 6.99 (d, 1H), 6.76 (d, 1H), 3.92 (s, 3H)

Example 123

Preparation of 3-cyano-4-((2'-fluoro-6-(1-methyl-1H-pyrazol-4-yl)-[2,3'-bipyridin]-5-yl)oxy)-N-(thiazol-2-yl)benzenesulfonamide

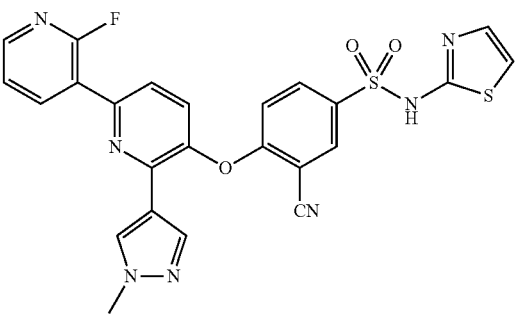 [SMILES: Cn1cc(-c2nc(-c3cccnc3F)ccc2Oc2ccc(S(=O)(=O)Nc3nccs3)cc2C#N)cn1]

5 mg (45% yield) of the title compound was obtained in the same manner as described in Example 122, except that (2-fluorophenyl-4-yl)boronic acid was used instead of (3-fluorophenyl)boronic acid.

¹H NMR (CD₃OD/CDCl₃, 500 MHz) δ 8.79 (m, 1H), 8.33 (s, 1H), 8.30 (m, 2H), 8.15 (s, 1H), 8.08 (d, 1H), 7.88 (d, 1H), 7.72 (d, 1H), 7.55 (m, 1H), 7.15 (d, 1H), 7.08 (d, 1H), 4.65 (s, 2H), 3.92 (s, 3H)

Example 124

Preparation of 3-cyano-4-((6'-fluoro-6-(1-methyl-1H-pyrazol-4-yl)-[2,3'-bipyridin]-5-yl)oxy)-N-(thiazol-2-yl)benzenesulfonamide

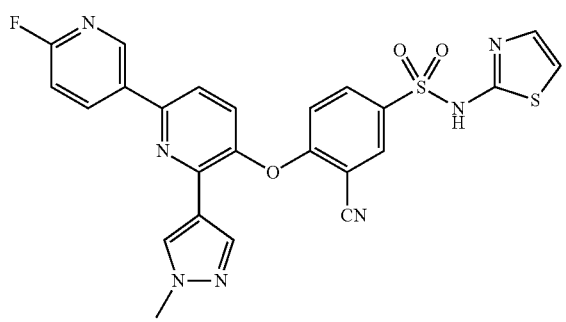 [SMILES: Cn1cc(-c2nc(-c3ccc(F)nc3)ccc2Oc2ccc(S(=O)(=O)Nc3nccs3)cc2C#N)cn1]

5 mg (45% yield) of the title compound was obtained in the same manner as described in Example 122, except that (6-fluoropyridin-3-yl)boronic acid was used instead of (3-fluorophenyl)boronic acid.

¹H NMR (CD₃OD/CDCl₃, 500 MHz) δ 8.99 (s, 1H), 8.76 (m, 1H), 8.30 (m, 2H), 8.14 (s, 1H), 8.07 (d, 1H), 7.89 (d, 1H), 7.68 (m, 5H), 7.59 (m, 3H), 7.25 (m, 1H), 7.16 (d, 1H), 7.05 (d, 1H), 6.78 (d, 1H), 3.94 (s, 3H)

Example 125

Preparation of 3-cyano-4-((2'-fluoro-6-(1-methyl-1H-pyrazol-4-yl)-[2,4'-bipyridin]-5-yl)oxy)-N-(thiazol-2-yl)benzenesulfonamide

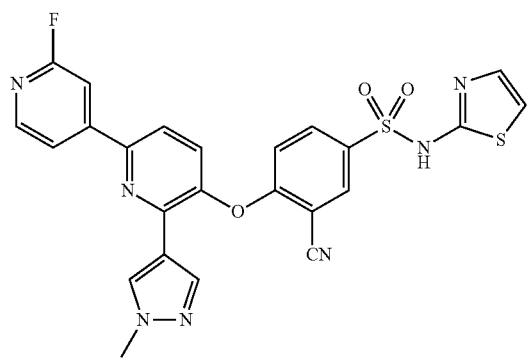 [SMILES: Cn1cc(-c2nc(-c3ccnc(F)c3)ccc2Oc2ccc(S(=O)(=O)Nc3nccs3)cc2C#N)cn1]

5 mg (45% yield) of the title compound was obtained in the same manner as described in Example 122, except that (2-fluoropyridin-4-yl)boronic acid was used instead of (3-fluorophenyl)boronic acid.

¹H NMR (CD₃OD/CDCl₃, 500 MHz) δ 8.36 (m, 1H), 8.18 (s, 1H), 8.10 (m, 2H), 8.00 (d, 1H), 7.88 (s, 1H), 7.72 (d, 1H), 7.62 (m, 2H), 7.15 (m, 1H), 7.10 (m, 1H), 6.78 (d, 1H), 3.96 (s, 3H)

Example 126

Preparation of 3-cyano-4-((2',6'-difluoro-6-(1-methyl-1H-pyrazol-4-yl)-[2,3'-bipyridin]-5-yl)oxy)-N-(thiazol-2-yl)benzenesulfonamide

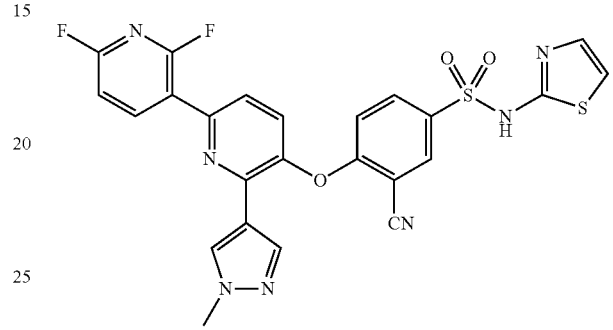

5 mg (45% yield) of the title compound was obtained in the same manner as described in Example 122, except that (2,6-difluoropyridin-3-yl)boronic acid was used instead of (3-fluorophenyl)boronic acid.

¹H NMR (CD₃OD/CDCl₃, 500 MHz) δ 8.86 (m, 1H), 8.31 (s, 1H), 8.11 (s, 1H), 8.05 (m, 1H), 7.82 (m, 1H), 7.69 (m, 1H), 7.62 (m, 2H), 7.19 (m, 1H), 7.13 (m, 1H), 7.06 (d, 1H), 6.76 (d, 1H), 3.92 (s, 3H)

Example 127

Preparation of 3-cyano-4-((2',6'-difluoro-6-(furan-3-yl)-[2,3'-bipyridin]-5-yl)oxy)-N-(thiazol-2-yl)benzenesulfonamide

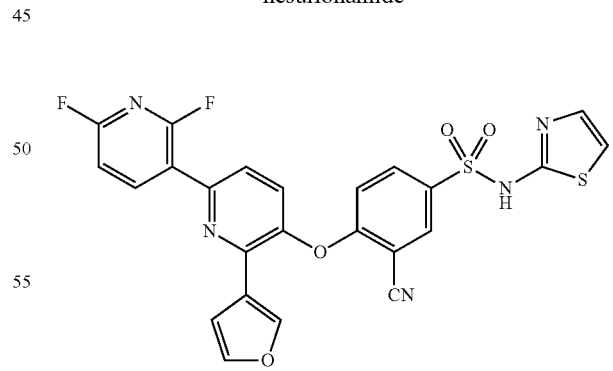

17.4 mg (29.7% yield) of the title compound was obtained in the same manner as described in Example 5, except that 4-((6-chloro-2-(furan-3-yl)pyridin-3-yl)oxy)-3-cyano-N-(thiazol-2-yl)benzenesulfonamide and (2,6-difluoropyridin-3-yl)boronic acid were used instead of 4-((6-chloro-4-(furan-3-yl)pyridin-3-yl)oxy)-3-cyano-N-(thiazol-2-yl)benzenesulfonamide and (3-fluorophenyl)boronic acid.

¹H NMR (CD₃OD, 500 MHz) δ 6.75 (1H), 6.76 (1H), 7.13 (1H), 7.18 (2H), 7.58 (1H), 7.71 (1H), 7.86 (1H), 7.05 (1H), 8.18 (1H), 8.30 (1H), 8.87 (1H)

Example 128

Preparation of 3-cyano-4-((2',6'-difluoro-6-(1-methyl-1H-pyrazol-5-yl)-[2,3'-bipyridin]-5-yl)oxy)-N-(thiazol-2-yl)benzenesulfonamide

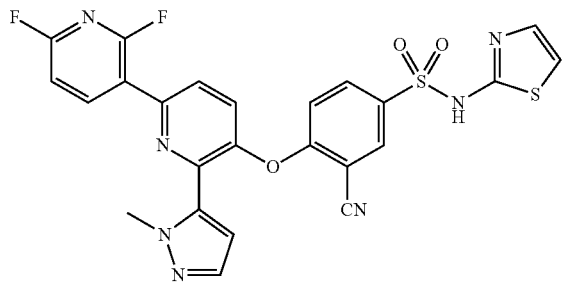 [SMILES: Cn1nccc1-c1nc(-c2ccc(F)nc2F)ccc1Oc1ccc(S(=O)(=O)Nc2nccs2)cc1C#N]

12.0 mg (34.3% yield) of the title compound was obtained in the same manner as described in Example 5, except that 4-((6-chloro-2-(1-methyl-1H-pyrazol-5-yl)pyridin-3-yl)oxy)-3-cyano-N-(thiazol-2-yl)benzenesulfonamide and (2,6-difluoropyridin-3-yl)boronic acid were used instead of 4-((6-chloro-4-(furan-3-yl)pyridin-3-yl)oxy)-3-cyano-N-(thiazol-2-yl)benzenesulfonamide and (3-fluorophenyl)boronic acid.

¹H NMR (CD₃OD, 500 MHz) δ 4.09 (3H), 6.70 (1H), 6.76 (1H), 7.04 (1H), 7.13 (1H), 7.18 (1H), 7.44 (1H), 7.89 (1H), 8.01 (2H), 8.21 (1H), 8.75 (1H)

Example 129

Preparation of 5-chloro-4-((2',6'-difluoro-6-(furan-3-yl)-[2,3'-bipyridin]-5-yl)oxy)-2-fluoro-N-(thiazol-4-yl)benzenesulfonamide

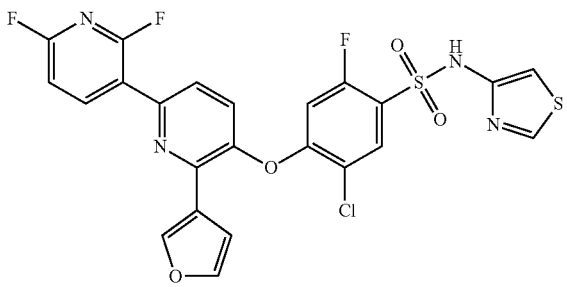 [SMILES: O=S(=O)(Nc1cscn1)c1cc(Cl)c(Oc2ccc(-c3ccc(F)nc3F)nc2-c2ccoc2)cc1F]

4.4 mg (22.8% yield) of the title compound was obtained in the same manner as described in Example 5, except that tert-butyl((5-chloro-4-((6-chloro-2-(furan-3-yl)pyridin-3-yl)oxy)-2-fluorophenyl)sulfonyl)(thiazol-4-yl)carbamate and (2,6-difluoropyridin-3-yl)boronic acid were used instead of 4-((6-chloro-4-(furan-3-yl)pyridin-3-yl)oxy)-3-cyano-N-(thiazol-2-yl)benzenesulfonamide and (3-fluorophenyl)boronic acid.

¹H NMR (CD₃OD, 500 MHz) δ 6.92 (1H), 7.08 (1H), 7.17 (2H), 7.57 (2H), 7.82 (1H), 8.05 (1H), 8.18 (1H), 8.74 (1H), 8.86 (1H)

Example 130

Preparation of 5-chloro-2-fluoro-4-((6'-fluoro-6-(furan-3-yl)-[2,3'-bipyridin]-5-yl)oxy)-N-(thiazol-4-yl)benzenesulfonamide

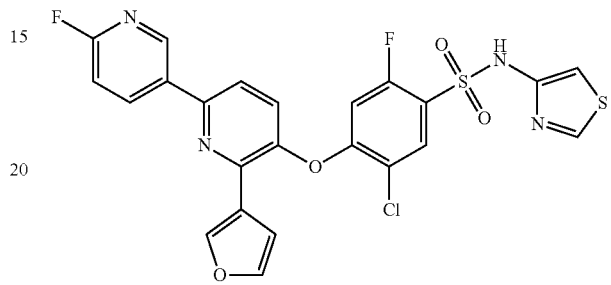

4.5 mg (24.2% yield) of the title compound was obtained in the same manner as described in Example 5, except that tert-butyl((5-chloro-4-((6-chloro-2-(furan-3-yl)pyridin-3-yl)oxy)-2-fluorophenyl)sulfonyl)(thiazol-4-yl)carbamate and (6-fluoropyridin-3-yl)boronic acid were used instead of 4-((6-chloro-4-(furan-3-yl)pyridin-3-yl)oxy)-3-cyano-N-(thiazol-2-yl)benzenesulfonamide and (3-fluorophenyl)boronic acid.

¹H NMR (CD₃OD, 500 MHz) δ 6.88 (1H), 7.78 (1H), 7.21 (2H), 7.58 (2H), 7.86 (1H), 7.05 (1H), 8.17 (1H), 8.71 (2H), 8.94 (1H)

Example 131

Preparation of 5-chloro-2-fluoro-4-((6-(4-fluorophenyl)-2-(furan-3-yl)pyridin-3-yl)oxy)-N-(thiazol-4-yl)benzenesulfonamide

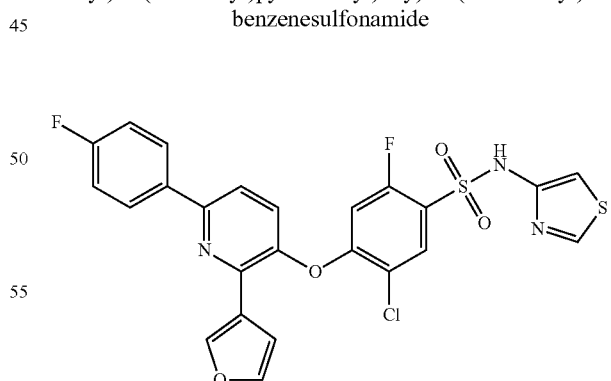

5.7 mg (30.6% yield) of the title compound was obtained in the same manner as described in Example 5, except that tert-butyl((5-chloro-4-((6-chloro-2-(furan-3-yl)pyridin-3-yl)oxy)-2-fluorophenyl)sulfonyl)(thiazol-4-yl)carbamate and (4-fluorophenyl)boronic acid were used instead of 4-((6-chloro-4-(furan-3-yl)pyridin-3-yl)oxy)-3-cyano-N-(thiazol-2-yl)benzenesulfonamide and (3-fluorophenyl)boronic acid.

¹H NMR (CD₃OD, 500 MHz) δ 6.79 (1H), 7.06 (1H), 7.21 (3H), 7.55 (2H), 7.80 (1H), 8.03 (1H), 8.14 (3H), 8.75 (1H)

Example 132

Preparation of 5-chloro-2-fluoro-4-((2'-fluoro-6-(furan-3-yl)-[2,4'-bipyridin]-5-yl)oxy)-N-(thiazol-4-yl)benzenesulfonamide

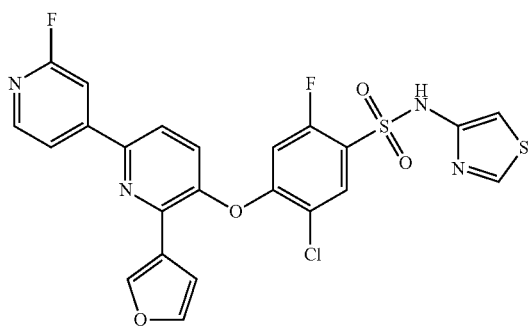

4.1 mg (22.0% yield) of the title compound was obtained in the same manner as described in Example 5, except that tert-butyl((5-chloro-4-((6-chloro-2-(furan-3-yl)pyridin-3-yl)oxy)-2-fluorophenyl)sulfonyl)(thiazol-4-yl)carbamate and (2-fluoropyridin-4-yl)boronic acid were used instead of 4-((6-chloro-4-(furan-3-yl)pyridin-3-yl)oxy)-3-cyano-N-(thiazol-2-yl)benzenesulfonamide and (3-fluorophenyl)boronic acid.

¹H NMR (CD₃OD, 500 MHz) δ 6.99 (1H), 7.09 (1H), 7.25 (1H), 7.55 (1H), 7.61 (1H), 7.83 (1H), 7.98 (1H), 8.07 (2H), 8.23 (1H), 8.32 (1H), 8.74 (1H)

Example 133

Preparation of 5-chloro-2-fluoro-4-((6-(2-fluorophenyl)-2-(furan-3-yl)pyridin-3-yl)oxy)-N-(thiazol-4-yl)benzenesulfonamide

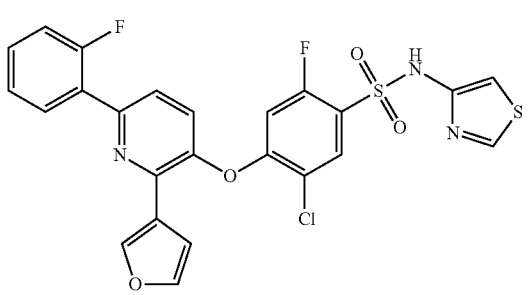

4.0 mg (21.5% yield) of the title compound was obtained in the same manner as described in Example 5, except that tert-butyl((5-chloro-4-((6-chloro-2-(furan-3-yl)pyridin-3-yl)oxy)-2-fluorophenyl)sulfonyl)(thiazol-4-yl)carbamate and (2-fluorophenyl)boronic acid were used instead of 4-((6-chloro-4-(furan-3-yl)pyridin-3-yl)oxy)-3-cyano-N-(thiazol-2-yl)benzenesulfonamide and (3-fluorophenyl)boronic acid.

¹H NMR (CD₃OD, 500 MHz) δ 6.86 (1H), 7.06 (1H), 7.16 (1H), 7.24 (1H), 7.34 (1H), 7.46 (1H), 7.55 (2H), 7.79 (1H), 8.04 (1H), 8.12 (2H), 8.74 (1H)

Example 134

Preparation of 5-chloro-4-((2',6'-difluoro-6-(1-methyl-1H-pyrazol-5-yl)-[2,3'-bipyridin]-5-yl)oxy)-2-fluoro-N-(thiazol-4-yl)benzenesulfonamide

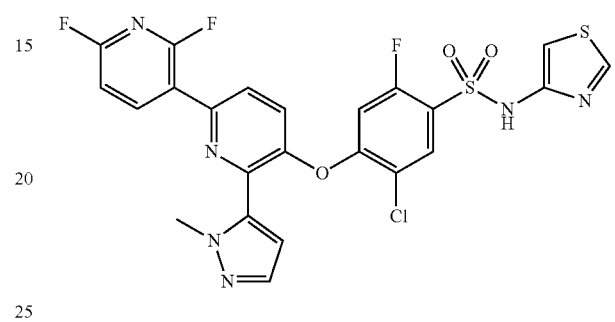

6.0 mg (41.4% yield) of the title compound was obtained in the same manner as described in Example 5, except that tert-butyl((5-chloro-4-((6-chloro-2-(1-methyl-1H-pyrazol-5-yl)pyridin-3-yl)oxy)-2-fluorophenyl)sulfonyl)(thiazol-4-yl)carbamate and (2,6-difluoropyridin-3-yl)boronic acid were used instead of 4-((6-chloro-4-(furan-3-yl)pyridin-3-yl)oxy)-3-cyano-N-(thiazol-2-yl)benzenesulfonamide and (3-fluorophenyl)boronic acid.

¹H NMR (CD₃OD, 500 MHz) δ 4.11 (3H), 6.72 (1H), 6.94 (1H), 7.05 (1H), 7.17 (1H), 7.45 (1H), 7.74 (1H), 7.98 (2H), 8.74 (2H)

Example 135

Preparation of 5-chloro-2-fluoro-4-((6-(4-fluorophenyl)-2-(1-methyl-1H-pyrazol-5-yl)pyridin-3-yl)oxy)-N-(thiazol-4-yl)benzenesulfonamide

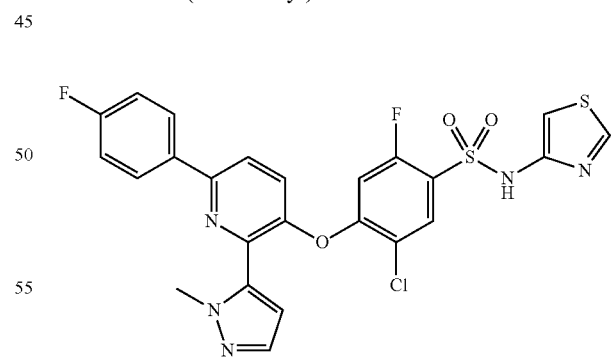

6.0 mg (42.8% yield) of the title compound was obtained in the same manner as described in Example 5, except that tert-butyl((5-chloro-4-((6-chloro-2-(1-methyl-1H-pyrazol-5-yl)pyridin-3-yl)oxy)-2-fluorophenyl)sulfonyl)(thiazol-4-yl)carbamate and (4-fluorophenyl)boronic acid were used instead of 4-((6-chloro-4-(furan-3-yl)pyridin-3-yl)oxy)-3-cyano-N-(thiazol-2-yl)benzenesulfonamide and (3-fluorophenyl)boronic acid.

¹H NMR (CD₃OD, 500 MHz) δ 4.14 (3H), 6.78 (1H), 6.82 (1H), 7.03 (1H), 7.23 (2H), 7.43 (1H), 7.69 (1H), 7.96 (2H), 8.14 (2H), 8.73 (1H)

Example 136

Preparation of 5-chloro-2-fluoro-4-((6-(2-fluorophenyl)-2-(1-methyl-1H-pyrazol-5-yl)pyridin-3-yl)oxy)-N-(thiazol-4-yl)benzenesulfonamide

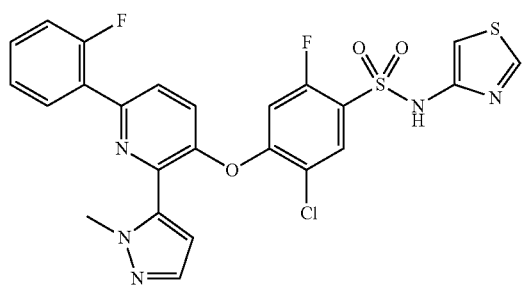 [SMILES: Cn1nccc1-c1nc(-c2ccccc2F)ccc1Oc1cc(F)c(S(=O)(=O)Nc2cscn2)cc1Cl]

6.0 mg (42.8% yield) of the title compound was obtained in the same manner as described in Example 5, except that tert-butyl((5-chloro-4-((6-chloro-2-(1-methyl-1H-pyrazol-5-yl)pyridin-3-yl)oxy)-2-fluorophenyl)sulfonyl)(thiazol-4-yl)carbamate and (2-fluorophenyl)boronic acid were used instead of 4-((6-chloro-4-(furan-3-yl)pyridin-3-yl)oxy)-3-cyano-N-(thiazol-2-yl)benzenesulfonamide and (3-fluorophenyl)boronic acid.

¹H NMR (CD₃OD, 500 MHz) δ 4.16 (3H), 6.77 (1H), 6.95 (1H), 7.28 (1H), 7.35 (1H), 7.48 (2H), 7.72 (1H), 7.84 (1H), 8.03 (2H), 8.19 (1H), 8.96 (1H)

Example 137

Preparation of 5-chloro-2-fluoro-4-((6'-fluoro-6-(1-methyl-1H-pyrazol-5-yl)-[2,3'-bipyridin]-5-yl)oxy)-N-(thiazol-4-yl)benzenesulfonamide

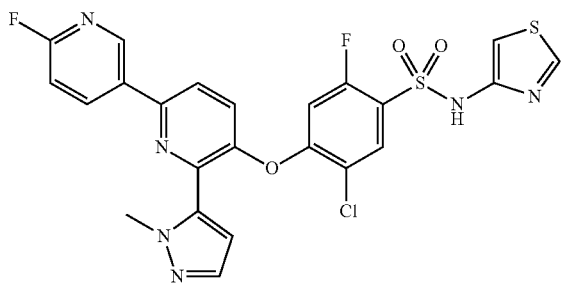 [SMILES: Cn1nccc1-c1nc(-c2ccc(F)nc2)ccc1Oc1cc(F)c(S(=O)(=O)Nc2cscn2)cc1Cl]

6.0 mg (42.8% yield) of the title compound was obtained in the same manner as described in Example 5, except that tert-butyl((5-chloro-4-((6-chloro-2-(1-methyl-1H-pyrazol-5-yl)pyridin-3-yl)oxy)-2-fluorophenyl)sulfonyl)(thiazol-4-yl)carbamate and (6-fluoropyridin-3-yl)boronic acid were used instead of 4-((6-chloro-4-(furan-3-yl)pyridin-3-yl)oxy)-3-cyano-N-(thiazol-2-yl)benzenesulfonamide and (3-fluorophenyl)boronic acid.

¹H NMR (CD₃OD, 500 MHz) δ 4.14 (3H), 6.72 (1H), 6.90 (1H), 7.03 (1H), 7.22 (1H), 7.45 (1H), 7.96 (1H), 8.06 (1H), 8.66 (1H), 8.73 (1H), 8.95 (1H)

Example 138

Preparation of 4-((4-chloro-2-(1-methyl-1H-pyrazol-5-yl)phenyl)(hydroxy)methyl)-N-(thiazol-2-yl)benzenesulfonamide

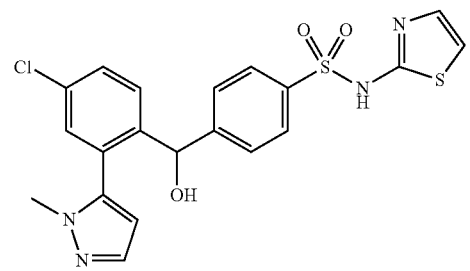 [SMILES: Cn1nccc1-c1cc(Cl)ccc1C(O)c1ccc(S(=O)(=O)Nc2nccs2)cc1]

192 mg (0.46 mmol) of tert-butyl(4-bromophenyl)sulfonyl(thiazol-2-yl)carbamate was dissolved in 1.5 mL of tetrahydrofuran under nitrogen gas, and cooled to −78° C. After adding 0.4 mL (0.64 mmol) of n-butyllithium (1.6M in tetrahydrofuran) slowly, the mixture was stirred for 30 minutes as maintaining −78° C. 50.0 mg (0.23 mmol) of 4-chloro-2-(1-methyl-1H-pyrazol-5-yl)benzaldehyde was dissolved in 0.5 mL of tetrahydrofuran, and added to the above reacting solution. As warming from −78° C. to room temperature, the reacting solution was stirred for 24 hours. Ethyl acetate and water/1 N-hydrochloride were added to the reacting solution, and it was stirred. After separating layers, the organic layer only was collected and concentrated under reduced pressure. The obtained residue was separated by column chromatography (developing solvent, hexane:ethyl acetate=1:2) to obtain 10.0 mg (9.6% yield) of the title compound.

¹H NMR (CD₃OD, 500 MHz) δ 7.80 (1H), 7.73 (2H), 7.55 (1H), 7.50 (1H), 7.23 (1H), 7.07 (3H), 6.70 (1H), 6.26 (1H), 5.72 (1H)

Example 139

Preparation of 4-((4-chloro-2-(1H-pyrazol-4-yl)phenyl)(hydroxy)methyl)-3-fluoro-N-(thiazol-2-yl)benzenesulfonamide

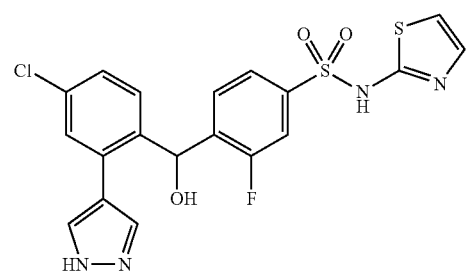 [SMILES: O=S(=O)(Nc1nccs1)c1ccc(C(O)c2ccc(Cl)cc2-c2cn[nH]c2)c(F)c1]

5.77 mg (5.4% yield) of the title compound was obtained in the same manner as described in Example 138, except that tert-butyl(4-bromo-3-fluorophenyl)sulfonyl(thiazol-2-yl)carbamate 와 ]tert-butyl-4-(5-chloro-2-formylphenyl)-1H- pyrazol-1-carboxylate were used instead of tert-butyl(4-bromophenyl)sulfonyl(thiazol-2-yl)carbamate and 4-chloro-2-(1-methyl-1H-pyrazol-5-yl)benzaldehyde.

$^1$H NMR (CD$_3$OD, 500 MHz) δ 7.67 (1H), 7.53 (3H), 7.34 (3H), 7.25 (1H), 7.02 (1H), 6.95 (1H), 6.60 (1H)

Example 140

Preparation of 4-((4-chloro-2-(furan-3-yl)phenyl)(hydroxy)methyl)-3-fluoro-N-(thiazol-2-yl)benzenesulfonamide

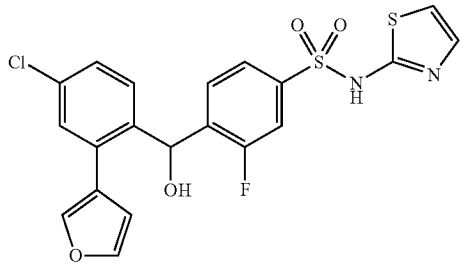 [SMILES: O=S(=O)(Nc1nccs1)c1ccc(C(O)c2ccc(Cl)cc2-c2ccoc2)c(F)c1]

5.45 mg (5.1% yield) of the title compound was obtained in the same manner as described in Example 139, except that 4-chloro-2-(furan-3-yl)benzaldehyde was used instead of tert-butyl-4-(5-chloro-2-formylphenyl)-1H-pyrazol-1-carboxylate.

$^1$H NMR (CD$_3$OD, 500 MHz) δ 7.70 (1H), 7.61 (2H), 7.53 (1H), 7.45 (1H), 7.31 (1H), 7.26 (2H), 7.07 (1H), 6.67 (1H), 6.52 (1H), 6.15 (1H)

Example 141

Preparation of 4-((2,4-di(furan-3-yl)phenyl)(hydroxy)methyl)-3-fluoro-N-(thiazol-2-yl)benzenesulfonamide

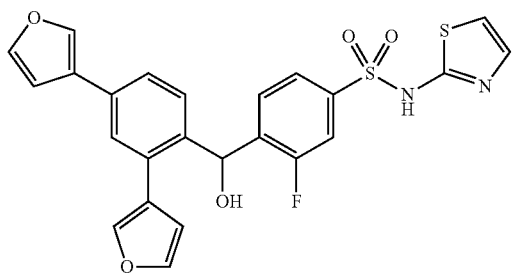 [SMILES: O=S(=O)(Nc1nccs1)c1ccc(C(O)c2ccc(-c3ccoc3)cc2-c2ccoc2)c(F)c1]

5.46 mg (5.0% yield) of the title compound was obtained in the same manner as described in Example 139, except that 2,4-di(furan-3-yl)benzaldehyde was used instead of tert-butyl-4-(5-chloro-2-formylphenyl)-1H-pyrazol-1-carboxylate.

$^1$H NMR (CD$_3$OD, 500 MHz) δ 7.90 (1H), 7.45 (9H), 7.28 (1H), 7.07 (1H), 6.79 (1H), 6.66 (1H), 6.55 (1H), 6.19 (1H)

Example 142

Preparation of 3-fluoro-4-(hydroxy(2-(1-methyl-1H-pyrazol-5-yl)phenyl)methyl)-N-(thiazol-2-yl)benzenesulfonamide

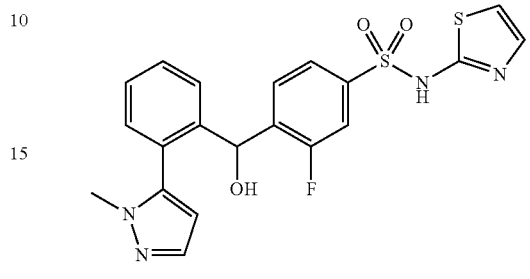

4.40 mg (4.3% yield) of the title compound was obtained in the same manner as described in Example 139, except that 2-(1-methyl-1H-pyrazol-5-yl)benzaldehyde was used instead of tert-butyl-4-(5-chloro-2-formylphenyl)-1H-pyrazol-1-carboxylate.

$^1$H NMR (CD$_3$OD, 500 MHz) δ 7.58 (1H), 7.48 (1H), 7.42 (6H), 7.21 (1H), 7.06 (1H), 6.67 (1H), 6.18 (1H), 5.97 (1H), 3.34 (3H)

Example 143

Preparation of 4-((4-chloro-2-(furan-3-yl)phenyl)(hydroxy)methyl)-N-(thiazol-2-yl)benzenesulfonamide

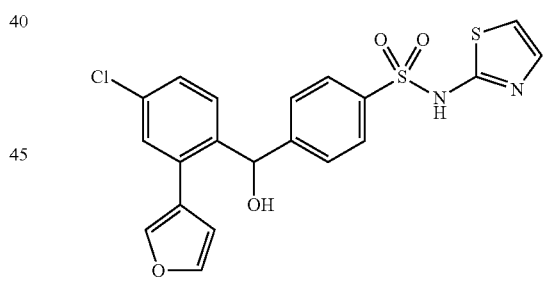

192 mg (0.46 mmol) of tert-butyl(4-bromophenyl)sulfonyl(thiazol-2-yl)carbamate was dissolved in 2 mL of tetrahydrofuran under nitrogen gas, and cooled to −78° C. After adding 0.4 mL (0.64 mmol) of n-butyllithium (1.6M in tetrahydrofuran) slowly, the mixture was stirred for 30 minutes as maintaining −78° C. 47.5 mg (0.23 mmol) of 4-chloro-2-(furan-3-yl)benzaldehyde was dissolved in 0.5 mL of tetrahydrofuran, and added to the above reacting solution. As warming from −78° C. to room temperature, the reacting solution was stirred for 24 hours. Ethyl acetate and water/1 N-hydrochloride were added to the reacting solution, and it was stirred. After separating layers, the organic layer only was collected and concentrated under reduced pressure. The obtained residue was separated by column chromatography (developing solvent, hexane:ethyl acetate=1:1) to obtain 9.9 mg (9.6% yield) of the title compound.

¹H NMR (CD₃OD, 500 MHz) δ 7.78 (m, 2H), 7.56 (s, 2H), 7.35 (m, 1H), 7.31 (m, 4H), 7.06 (m, 1H), 6.67 (m, 1H), 6.53 (s, 1H), 6.00 (s, 1H)

Example 144

Preparation of 4-((4-chloro-2-(1-methyl-1H-pyrazol-5-yl)phenyl)(hydroxy)methyl)-3-fluoro-N-(thiazol-2-yl)benzenesulfonamide

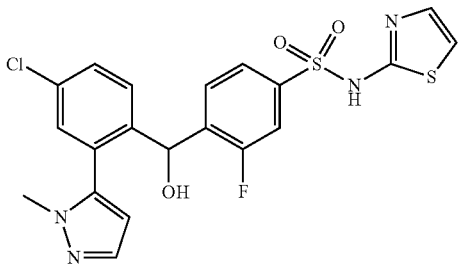 [SMILES: Cn1nccc1-c1cc(Cl)ccc1C(O)c1ccc(S(=O)(=O)Nc2nccs2)cc1F]

10.0 mg (9.6% yield) of the title compound was obtained in the same manner as described in Example 139, except that 4-chloro-2-(1-methyl-1H-pyrazol-5-yl)benzaldehyde was used instead of tert-butyl-4-(5-chloro-2-formylphenyl)-1H-pyrazol-1-carboxylate.

¹H NMR (CD₃OD, 500 MHz) δ 7.58 (1H), 7.48 (1H), 7.42 (5H), 7.21 (1H), 7.06 (1H), 6.67 (1H), 6.18 (1H), 5.97 (1H), 3.34 (3H)

Example 145

Preparation of 4-((4-chloro-2-(pyridin-3-yl)phenyl)(hydroxy)methyl)-3-fluoro-N-(thiazol-2-yl)benzenesulfonamide

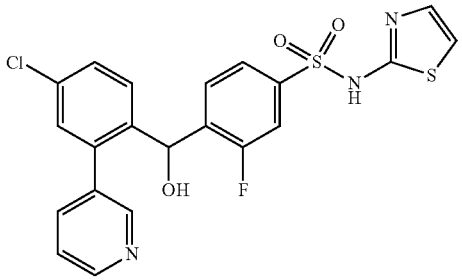 [SMILES: O=S(=O)(Nc1nccs1)c1ccc(C(O)c2ccc(Cl)cc2-c2cccnc2)c(F)c1]

10.0 mg (9.6% yield) of the title compound was obtained in the same manner as described in Example 139, except that 4-chloro-2-(pyridin-3-yl)benzaldehyde was used instead of tert-butyl-4-(5-chloro-2-formylphenyl)-1H-pyrazol-1-carboxylate.

¹H NMR (CDCl₃, 500 MHz) δ 8.73 (1H), 8.26 (1H), 7.87 (1H), 7.66 (4H), 7.43 (2H), 7.10 (3H), 6.88 (1H), 6.55 (1H)

Example 146

Preparation of 4-((4-chloro-2-(pyridin-4-yl)phenyl)(hydroxy)methyl)-3-fluoro-N-(thiazol-2-yl)benzenesulfonamide

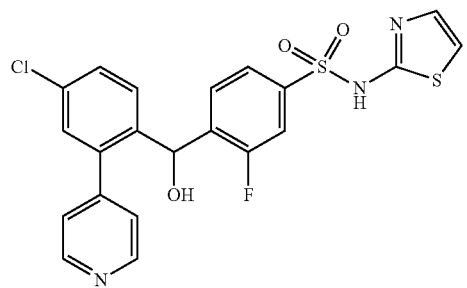 [SMILES: O=S(=O)(Nc1nccs1)c1ccc(C(O)c2ccc(Cl)cc2-c2ccncc2)c(F)c1]

10.0 mg (9.6% yield) of the title compound was obtained in the same manner as described in Example 139, except that 4-chloro-2-(pyridin-2-yl)benzaldehyde was used instead of tert-butyl-4-(5-chloro-2-formylphenyl)-1H-pyrazol-1-carboxylate.

¹H NMR (CDCl₃, 500 MHz) δ 8.42 (1H), 7.88 (1H), 7.84 (1H), 7.34 (4H), 7.16 (1H), 6.95 (1H), 6.85 (1H), 6.52 (1H)

Example 147

Preparation of 4-((4-chloro-2-(pyridin-4-yl)phenyl)(hydroxy)methyl)-N-(thiazol-2-yl)benzenesulfonamide

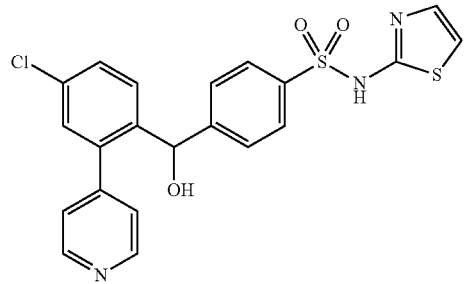 [SMILES: O=S(=O)(Nc1nccs1)c1ccc(C(O)c2ccc(Cl)cc2-c2ccncc2)cc1]

10.0 mg (9.6% yield) of the title compound was obtained in the same manner as described in Example 138, except that -chloro-2-(pyridin-2-yl)benzaldehyde was used instead of 4-chloro-2-(1-methyl-1H-pyrazol-5-yl)benzaldehyde.

¹H NMR (CDCl₃, 500 MHz) δ 8.50 (1H), 7.72 (2H), 7.54 (1H), 7.47 (1H), 7.31 (2H), 7.24 (1H), 7.18 (2H), 7.09 (1H), 6.71 (1H)

Example 148

Preparation of 4-((4-chloro-2-(pyridin-3-yl)phenyl)(hydroxy)methyl)-N-(thiazol-2-yl)benzenesulfonamide

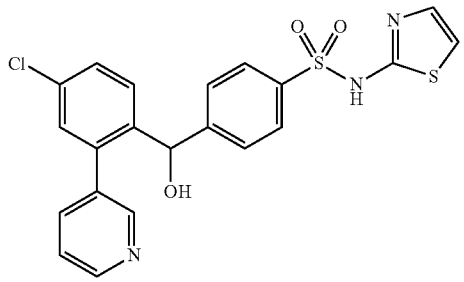 [SMILES: O=S(=O)(Nc1nccs1)c1ccc(C(O)c2ccc(Cl)cc2-c2cccnc2)cc1]

8.6 mg (4.1% yield) of the title compound was obtained in the same manner as described in Example 138, except that 4-chloro-2-(pyridin-3-yl)benzaldehyde was used instead of 4-chloro-2-(1-methyl-1H-pyrazol-5-yl)benzaldehyde.

$^1$H NMR (CD$_3$OD, 500 MHz) δ 8.52 (dd, 1H), 8.44 (s, 1H), 7.73 (d, 2H), 7.66 (d, 1H), 7.56 (d, 1H), 7.47 (dd, 1H), 7.39 (m, 1H), 7.26 (d, 1H), 7.16 (d, 2H), 7.09 (d, 1H), 6.71 (d, 1H), 5.76 (s, 1H)

Example 149

Preparation of 4-((2,4-di(furan-3-yl)phenyl)(hydroxy)methyl)-N-(thiazol-2-yl)benzenesulfonamide

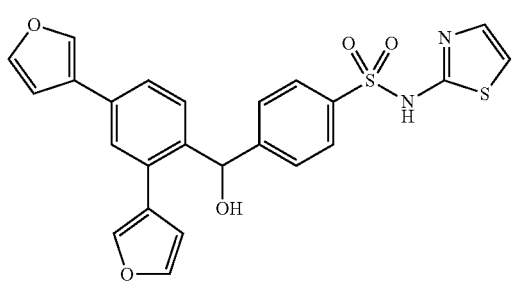 [SMILES: O=S(=O)(Nc1nccs1)c1ccc(C(O)c2ccc(-c3ccoc3)cc2-c2ccoc2)cc1]

5.2 mg (2.4% yield) of the title compound was obtained in the same manner as described in Example 138, except that 2,4-di(furan-3-yl)benzaldehyde was used instead of 4-chloro-2-(1-methyl-1H-pyrazol-5-yl)benzaldehyde.

$^1$H NMR (CD$_3$OD, 500 MHz) δ 7.92 (s, 1H), 7.80 (d, 2H), 7.59-7.50 (m, 5H), 7.36 (d, 3H), 7.08 (d, 1H), 6.81 (s, 1H), 6.70 (d, 1H), 6.59 (s, 1H), 6.05 (s, 1H)

Example 150

Preparation of 4-((4-(2-fluoropyridin-3-yl)-2-(furan-3-yl)phenyl)(hydroxy)methyl)-N-(thiazol-2-yl)benzenesulfonamide

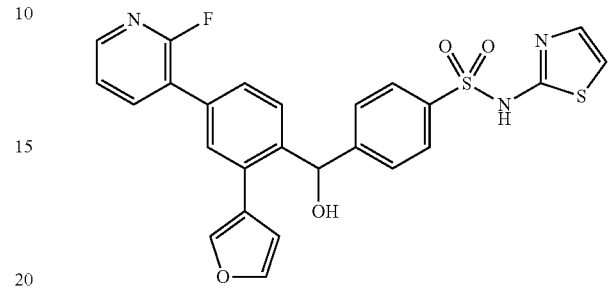

6.9 mg (2.9% yield) of the title compound was obtained in the same manner as described in Example 138, except that 4-(2-fluoropyridin-3-yl)-2-(furan-3-yl)benzaldehyde was used instead of 4-chloro-2-(1-methyl-1H-pyrazol-5-yl)benzaldehyde.

$^1$H NMR (CD$_3$OD, 500 MHz) δ 8.18 (d, 1H), 8.08 (t, 1H), 7.81 (d, 2H), 7.60-7.51 (m, 5H), 7.42-7.37 (m, 3H), 7.08 (d, 1H), 6.70 (d, 1H), 6.60 (s, 1H), 6.11 (s, 1H)

Example 151

Preparation of 4-((4-(6-fluoropyridin-3-yl)-2-(furan-3-yl)phenyl)(hydroxy)methyl)-N-(thiazol-2-yl)benzenesulfonamide

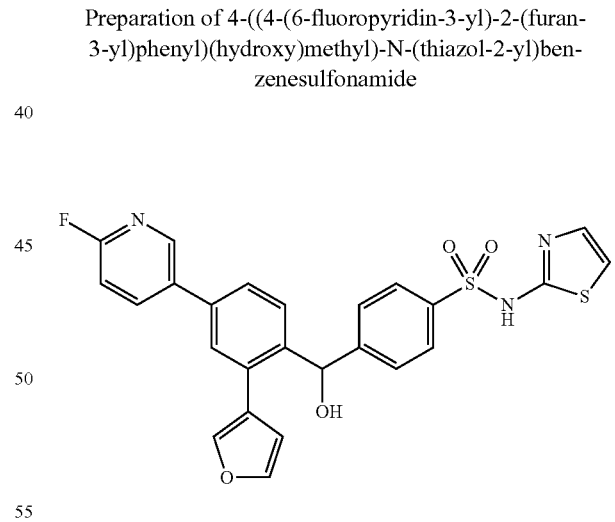

5.8 mg (2.5% yield) of the title compound was obtained in the same manner as described in Example 138, except that 4-(6-fluoropyridin-3-yl)-2-(furan-3-yl)benzaldehyde was used instead of 4-chloro-2-(1-methyl-1H-pyrazol-5-yl)benzaldehyde.

$^1$H NMR (CD$_3$OD, 500 MHz) δ 8.61 (d, 1H), 8.08 (t, 1H), 7.81 (d, 2H), 7.60-7.51 (m, 5H), 7.42-7.37 (m, 3H), 7.08 (d, 1H), 6.70 (d, 1H), 6.60 (s, 1H), 6.11 (s, 1H)

Example 152

Preparation of 4-((2'-fluoro-3-(furan-3-yl)-[1,1'-biphenyl]-4-yl)(hydroxy)methyl)-N-(thiazol-2-yl)benzenesulfonamide

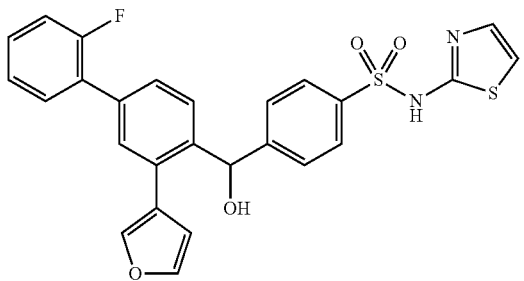 [SMILES: O=S(=O)(Nc1nccs1)c1ccc(C(O)c2ccc(-c3ccccc3F)cc2-c2ccoc2)cc1]

5.2 mg (2.2% yield) of the title compound was obtained in the same manner as described in Example 138, except that 2'-fluoro-3-(furan-3-yl)-[1,1'-biphenyl]-4-carbaldehyde was used instead of 4-chloro-2-(1-methyl-1H-pyrazol-5-yl)benzaldehyde.

$^1$H NMR (CD$_3$OD, 500 MHz) δ 7.81 (d, 2H), 7.57 (d, 2H), 7.47-7.44 (m, 4H), 7.39-7.34 (m, 3H), 7.24-7.14 (m, 2H), 7.07 (d, 1H), 6.68 (d, 1H), 6.58 (s, 1H), 6.10 (s, 1H)

Example 153

Preparation of 4-((3'-fluoro-3-(furan-3-yl)-[1,1'-biphenyl]-4-yl)(hydroxy)methyl)-N-(thiazol-2-yl)benzenesulfonamide

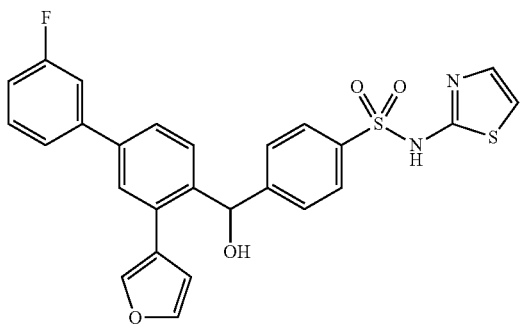 [SMILES: O=S(=O)(Nc1nccs1)c1ccc(C(O)c2ccc(-c3cccc(F)c3)cc2-c2ccoc2)cc1]

4.0 mg (1.7% yield) of the title compound was obtained in the same manner as described in Example 138, except that 3'-fluoro-3-(furan-3-yl)-[1,1'-biphenyl]-4-carbaldehyde was used instead of 4-chloro-2-(1-methyl-1H-pyrazol-5-yl)benzaldehyde.

$^1$H NMR (CD$_3$OD, 500 MHz) δ 7.81 (d, 2H), 7.61-7.55 (m, 4H), 7.48-7.43 (m, 3H), 7.37 (d, 3H), 7.08 (d, 2H), 6.70 (d, 1H), 6.61 (s, 1H), 6.10 (s, 1H)

Example 154

Preparation of 4-((4'-fluoro-3-(furan-3-yl)-[1,1'-biphenyl]-4-yl)(hydroxy)methyl)-N-(thiazol-2-yl)benzenesulfonamide

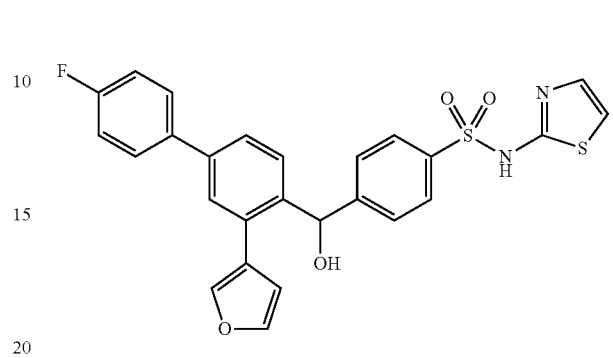

4.6 mg (2.0% yield) of the title compound was obtained in the same manner as described in Example 138, except that 4'-fluoro-3-(furan-3-yl)-[1,1'-biphenyl]-4-carbaldehyde was used instead of 4-chloro-2-(1-methyl-1H-pyrazol-5-yl)benzaldehyde.

$^1$H NMR (CD$_3$OD, 500 MHz) δ 7.81 (d, 2H), 7.58-7.53 (m, 6H), 7.45 (d, 1H), 7.38 (d, 2H), 7.16 (t, 2H), 7.09 (d, 1H), 6.71 (d, 1H), 6.61 (d, 1H), 6.09 (s, 1H)

Example 155

Preparation of 3-fluoro-4-((2-(furan-3-yl)pyridin-3-yl)(hydroxy)methyl)-N-(thiazol-2-yl)benzenesulfonamide

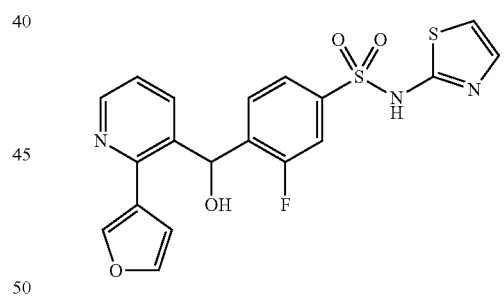

100 mg (0.26 mmol) of tert-butyl((3,4-difluorophenyl)sulfonyl)(thiazol-2-yl)carbamate was dissolved in 5 mL of tetrahydrofuran under nitrogen gas, and cooled to −78° C. After adding 0.25 mL (0.39 mmol) of n-butyllithium (1.6M in tetrahydrofuran) slowly, the mixture was stirred for 30 minutes as maintaining −78° C. 23 mg (0.13 mmol) of 2-(furan-3-yl)nicotinaldehyde was dissolved in 0.5 mL of tetrahydrofuran, and added to the above reacting solution. As warming from −78° C. to room temperature, the reacting solution was stirred for 24 hours. Ethyl acetate and water/1 N-hydrochloride were added to the reacting solution, and it was stirred. After separating layers, the organic layer only was collected and concentrated under reduced pressure. The obtained residue was separated by column chromatography (developing solvent, hexane:ethyl acetate=1:1) to obtain 7 mg (6.1% yield) of the title compound.

$^1$H NMR (CD$_3$OD, 500 MHz) δ 8.48 (m, 1H), 7.84 (s, 1H), 7.72 (m, 3H), 7.59 (m, 1H), 7.47 (m, 1H), 7.32 (m, 1H), 7.70 (m, 1H), 6.73 (m, 2H), 6.24 (s, 1H)

Example 156

Preparation of 4-((2-(furan-3-yl)pyridin-3-yl)(hydroxy)methyl)-N-(thiazol-2-yl)benzenesulfonamide

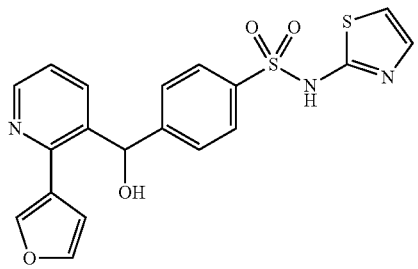 [SMILES: O=S(=O)(Nc1nccs1)c1ccc(C(O)c2cccnc2-c2ccoc2)cc1]

100 mg (0.28 mmol) of tert-butyl((4-fluorophenyl)sulfonyl)(thiazol-2-yl)carbamate was dissolved in 5 mL of tetrahydrofuran under nitrogen gas, and cooled to −78° C. After adding 0.26 mL (0.42 mmol) of n-butyllithium (1.6 M in tetrahydrofuran) slowly, the mixture was stirred for 30 minutes as maintaining −78° C. 23 mg (0.13 mmol) of 2-(furan-3-yl)nicotinaldehyde was dissolved in 0.5 mL of tetrahydrofuran, and added to the above reacting solution. As warming from −78° C. to room temperature, the reacting solution was stirred for 24 hours. Ethyl acetate and water/1 N-hydrochloride were added to the reacting solution, and it was stirred. After separating layers, the organic layer only was collected and concentrated under reduced pressure. The obtained residue was separated by column chromatography (developing solvent, hexane:ethyl acetate=1:1) to obtain 6 mg (5.2% yield) of the title compound.

$^1$H NMR (CD$_3$OD, 500 MHz) δ 8.48 (m, 1H), 7.81 (m, 4H), 7.59 (m, 1H), 7.36 (m, 3H), 7.09 (m, 1H), 6.73 (m, 2H), 6.09 (s, 1H)

Example 157

Preparation of 3-fluoro-4-(hydroxy(2-phenylpyridin-3-yl)methyl)-N-(thiazol-2-yl)benzenesulfonamide

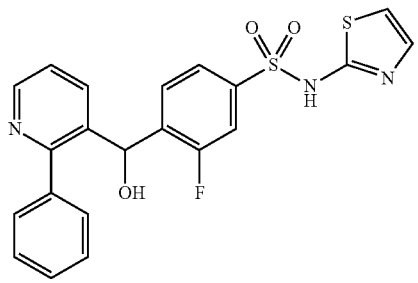 [SMILES: O=S(=O)(Nc1nccs1)c1ccc(C(O)c2cccnc2-c2ccccc2)c(F)c1]

100 mg (0.26 mmol) of tert-butyl((3,4-difluorophenyl)sulfonyl)(thiazol-2-yl)carbamate was dissolved in 5 mL of tetrahydrofuran under nitrogen gas, and cooled to −78° C. After adding 0.25 mL (0.39 mmol) of n-butyllithium (1.6 M in tetrahydrofuran) slowly, the mixture was stirred for 30 minutes as maintaining −78° C. 24.3 mg (0.13 mmol) of 2-phenylnicotinaldehyde was dissolved in 0.5 mL of tetrahydrofuran, and added to the above reacting solution. As warming from −78° C. to room temperature, the reacting solution was stirred for 24 hours. Ethyl acetate and water/1 N-hydrochloride were added to the reacting solution, and it was stirred. After separating layers, the organic layer only was collected and concentrated under reduced pressure. The obtained residue was separated by column chromatography (developing solvent, hexane:ethyl acetate=1:1) to obtain 9 mg (7.6% yield) of the title compound.

$^1$H NMR (CD$_3$OD, 500 MHz) δ 8.49 (m, 1H), 7.95 (m, 1H), 7.64 (m, 1H), 7.52 (m, 1H), 7.42 (m, 1H), 7.37 (m, 6H), 7.12 (m, 1H), 6.74 (m, 1H), 6.09 (s, 1H)

Experimental Example

Experiment on Blocking Effect Against Sodium Ion Channel (Nav1.7)

In order to measure the activities of the inventive compounds as antagonists, an experiment on a blocking effect against the sodium ion channel (Nav1.7) was carried out as follows.

1) Cell Culture

The hNav1.7 HEK293 cell line used was a cell line having a human sodium ion channel 1.7 gene (type IX voltage-gated sodium channel alpha subunit) (type IX voltage-gated sodium channel alpha subunit) in human embryonic kidney (HEK) 293 cells and was purchased from Millipore. The medium used was prepared by adding 1% 100×NEAA and 10% heat inactivated FBS to DMEM F-12 and adding 1% P/S as an antibiotic thereto. G-418 as a restriction enzyme was added during subculture, and the hNav1.7 HEK293 cells were cultured to a confluence of about 80% in a T75 flask in a 5% CO2 incubator at 37° C. for 2 or 3 days and detached from the flask by treatment with 0.25% trypsin solution. Then, the cells were collected by centrifugation and used in the experiment.

2) Preparation of Compound Samples

The compounds prepared in the Examples of the present invention were dissolved in dimethyl sulfoxide (DMSO) and used in the experiment. 90 mM and 10 mM DMSO stock solutions were prepared from each of the compounds and diluted in an extracellular solution (4 mM KCl, 138 mM NaCl, 1 mM MgCl$_2$, 1.8 mM CaCl$_2$, 5.6 mM glucose, 10 mM HEPES, pH 7.45) at various concentrations so that the final concentration of each compound in DMSO was 0.3% or less.

3) Measurement of Sodium Ion Channel Blocking Effects

To measure the sodium ion channel blocking effect, an IonFlux16 Auto patch clamp system (Fluxion, Inc.) and a plate for exclusive use were used. The cells were distributed in an extracellular solution (4 mM KCl, 138 mM NaCl, 1 mM MgCl$_2$, 1.8 mM CaCl$_2$, 5.6 mM glucose, 10 mM HEPES, pH 7.45), and then dispensed in the specified region of the plate, and each of the prepared compound samples was diluted at various concentrations, and then dispensed in the specified region of the plate. After the dispensation of the cells, the compound samples and an intracellular solution (100 mM CsF, 45 mM CsCl, 5 mM NaCl, 5 mM EGTA, 10 mM HEPES, pH 7.2) in the plate has been completed, the plate was mounted in the patch clamp system, and whether the compounds inhibited the ion channel was measured according to a set program and pulse protocol.

Specifically, eight concentrations per compound were set, and percent inhibition was determined by calculating the percentage of inhibition of the peak current, generated after treating the cells with each concentration of the compound for 50 seconds, relative to the peak current generated before treatment with the compound, and the IC50 value was calculated using the Sigma plot program. The results of the calculation are shown in Table 2 below. In Table 2 below, the percent inhibition of Nav1.7 is rated as follows:

Nav1.7 IC50: +(>100 nM), ++(51-100 nM), and +++(<50 nM)

TABLE 2

| Example No. | Nav1.7 IC$_{50}$ |
|---|---|
| 1 | +++ |
| 2 | + |
| 3 | +++ |
| 4 | ++ |
| 5 | +++ |
| 6 | + |
| 7 | ++ |
| 8 | + |
| 9 | ++ |
| 10 | ++ |
| 11 | ++ |
| 12 | +++ |
| 13 | + |
| 14 | + |
| 15 | + |
| 16 | +++ |
| 17 | + |
| 18 | + |
| 19 | + |
| 20 | + |
| 21 | + |
| 22 | ++ |
| 23 | + |
| 24 | + |
| 25 | + |
| 26 | ++ |
| 27 | + |
| 28 | + |
| 29 | + |
| 30 | + |
| 31 | ++ |
| 32 | + |
| 33 | + |
| 34 | + |
| 35 | + |
| 36 | + |
| 37 | + |
| 38 | + |
| 39 | ++ |
| 40 | + |
| 41 | + |
| 42 | + |
| 43 | + |
| 44 | + |
| 45 | + |
| 46 | + |
| 47 | + |
| 48 | + |
| 49 | + |
| 50 | +++ |
| 51 | + |
| 52 | + |
| 53 | + |
| 54 | + |
| 55 | + |
| 56 | + |
| 57 | + |
| 58 | + |
| 59 | + |
| 60 | + |

TABLE 3

| Example No. | Nav1.7 IC$_{50}$ |
|---|---|
| 61 | + |
| 62 | + |
| 63 | + |
| 64 | + |
| 65 | + |
| 66 | + |
| 67 | + |
| 68 | + |
| 69 | + |
| 70 | + |
| 71 | + |
| 72 | + |
| 73 | + |
| 74 | + |
| 75 | + |
| 76 | + |
| 77 | + |
| 78 | + |
| 79 | + |
| 80 | + |
| 81 | + |
| 82 | + |
| 83 | + |
| 84 | + |
| 85 | + |
| 86 | + |
| 87 | + |
| 88 | + |
| 89 | + |
| 90 | + |
| 91 | + |
| 92 | + |
| 93 | + |
| 94 | + |
| 95 | + |
| 96 | + |
| 97 | + |
| 98 | + |
| 99 | + |
| 100 | + |
| 101 | ++ |
| 102 | + |
| 103 | + |
| 104 | ++ |
| 105 | + |
| 106 | + |
| 107 | + |
| 108 | ++ |
| 109 | +++ |
| 110 | +++ |
| 111 | + |
| 112 | ++ |
| 113 | + |
| 114 | + |
| 115 | + |
| 116 | + |
| 117 | ++ |
| 118 | + |
| 119 | ++ |
| 120 | + |

TABLE 4

| Example No. | Nav1.7 IC$_{50}$ |
|---|---|
| 121 | + |
| 122 | ++ |
| 123 | + |
| 124 | + |
| 125 | + |
| 126 | + |
| 127 | ++ |
| 128 | + |

TABLE 4-continued

| Example No. | Nav1.7 IC$_{50}$ |
|---|---|
| 129 | + |
| 130 | + |
| 131 | ++ |
| 132 | + |
| 133 | + |
| 134 | + |
| 135 | + |
| 136 | + |
| 137 | + |
| 138 | + |
| 139 | + |
| 140 | + |
| 141 | + |
| 142 | + |
| 143 | +++ |
| 144 | + |
| 145 | + |
| 146 | + |
| 147 | + |
| 148 | + |
| 149 | + |
| 150 | + |
| 151 | + |
| 152 | + |
| 153 | ++ |
| 154 | + |
| 155 | + |
| 156 | + |
| 157 | + |

The invention claimed is:

1. A compound represented by the following formula 1 or a pharmaceutically acceptable salt thereof:

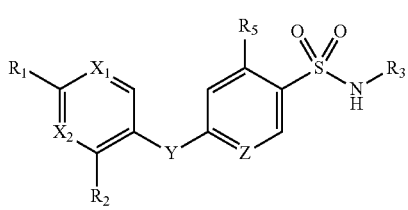

[Formula 1]

wherein $R_1$ is hydrogen, halogen, or aryl or heteroaryl selected from the group consisting of phenyl, pyridinyl, pyrimidinyl, furanyl, isoxazolyl, pyrazolyl and thienyl,
wherein the aryl or heteroaryl is unsubstituted or substituted by one or two substituents independently selected from the group consisting of $C_{1-4}$ alkyl, $C_{1-4}$ haloalkyl and halogen, $R_2$ is aryl or heteroaryl selected from the group consisting of furanyl, imidazolyl, isoxazolyl, phenyl, pyrazolyl, pyridinyl, pyrimidinyl, thiazolyl and thienyl,
wherein the aryl or heteroaryl is unsubstituted or substituted by one or two substituents independently selected from the group consisting of $C_{1-4}$ alkyl, $C_{3-6}$ cycloalkyl, halogen, morpholino, piperazinyl, piperidinyl, pyridinyl and pyrrolidinyl, $R_3$ is thiazolyl or thiadiazolyl,
$X_1$ is CH or N, $X_2$ is CH or N, with the proviso that at least one among $X_1$ and $X_2$ is CH,
Y is O or CH(OH),
Z is $CR_4$,
$R_4$ is H, halogen or CN,
$R_5$ is H or halogen, with the proviso that
if $R_2$ is pyrazolyl subsitituted by $C_{1-4}$ alkyl, one among $X_1$ and $X_2$ is N, and
if $R_1$ is H or halogen, Y is CH(OH).

2. The compound or pharmaceutically acceptable salt thereof of claim 1, wherein $R_1$ is H; chloro; phenyl unsubstituted or substituted by one or two substituents independently selected from the group consisting of $C_{1-4}$ haloalkyl and halogen; pyridinyl unsubstituted or substituted by one or two halogens; unsubstituted pyrimidinyl; unsubstituted furanyl; unsubstituted isoxazolyl; pyrazolyl unsubstituted or substituted by $C_{1-4}$ alkyl; or unsubstituted thienyl.

3. The compound or pharmaceutically acceptable salt thereof of claim 2, wherein $R_1$ is H; chloro; phenyl unsubstituted or substituted by one or two substituents independently selected from the group consisting of $CF_3$, F and Cl;
pyridinyl unsubstituted or substituted by one or two F; unsubstituted pyrimidinyl;
unsubstituted furanyl; unsubstituted isoxazolyl; pyrazolyl unsubstituted or substituted by methyl; or unsubstituted thienyl.

4. The compound or pharmaceutically acceptable salt thereof of claim 1, wherein $R_2$ is unsubstituted furanyl; imidazolyl substituted by pyridinyl; isoxazolyl substituted by two $C_{1-4}$ alkyl; unsubstituted phenyl; pyrazolyl unsubstituted or substituted by $C_{1-4}$ alkyl or $C_{3-6}$ cycloalkyl; pyridinyl unsusbtituted or substituted by one or two substituents selected from the group consisting of $C_{1-4}$ alkyl, halogen, morpholino, piperidinyl and pyrrolidinyl; pyrimidinyl unsubstituted or substituted by piperazinyl; thiazolyl substituted by $C_{3-6}$ cycloalkyl; or thienyl substituted by one or two $C_{1-4}$ alkyl.

5. The compound or pharmaceutically acceptable salt thereof of claim 4, wherein $R_2$ is unsubstituted furanyl; imidazolyl substituted by pyridinyl; isoxazolyl substituted by two methyl; unsubstituted phenyl; pyrazolyl unsubstituted or substituted by methyl or cyclopropyl; pyridinyl unsusbtituted or substituted by one or two substituents selected from the group consisting of methyl, F, Cl, morpholino, piperidinyl and pyrrolidinyl; pyrimidinyl unsubstituted or substituted by piperazinyl; thiazolyl substituted by cyclopropyl; or thienyl substituted by one or two methyl.

6. The compound or pharmaceutically acceptable salt thereof of claim 1, wherein $R_4$ is H, F, Cl or CN.

7. The compound or pharmaceutically acceptable salt thereof of claim 1, wherein $R_5$ is H or F.

8. The compound or pharmaceutically acceptable salt thereof of claim 1, wherein
$R_1$ is aryl or heteroaryl selected from the group consisting of phenyl, pyridinyl, pyrimidinyl, furanyl, isoxazolyl, pyrazolyl and thienyl,
wherein the aryl or heteroaryl is unsubstituted or substituted by one or two substituents independently selected from the group consisting of $C_{1-4}$ alkyl, $C_{1-4}$ haloalkyl and halogen,
$R_2$ is aryl or heteroaryl selected from the group consisting of furanyl, imidazolyl, isoxazolyl, pyrazolyl, pyridinyl, pyrimidinyl, thiazolyl and thienyl,
wherein the aryl or heteroaryl is unsubstituted or substituted by one or two substituents independently selected from the group consisting of $C_{1-4}$ alkyl, $C_{3-6}$ cycloalkyl, halogen, morpholino, piperazinyl, piperidinyl, pyridinyl and pyrrolidinyl,
$R_3$ is thiazolyl or thiadiazolyl,
$X_1$ is CH or N, $X_2$ is CH or N, with the proviso that at least one among $X_1$ and $X_2$ is CH,
Y is O, Z is CR$_4$,
R$_4$ is H, halogen or CN,
R$_5$ is H or halogen.

9. The compound or pharmaceutically acceptable salt thereof of claim 1, wherein
R$_1$ is hydrogen, halogen, or aryl or heteroaryl selected from the group consisting of phenyl, pyridinyl and furanyl, wherein the aryl or heteroaryl is unsubstituted or substituted by halogen,
R$_2$ is aryl or heteroaryl selected from the group consisting of furanyl, phenyl, pyrazolyl and pyridinyl, wherein the aryl or heteroaryl is unsubstituted or substituted by C$_{1-4}$ alkyl,
R$_3$ is thiazolyl,
X$_1$ is CH or N, X$_2$ is CH or N, with the proviso that at least one among X$_1$ and X$_2$ is CH,
Y is CH(OH),
Z is CR$_4$,
R$_4$ is H or halogen,
R$_5$ is H.

10. The compound or pharmaceutically acceptable salt thereof of claim 1, wherein the compound is selected from the group consisting of
1) 3-cyano-4-((4-(furan-3-yl)-6-phenylpyridin-3-yl)oxy)-N-(thiazol-2-yl) benzenesulfonamide,
2) 3-cyano-4-((4-(1-methyl-1H-pyrazol-5-yl)-6-phenylpyridin-3-yl)oxy)-N -(thiazol-2-yl) benzenesulfonamide,
3) 3-cyano-4-((4-(furan-3-yl)-6-phenylpyridin-3-yl)oxy)-N-(1,2,4-thiadiazol-5-yl)benzenesulfonamide,
4) 3-cyano-4-((4-(1-methyl-1H-pyrazol-5-yl)-6-phenylpyridin-3-yl)oxy)-N-(1,2,4-thiadiazol-5-yl)benzenesulfonamide,
5) 3-cyano-4-(6-(3-fluorophenyl)-4-(furan-3-yl)pyridin-3-yloxy)-N-(thiazol-2-yl)benzenesulfonamide,
6) 3-cyano-4-(6-(2-fluorophenyl)-4-(furan-3-yl)pyridin-3-yloxy)-N-(thiazol-2-yl)benzenesulfonamide,
7) 3-cyano-4-(6-(4-fluorophenyl)-4-(furan-3-yl)pyridin-3-yloxy)-N-(thiazol-2-yl)benzenesulfonamide,
8) 3-cyano-4-(4-(furan-3-yl)-6-(3-(trifluoromethyl)phenyl)pyridin-3-yloxy)-N-(thiazol -2-yl)benzenesulfonamide,
9) 3-cyano-4-(2'-fluoro-4-(furan-3-yl)-2,4'-bipyridin-5-yloxy)-N-(thiazol-2-yl)benzenesulfonamide,
10) 3-cyano-4-(2'-fluoro-4-(furan-3-yl)-2,3'-bipyridin-5-yloxy)-N-(thiazol-2-yl)benzenesulfonamide,
11) 3-cyano-4-(6'-fluoro-4-(furan-3-yl)-2,3'-bipyridin-5-yloxy)-N-(thiazol-2-yl)benzenesulfonamide,
12) 3-cyano-4-(2',6'-difluoro-4-(furan-3-yl)-2,3'-bipyridin-5-yloxy)-N-(thiazol-2-yl)benzenesulfonamide,
13) 3-cyano-4-(4-(furan-3-yl)-2,3'-bipyridin-5-yloxy)-N-(thiazol-2-yl)benzenesulfonamide,
14) 3-cyano-4-(4-(furan-3-yl)-2,4'-bipyridin-5-yloxy)-N-(thiazol-2-yl)benzenesulfonamide,
15) 3-cyano-4-(4-(furan-3-yl)-6-(pyrimidin-5-yl)pyridin-3-yloxy)-N-(thiazol-2-yl)benzenesulfonamide,
16) 3-cyano-4-((4,6-di(furan-3-yl)pyridin-3-yl)oxy)-N-(thiazol-2-yl)benzenesulfonamide,
17) 4-((4,6-di(furan-3-yl)pyridin-3-yl)oxy)-3-fluoro-N-(thiazol-2-yl)benzenesulfonamide,
18) 3-cyano-4-((2'-fluoro-4-(1-methyl-1H-pyrazol-5-yl)-[2,3'-bipyridin]-5-yl)oxy)-N -(thiazol-2-yl)benzenesulfonamide,
19) 3-cyano-4-((6'-fluoro-4-(1-methyl-1H-pyrazol-5-yl)-[2,3'-bipyridin]-5-yl)oxy)-N -(thiazol-2-yl)benzenesulfonamide,
20) 3-cyano-4-((4-(furan-3-yl)-6-(thiophen-3-yl)pyridin-3-yl)oxy)-N-(thiazol-2-yl) benzenesulfonamide,
21) 3-fluoro-4-((4-(1-methyl-1H-pyrazol-5-yl)-[2,3'-bipyridin]-5-yl)oxy)-N -(thiazol-2-yl)benzenesulfonamide,
22) 3-fluoro-4-((4-(1-methyl-1H-pyrazol-5-yl)-6-(thiophen-3-yl)pyridin-3-yl)oxy)-N -(thiazol-2-yl)benzenesulfonamide,
23) 3-cyano-4-((6-(4-fluorophenyl)-4-(1-methyl-1H-pyrazol-5-yl)pyridin-3-yl)oxy) -N-(thiazol-2-yl)benzenesulfonamide,
24) 3-cyano-4-((6-(2-fluorophenyl)-4-(1-methyl-1H-pyrazol-5-yl)pyridin-3-yl)oxy) -N-(thiazol-2-yl)benzenesulfonamide,
25) 3-cyano-4-((6-(furan-3-yl)-4-(1-methyl-1H-pyrazol-5-Apyridin-3-yl)oxy)-N -(thiazol-2-Abenzenesulfonamide,
26) 3-cyano-4-((6-(3-fluorophenyl)-4-(1-methyl-1H-pyrazol-5-yl)pyridin-3-yl)oxy) -N-(thiazol-2-yl)benzenesulfonamide,
27) 3-cyano-4-((2'-fluoro-4-(1-methyl-1H-pyrazol-5-yl)-[2,4'-bipyridin]-5-yl)oxy)-N-(thiazol-2-yl)benzenesulfonamide,
28) 4-((4,6-di(furan-3-yl)pyridin-3-yl)oxy)-N-(thiazol-2-yl)benzenesulfonamide, 129) 3-cyano-4-((2-fluoro-6'-phenyl-[3,4'-bipyridin]-3'-yl)oxy)-N-(thiazol-2-yl)benzenesulfonamide,
30) 3-cyano-4-((6-fluoro-6'-phenyl-[3,4'-bipyridin]-3'-yl)oxy)-N-(thiazol-2-yl)benzenesulfonamide,
31) 3-cyano-4-((2'-fluoro-6-phenyl-[4,4'-bipyridin]-3-yl)oxy)-N-(thiazol-2-yl)benzenesulfonamide,
32) 3-cyano-4-((6-fluoro-5-methyl-6'-phenyl-[3,4'-bipyridin]-3'-yl)oxy)-N-(thiazol-2-yl)benzenesulfonamide,
33) 3-cyano-4-((6'-phenyl-[3,4'-bipyridin]-3'-yl)oxy)-N-(thiazol-2-yl)benzenesulfonamide,
34) 3-cyano-4-((6-phenyl-4-(pyrimidin-5-yl)pyridin-3-yl)oxy)-N-(thiazol-2-yl)benzenesulfonamide,
35) 4-((3'-chloro-6-phenyl-[4,4'-bipyridin]-3-yl)oxy)-3-cyano-N-(thiazol-2-yl)benzenesulfonamide,
36) 3-cyano-4-((2',3'-dichloro-6-phenyl-[4,4'-bipyridin]-3-yl)oxy)-N-(thiazol-2-yl)benzenesulfonamide,
37) 3-cyano-4-((4-(3,5-dimethylisoxazol-4-yl)-6-phenylpyridin-3-yl)oxy)-N-(thiazol-2-yl)benzenesulfonamide,
38) 3-cyano-4-((4-(1-methyl-1H-pyrazol-4-yl)-6-phenylpyridin-3-yl)oxy)-N-(thiazol-2-yl)benzenesulfonamide,
39) 3-cyano-4-((6-phenyl-4-(1H-pyrazol-4-yl)pyridin-3-yl)oxy)-N-(thiazol-2-yl)benzenesulfonamide,
40) 3-cyano-4-((6-phenyl-[4,4'-bipyridin]-3-yl)oxy)-N-(thiazol-2-yl)benzenesulfonamide,
41) 3-cyano-4-((4-(2,5-dimethylthiophen-3-yl)-6-phenylpyridin-3-yl)oxy)-N-(thiazol-2-yl)benzenesulfonamide,
42) 3-cyano-4-((4-(5-methylthiophen-2-yl)-6-phenylpyridin-3-yl)oxy)-N-(thiazol-2-yl)benzenesulfonamide,
43) 3-cyano-4-((4-(2-cyclopropylthiazol-4-yl)-6-phenylpyridin-3-yl)oxy)-N-(thiazol-2-yl)benzenesulfonamide,
44) 3-cyano-4-((4-(1-cyclopropyl-1H-pyrazol-4-yl)-6-phenylpyridin-3-yl)oxy)-N-(thiazol-2-yl)benzenesulfonamide,
45) 3-cyano-4-((4-(furan-3-yl)-6-(1H-pyrazol-4-yl)pyridin-3-yl)oxy)-N-(thiazol-2-yl)benzenesulfonamide,
46) 3-cyano-4-((4-(furan-3-yl)-6-(1-methyl-1H-pyrazol-4-yl)pyridin-3-yl)oxy)-N-(thiazol-2-yl)benzenesulfonamide, 47) 3-fluoro-4-((2'-fluoro-4-(furan-3-yl)-[2,3'-bipyridin]-5-yl)oxy)-N-(thiazol-2-yl)benzenesulfonamide,
48) 3-fluoro-4-((6'-fluoro-4-(furan-3-yl)-[2,3'-bipyridin]-5-yl)oxy)-N-(thiazol-2-yl)benzenesulfonamide,
49) 3-cyano-4-((6-fluoro-[3,2':4',3''-terpyridin]-5'-yl)oxy)-N-(thiazol-2-yl)benzenesulfonamide,
50) 3-cyano-4-((6'-(3-fluorophenyl)-[3,4'-bipyridin]-3'-yl)oxy)-N-(thiazol-2-yl)benzenesulfonamide,
51) 3-cyano-4-((2-fluoro-[3,2':4',3''-terpyridin]-5'-yl)oxy)-N-(thiazol-2-yl)benzenesulfonamide,
52) 3-cyano-4-((6'-(2-fluorophenyl)-[3,4'-bipyridin]-3'-yl)oxy)-N-(thiazol-2-yl)benzenesulfonamide,
53) 3-cyano-4-((2,6-difluoro-[3,2':4',4''-terpyridin]-5'-yl)oxy)-N-(thiazol-2-yl)benzenesulfonamide,
54) 4-((4,6-bis(1-methyl-1H-pyrazol-4-yl)pyridin-3-yl)oxy)-3-cyano-N-(thiazol-2-yl)benzenesulfonamide,
55) 4-((4,6-bis(1-methyl-1H-pyrazol-4-yl)pyridin-3-yl)oxy)-3-cyano-N-(1,2,4-thiadiazol-5-yl)benzenesulfonamide,
56) 5-chloro-2-fluoro-4-((2'-fluoro-4-(furan-3-yl)-[2,3'-bipyridin]-5-yl)oxy)-N-(thiazol-4-yl)benzenesulfonamide,
57) 5-chloro-2-fluoro-4-((6'-fluoro-4-(furan-3-yl)-[2,3'-bipyridin]-5-yl)oxy)-N-(thiazol-4-yl)benzenesulfonamide,
58) 5-chloro-4-((2',6'-difluoro-4-(furan-3-yl)-[2,3'-bipyridin]-5-yl)oxy)-2-fluoro-N-(thiazol-4-yl)benzenesulfonamide,
59) 5-chloro-2-fluoro-4-((6-(3-fluorophenyl)-4-(furan-3-yl)pyridin-3-yl)oxy)-N-(thiazol-4-yl)benzenesulfonamide,
60) 5-chloro-2-fluoro-4-((6-(2-fluorophenyl)-4-(furan-3-yl)pyridin-3-yl)oxy)-N-(thiazol-4-yl)benzenesulfonamide,
61) 5-chloro-2-fluoro-4-((6-(4-fluorophenyl)-4-(furan-3-yl)pyridin-3-yl)oxy)-N-(thiazol-4-yl)benzenesulfonamide,
62) 5-chloro-2-fluoro-4-((2'-fluoro-4-(furan-3-yl)-[2,4'-bipyridin]-5-yl)oxy)-N-(thiazol-4-yl)benzenesulfonamide,
63) 5-chloro-2-fluoro-4-((6-(2-fluorophenyl)-4-(1-methyl-1H-pyrazol-4-yl)pyridin-3-yl)oxy)-N-(thiazol-4-yl)benzenesulfonamide 2,2,2-trifluoroacetate,
64) 5-chloro-2-fluoro-4-((6-(3-fluorophenyl)-4-(1-methyl-1H-pyrazol-5-yl)pyridin-3-yl)oxy)-N-(thiazol-2-yl)benzenesulfonamide,
65) 5-chloro-2-fluoro-4-((6-(4-fluorophenyl)-4-(1-methyl-1H-pyrazol-4-yl)pyridin-3-yl)oxy)-N-(thiazol-4-yl)benzenesulfonamide 2,2,2-trifluoroacetate,
66) 5-chloro-4-((6-(2,4-difluorophenyl)-4-(1-methyl-1H-pyrazol-4-yl)pyridin-3-yl)oxy)-2-fluoro-N-(thiazol-4-yl)benzenesulfonamide 2,2,2-trifluoroacetate,
67) 5-chloro-4-((6-(3,4-difluorophenyl)-4-(1-methyl-1H-pyrazol-4-yl)pyridin-3-yl)oxy)-2-fluoro-N-(thiazol-4-yl)benzenesulfonamide 2,2,2-trifluoroacetate,
68) 5-chloro-2-fluoro-4-((2'-fluoro-4-(1-methyl-1H-pyrazol-4-yl)-[2,4'-bipyridin]-5-yl)oxy)-N-(thiazol-4-yl)benzenesulfonamide 2,2,2-trifluoroacetate,
69) 5-chloro-2-fluoro-4-((2'-fluoro-4-(1-methyl-1H-pyrazol-4-yl)-[2,3'-bipyridin]-5-yl)oxy)-N-(thiazol-4-yl)benzenesulfonamide 2,2,2-trifluoroacetate,
70) 5-chloro-2-fluoro-4-((6'-fluoro-4-(1-methyl-1H-pyrazol-4-yl)-[2,3'-bipyridin]-5-yl)oxy)-N-(thiazol-4-yl)benzenesulfonamide 2,2,2-trifluoroacetate,
71) 5-chloro-2-fluoro-4-((6-(3-fluorophenyl)-4-(1-methyl-1H-pyrazol-5-yl)pyridin-3-yl)oxy)-N-(thiazol-4-yl)benzenesulfonamide,
72) 5-chloro-2-fluoro-4-((6-(3-fluorophenyl)-4-(2-(piperazin-1-yl)pyrimidin-4-yl)pyridin-3-yl)oxy)-N-(thiazol-4-yl)benzenesulfonamide,
73) 5-chloro-2-fluoro-4-((6'-(3-fluorophenyl)-[3,4'-bipyridin]-3'-yl)oxy)-N-(thiazol-2-yl)benzenesulfonamide,
74) 5-chloro-2-fluoro-4-((6'-(3-fluorophenyl)-[3,4'-bipyridin]-3'-yl)oxy)-N-(thiazol-4-yl)benzenesulfonamide,
75) 5-chloro-2-fluoro-4-((2''-fluoro-[3,4':2',4''-terpyridin]-5'-yl)oxy)-N-(thiazol-4-yl)benzenesulfonamide,
76) 5-chloro-2-fluoro-4-((6-(3-fluorophenyl)-4-(pyrimidin-5-yl)pyridin-3-yl)oxy)-N-(thiazol-4-yl)benzenesulfonamide,
77) 5-chloro-2-fluoro-4-((2'-fluoro-4-(pyrimidin-5-yl)-[2,4'-bipyridin]-5-yl)oxy)-N-(thiazol-4-yl)benzenesulfonamide,
78) 5-chloro-2-fluoro-4-((6-(3-fluorophenyl)-4-(1H-pyrazol-4-yl)pyridin-3-yl)oxy)-N-(thiazol-4-yl)benzenesulfonamide,
79) 5-chloro-2-fluoro-4-((2'-fluoro-6-(3-fluorophenyl)-[4,4'-bipyridin]-3-yl)oxy)-N-(thiazol-4-yl)benzenesulfonamide,
80) 5-chloro-4-((6-(3,4-difluorophenyl)-2'-fluoro-[4,4'-bipyridin]-3-yl)oxy)-2-fluoro-N-(thiazol-4-yl)benzenesulfonamide,
81) 5-chloro-4-((6'-(5-chloro-2-fluorophenyl)-[3,4'-bipyridin]-3'-yl)oxy)-2-fluoro-N-(thiazol-4-yl)benzenesulfonamide,
82) 5-chloro-4-((6'-(3,4-difluorophenyl)-[3,4'-bipyridin]-3'-yl)oxy)-2-fluoro-N-(thiazol-4-yl)benzenesulfonamide,
83) 3-cyano-4-((6-(3-fluorophenyl)-4-(1H-pyrazol-4-yl)pyridin-3-yl)oxy)-N-(thiazol-4-yl)benzenesulfonamide,
84) 3-cyano-4-((6'-(3-fluorophenyl)-[3,4'-bipyridin]-3'-yl)oxy)-N-(thiazol-4-yl)benzenesulfonamide,
85) 3-cyano-4-((6'-(3,4-difluorophenyl)-[3,4'-bipyridin]-3'-yl)oxy)-N-(thiazol-4-yl)benzenesulfonamide,
86) 3-cyano-4-((6'-(3-fluoro-4-(trifluoromethyl)phenyl)-[3,4'-bipyridin]-3'-yl)oxy)-N-(thiazol-4-yl)benzenesulfonamide,
87) 2,5-difluoro-4-((6'-(3-fluorophenyl)-[3,4'-bipyridin]-3'-yl)oxy)-N-(thiazol-4-yl)benzenesulfonamide,
88) 4-((6'-(3,4-difluorophenyl)-[3,4'-bipyridin]-3'-yl)oxy)-2,5-difluoro-N-(thiazol-4-yl)benzenesulfonamide,
89) 2,5-difluoro-4-((6'-(3-fluoro-4-(trifluoromethyl)phenyl)-[3,4'-bipyridin]-3'-yl)oxy)-N-(thiazol-4-yl)benzenesulfonamide,
90) 3-cyano-4-((6-(4-fluorophenyl)-4-(1H-pyrazol-4-yl)pyridin-3-yl)oxy)-N-(thiazol-4-yl)benzenesulfonamide,
91) 3-cyano-4-((6-(3,4-difluorophenyl)-4-(1H-pyrazol-4-yl)pyridin-3-yl)oxy)-N-(thiazol-4-yl)benzenesulfonamide,
92) 3-cyano-4-((6-(3-fluorophenyl)-4-(pyrimidin-5-yl)pyridin-3-yl)oxy)-N-(thiazol-4-yl)benzenesulfonamide,
93) 3-cyano-4-((6-(3,4-difluorophenyl)-4-(pyrimidin-5-yl)pyridin-3-yl)oxy)-N-(thiazol-4-yl)benzenesulfonamide,
94) 3-cyano-4-((6-(3-fluoro-4-(trifluoromethyl)phenyl)-4-(pyrimidin-5-yl)pyridin-3-yl)oxy)-N-(thiazol-4-yl)benzenesulfonamide,
95) 2,5-difluoro-4-((6-(3-fluorophenyl)-4-(pyrimidin-5-yl)pyridin-3-yl)oxy)-N-(thiazol-4-yl)benzenesulfonamide, 96) 4-((6-(3,4-difluorophenyl)-4-(pyrimidin-5-yl)pyridin-3-yl)oxy)-2,5-difluoro-N-(thiazol-4-yl)benzenesulfonamide,
97) 2,5-difluoro-4-((6-(3-fluoro-4-(trifluoromethyl)phenyl)-4-(pyrimidin-5-yl)pyridin-3-yl)oxy)-N-(thiazol-4-yl)benzenesulfonamide,
98) 5-chloro-4-((6-(3,4-difluorophenyl)-4-(1H-pyrazol-4-yl)pyridin-3-yl)oxy)-2-fluoro-N-(thiazol-4-yl)benzenesulfonamide,
99) 5-chloro-2-fluoro-4-((6'-(3-fluorophenyl)-5-(pyrrolidin-1-yl)-[3,4'-bipyridin]-3'-yl)oxy)-N-(thiazol-4-yl)benzenesulfonamide,
100) 5-chloro-2-fluoro-4-((6-(3-fluorophenyl)-4-(1-(pyridin-3-yl)-1H-imidazol-4-yl)pyridin-3-yl)oxy)-N-(thiazol-4-yl)benzenesulfonamide,
101) 5-chloro-2-fluoro-4-((6-(3-fluorophenyl)-2'-morpholino-[4,4'-bipyridin]-3-yl)oxy)-N-(thiazol-4-yl)benzenesulfonamide,
102) 5-chloro-2-fluoro-4-((6-(3-fluorophenyl)-2'-(piperidin-1-yl)-[4,4'-bipyridin]-3-yl)oxy)-N-(thiazol-4-yl)benzenesulfonamide,
103) 3-cyano-4-((2'-fluoro-6-(furan-3-yl)-[2,3'-bipyridin]-5-yl)oxy)-N-(thiazol-2-yl)benzenesulfonamide,
104) 3-cyano-4-((6'-fluoro-6-(furan-3-yl)-[2,3'-bipyridin]-5-yl)oxy)-N-(thiazol-2-yl)benzenesulfonamide,
105) 3-cyano-4-((6-(furan-3-yl)-[2,3'-bipyridin]-5-yl)oxy)-N-(thiazol-2-yl)benzenesulfonamide,
106) 3-cyano-4-((2-(furan-3-yl)-6-(pyrimidin-5-yl)pyridin-3-yl)oxy)-N-(thiazol-2-yl)benzenesulfonamide,
107) 3-cyano-4-((2'-fluoro-6-(1-methyl-1H-pyrazol-5-yl)-[2,4'-bipyridin]-5-yl)oxy)-N-(thiazol-2-yl)benzenesulfonamide,
108) 3-cyano-4-((6-(2-fluorophenyl)-2-(furan-3-yl)pyridin-3-yl)oxy)-N-(thiazol-2-yl)benzenesulfonamide,
109) 3-cyano-4-((6-(4-fluorophenyl)-2-(furan-3-yl)pyridin-3-yl)oxy)-N-(thiazol-2-yl)benzenesulfonamide,
110) 3-cyano-4-((6-(3-fluorophenyl)-2-(furan-3-yl)pyridin-3-yl)oxy)-N-(thiazol-2-yl)benzenesulfonamide,
111) 3-cyano-4-((6-(furan-3-yl)-[2,4'-bipyridin]-5-yl)oxy)-N-(thiazol-2-yl)benzenesulfonamide,
112) 3-cyano-4-((2'-fluoro-6-(furan-3-yl)-[2,4'-bipyridin]-5-yl)oxy)-N-(thiazol-2-yl)benzenesulfonamide,
113) 3-cyano-4-((2-(furan-3-yl)-6-(thiophen-3-yl)pyridin-3-yl)oxy)-N-(thiazol-2-yl)benzenesulfonamide,
114) 3-cyano-4-((2,6-di(furan-3-yl)pyridin-3-yl)oxy)-N-(thiazol-2-yl)benzenesulfonamide,
115) 3-cyano-4-((6'-fluoro-6-(1-methyl-1H-pyrazol-5-yl)-[2,3'-bipyridin]-5-yl)oxy)-N-(thiazol-2-yl)benzenesulfonamide,
116) 3-cyano-4-((2'-fluoro-6-(1-methyl-1H-pyrazol-5-yl)-[2,3'-bipyridin]-5-yl)oxy)-N-(thiazol-2-yl)benzenesulfonamide,
117) 3-cyano-4-((6-(3-fluorophenyl)-2-(1-methyl-1H-pyrazol-5-yl)pyridin-3-yl)oxy)-N-(thiazol-2-yl)benzenesulfonamide,
118) 3-cyano-4-((6-(2-fluorophenyl)-2-(1-methyl-1H-pyrazol-5-yl)pyridin-3-yl)oxy)-N-(thiazol-2-yl)benzenesulfonamide,
119) 3-cyano-4-((2-(1-methyl-1H-pyrazol-5-yl)-6-(thiophen-3-yl)pyridin-3-yl)oxy)-N-(thiazol-2-yl)benzenesulfonamide,
120) 3-cyano-4-((6-(1-methyl-1H-pyrazol-4-yl)-2-(1-methyl-1H-pyrazol-5-yl)pyridin-3-yl)oxy)-N-(thiazol-2-yl)benzenesulfonamide,
121) 3-cyano-4-((6-(isoxazol-4-yl)-2-(1-methyl-1H-pyrazol-5-yl)pyridin-3-yl)oxy)-N-(thiazol-2-yl)benzenesulfonamide,
122) 3-cyano-4-((6-(3-fluorophenyl)-2-(1-methyl-1H-pyrazol-4-yl)pyridin-3-yl)oxy)-N-(thiazol-2-yl)benzenesulfonamide,
123) 3-cyano-4-((2'-fluoro-6-(1-methyl-1H-pyrazol-4-yl)-[2,3'-bipyridin]-5-yl)oxy)-N-(thiazol-2-yl)benzenesulfonamide,
124) 3-cyano-4-((6'-fluoro-6-(1-methyl-1H-pyrazol-4-yl)-[2,3'-bipyridin]-5-yl)oxy)-N-(thiazol-2-yl)benzenesulfonamide,
125) 3-cyano-4-((2'-fluoro-6-(1-methyl-1H-pyrazol-4-yl)-[2,4'-bipyridin]-5-yl)oxy)-N-(thiazol-2-yl)benzenesulfonamide,
126) 3-cyano-4-((2',6'-difluoro-6-(1-methyl-1H-pyrazol-4-yl)-[2,3'-bipyridin]-5-yl)oxy)-N-(thiazol-2-yl)benzenesulfonamide,
127) 3-cyano-4-((2',6'-difluoro-6-(furan-3-yl)-[2,3'-bipyridin]-5-yl)oxy)-N-(thiazol-2-yl)benzenesulfonamide,
128) 3-cyano-4-((2',6'-difluoro-6-(1-methyl-1H-pyrazol-5-yl)-[2,3'-bipyridin]-5-yl)oxy)-N-(thiazol-2-yl)benzenesulfonamide,
129) 5-chloro-4-((2',6'-difluoro-6-(furan-3-yl)-[2,3'-bipyridin]-5-yl)oxy)-2-fluoro-N-(thiazol-4-yl)benzenesulfonamide,
130) 5-chloro-2-fluoro-4-((6'-fluoro-6-(furan-3-yl)-[2,3'-bipyridin]-5-yl)oxy)-N-(thiazol-4-yl)benzenesulfonamide,
131) 5-chloro-2-fluoro-4-((6-(4-fluorophenyl)-2-(furan-3-yl)pyridin-3-yl)oxy)-N-(thiazol-4-yl)benzenesulfonamide,
132) 5-chloro-2-fluoro-4-((2'-fluoro-6-(furan-3-yl)-[2,4'-bipyridin]-5-yl)oxy)-N-(thiazol-4-yl)benzenesulfonamide,
133) 5-chloro-2-fluoro-4-((6-(2-fluorophenyl)-2-(furan-3-yl)pyridin-3-yl)oxy)-N-(thiazol-4-yl)benzenesulfonamide,
134) 5-chloro-4-((2',6'-difluoro-6-(1-methyl-1H-pyrazol-5-yl)-[2,3'-bipyridin]-5-yl)oxy)-2-fluoro-N-(thiazol-4-yl)benzenesulfonamide,
135) 5-chloro-2-fluoro-4-((6-(4-fluorophenyl)-2-(1-methyl-1H-pyrazol-5-yl)pyridin-3-yl)oxy)-N-(thiazol-4-yl)benzenesulfonamide,
136) 5-chloro-2-fluoro-4-((6-(2-fluorophenyl)-2-(1-methyl-1H-pyrazol-5-yl)pyridin-3-yl)oxy)-N-(thiazol-4-yl)benzenesulfonamide,
137) 5-chloro-2-fluoro-4-((6'-fluoro-6-(1-methyl-1H-pyrazol-5-yl)-[2,3'-bipyridin]-5-yl)oxy)-N-(thiazol-4-yl)benzenesulfonamide,
138) 4-((4-chloro-2-(1-methyl-1H-pyrazol-5-yl)phenyl)(hydroxy)methyl)-N-(thiazol-2-yl)benzenesulfonamide,
139) 4-((4-chloro-2-(1H-pyrazol-4-yl)phenyl)(hydroxy)methyl)-3-fluoro-N-(thiazol-2-yl)benzenesulfonamide,
140) 4-((4-chloro-2-(furan-3-yl)phenyl)(hydroxy)methyl)-3-fluoro-N-(thiazol-2-yl)benzenesulfonamide,
141) 4-((2,4-di(furan-3-yl)phenyl)(hydroxy)methyl)-3-fluoro-N-(thiazol-2-yl)benzenesulfonamide,
142) 3-fluoro-4-(hydroxy(2-(1-methyl-1H-pyrazol-5-yl)phenyl)methyl)-N-(thiazol-2-yl)benzenesulfonamide,
143) 4-((4-chloro-2-(furan-3-yl)phenyl)(hydroxy)methyl)-N-(thiazol-2-yl)benzenesulfonamide,
144) 4-((4-chloro-2-(1-methyl-1H-pyrazol-5-yl)phenyl)(hydroxy)methyl)-3-fluoro-N-(thiazol-2-yl)benzenesulfonamide,
145) 4-((4-chloro-2-(pyridin-3-yl)phenyl)(hydroxy)methyl)-3-fluoro-N-(thiazol-2-yl)benzenesulfonamide,
146) 4-((4-chloro-2-(pyridin-4-yl)phenyl)(hydroxy)methyl)-3-fluoro-N-(thiazol-2-yl)benzenesulfonamide, 147) 4-((4-chloro-2-(pyridin-4-yl)phenyl)(hydroxy)methyl)-N-(thiazol-2-yl)benzenesulfonamide,
148) 4-((4-chloro-2-(pyridin-3-yl)phenyl)(hydroxy)methyl)-N-(thiazol-2-yl)benzenesulfonamide,
149) 4-((2,4-di(furan-3-yl)phenyl)(hydroxy)methyl)-N-(thiazol-2-yl)benzenesulfonamide,
150) 4-((4-(2-fluoropyridin-3-yl)-2-(furan-3-yl)phenyl)(hydroxy)methyl)-N-(thiazol-2-yl)benzenesulfonamide,
151) 4-((4-(6-fluoropyridin-3-yl)-2-(furan-3-yl)phenyl)(hydroxy)methyl)-N-(thiazol-2-yl)benzenesulfonamide,
152) 4-((2'-fluoro-3-(furan-3-yl)-[1,1'-biphenyl]-4-yl)(hydroxy)methyl)-N-(thiazol-2-yl)benzenesulfonamide,
153) 4-((3'-fluoro-3-(furan-3-yl)-[1,1'-biphenyl]-4-yl)(hydroxy)methyl)-N-(thiazol-2-yl)benzenesulfonamide,
154) 4-((4'-fluoro-3-(furan-3-yl)-[1,1'-biphenyl]-4-yl)(hydroxy)methyl)-N-(thiazol-2-yl)benzenesulfonamide,
155) 3-fluoro-4-((2-(furan-3-yl)pyridin-3-yl)(hydroxy)methyl)-N-(thiazol-2-yl)benzenesulfonamide,
156) 4-((2-(furan-3-yl)pyridin-3-yl)(hydroxy)methyl)-N-(thiazol-2-yl)benzenesulfonamide, and
157) 3-fluoro-4-(hydroxy(2-phenylpyridin-3-yl)methyl)-N-(thiazol-2-yl)benzenesulfonamide.

11. A pharmaceutical composition for treating a sodium channel blocker-related disease selected from the group consisting of acute pain, chronic pain, neuropathic pain, post-surgery pain, migraine, arthralgia, neuropathy, nerve injury, diabetic neuropathy, neuropathic disease, epilepsy, arrhythmia, myotonia, ataxia, multiple sclerosis, irritable bowel syndrome, urinary incontinence, visceral pain, depression, erythromelalgia, and paroxysmal extreme pain disorder (PEPD), comprising the compound or pharmaceutically acceptable salt thereof of claim 1 as an active ingredient.

* * * * *